United States Patent
Morinaka et al.

(10) Patent No.: US 11,545,697 B2
(45) Date of Patent: Jan. 3, 2023

(54) ADDITIVE FOR NON-AQUEOUS ELECTROLYTE SOLUTION, ELECTROLYTE SOLUTION FOR NON-AQUEOUS ELECTROLYTE SOLUTION BATTERY, AND NON-AQUEOUS ELECTROLYTE SOLUTION BATTERY

(71) Applicant: CENTRAL GLASS CO., LTD., Yamaguchi (JP)

(72) Inventors: Takayoshi Morinaka, Ube (JP); Keita Nakahara, Shimonoseki (JP); Susumu Iwasaki, Ube (JP); Wataru Kawabata, Ube (JP); Mikihiro Takahashi, Ube (JP)

(73) Assignee: CENTRAL GLASS CO., LTD., Yamaguchi (JP)

( * ) Notice: Subject to any disclaimer, the term of this patent is extended or adjusted under 35 U.S.C. 154(b) by 306 days.

(21) Appl. No.: 16/645,601

(22) PCT Filed: Sep. 12, 2018

(86) PCT No.: PCT/JP2018/033843
§ 371 (c)(1),
(2) Date: Mar. 9, 2020

(87) PCT Pub. No.: WO2019/054417
PCT Pub. Date: Mar. 21, 2019

(65) Prior Publication Data
US 2020/0313236 A1    Oct. 1, 2020

(30) Foreign Application Priority Data
Sep. 12, 2017 (JP) .............................. JP2017-175033

(51) Int. Cl.
| | | |
|---|---|---|
| *H01M 10/0567* | (2010.01) | |
| *H01M 10/0525* | (2010.01) | |
| *H01M 10/0568* | (2010.01) | |
| *H01M 10/0569* | (2010.01) | |
| *H01M 10/054* | (2010.01) | |

(52) U.S. Cl.
CPC ..... *H01M 10/0567* (2013.01); *H01M 10/054* (2013.01); *H01M 10/0525* (2013.01); *H01M 10/0568* (2013.01); *H01M 10/0569* (2013.01); *H01M 2300/0028* (2013.01); *H01M 2300/0051* (2013.01)

(58) Field of Classification Search
CPC .................................................. H01M 10/0567
See application file for complete search history.

(56) References Cited

U.S. PATENT DOCUMENTS
| | | |
|---|---|---|
| 6,380,429 B1 | 4/2002 | Smith |
| 2014/0017574 A1 | 1/2014 | Ito et al. |
| 2014/0234696 A1 | 8/2014 | Sakuma et al. |

FOREIGN PATENT DOCUMENTS
| | | |
|---|---|---|
| EP | 3 229 306 | 10/2017 |
| GB | 1 603 122 | 11/1981 |
| IN | 164008 | * 12/1988 |
| JP | 2000-123867 | 4/2000 |
| JP | 2002-280063 | 9/2002 |
| JP | 2002-329528 | 11/2002 |
| JP | 2003-510306 | 3/2003 |
| JP | 2004-259697 | 9/2004 |

(Continued)

OTHER PUBLICATIONS

Machine translation of JP 2002-280063, Sep. 2002.*
Masahito Ochiai et al., "Imination of Sulfides and Sulfoxides with Sulfonylimino-lambda3-Bromane under Mild, Metal-Free Conditions," Chemistry—A European Journal 16, 2020, 8713-8716.*
Office Action dated Jan. 13, 2022 in Korean Patent Application No. 10-2020-7010556, with English-language translation.
International Search Report dated Dec. 4, 2018 in International (PCT) Application No. PCT/JP2018/033843.
Extended European Search Report dated May 7, 2021 in corresponding European Patent Application No. 18856762.2.

(Continued)

*Primary Examiner* — Jonathan Crepeau
(74) *Attorney, Agent, or Firm* — Wenderoth, Lind & Ponack, L.L.P.

(57) ABSTRACT

An additive for a non-aqueous electrolyte solution that can suppress the initial gas generation amount when used in a non-aqueous electrolyte solution battery. The additive for a non-aqueous electrolyte solution is represented by any one of formulae [1] to [4]:

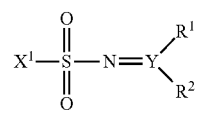

[1]

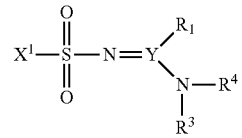

[2]

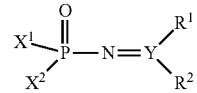

[3]

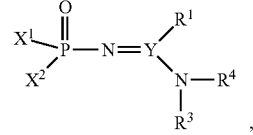

[4]

wherein $R^1$, $R^2$, $R^3$, $R^4$, $X^1$, $X^2$ and Y are as defined in the specification.

9 Claims, No Drawings

(56) References Cited

FOREIGN PATENT DOCUMENTS

| JP | 2013-48077 | 3/2013 |
|---|---|---|
| JP | 2014-157738 | 8/2014 |
| JP | 2014-194866 | 10/2014 |
| WO | 2016/088773 | 6/2016 |

OTHER PUBLICATIONS

A.V. Prosyanik et al., "Thermal Z, E-isomerization of imines, VI. N-(Arylsulfonyl)imines of acetone and 2,6-di-tert-butyl-1,4-benzoquinone", Zhurnal Organicheskoi Khimii, 1987, vol. 23, No. 2, pp. 375-382, XP009510140.

E.N. Suslova et al., "Synthesis of acyclic α-and β-silyl sulfimides", Journal of Chemical Society, Perkin Transactions 1, 2000, No. 18, pp. 3140-3142, XP055798697.

E. Behrend et al., "Pseudoha logenverbindungen. XX. Perfluorierte alkan-und phenylsulfonylpseudohal ogenide" Journal of Fluorine Chemistry, 1974, vol. 4, No. 1, pp. 83-98, XP055798693.

H.W. Roesky et al., "Darstellung und Untersuchung von Fluorsulfurylverbindungen" Chemische Berichte, 1968, vol. 101, No. 1, pp. 162-173, XP002104843.

R. V. Smaliy et al., "Reactions of isocyanatophosphoryl difluoride with π-abundant nitrogen heterocycles and carbonyl compounds", Russian Chemical Bulletin, International Edition Seriya Khimicheskaya, 2006, vol. 55, No. 3, pp. 585-587, XP019407014.

Masahito Ochiai et al., "Imination of Sulfides and Sulfoxides with Sulfonylimino-$\lambda^3$-Bromane under Mild, Metal-Free Conditions", Chemistry—A European Journal, 2010, vol. 16, pp. 8713-8718

\* cited by examiner

ADDITIVE FOR NON-AQUEOUS ELECTROLYTE SOLUTION, ELECTROLYTE SOLUTION FOR NON-AQUEOUS ELECTROLYTE SOLUTION BATTERY, AND NON-AQUEOUS ELECTROLYTE SOLUTION BATTERY

FIELD OF THE INVENTION

The present invention relates to an additive for a non-aqueous electrolyte solution that can suppress the initial gas generation amount (the amount of gas generated due to charge and discharge (such as initial charge and discharge or aging) that are performed before degassing when the battery is manufactured) when used in a non-aqueous-electrolyte solution battery, as well as an electrolyte solution for a non-aqueous-electrolyte solution battery containing the additive, and a non-aqueous-electrolyte solution battery using it.

BACKGROUND TECHNOLOGY

In recent years, storage systems to be applied to small equipment that needs high energy density, such as information-technology-related equipment or communication equipment, specifically, personal computers, video cameras, digital still cameras, and cell phones, and storage systems to be applied to large equipment that needs high power, such as auxiliary power and energy storage for electric vehicles, hybrid electric vehicles and fuel cell electric vehicles have received attention. A non-aqueous electrolyte battery such as a lithium ion battery, a lithium battery, a lithium ion capacitor or a sodium ion battery has been actively developed as a candidate thereof.

Although many of these non-aqueous-electrolyte solution batteries have already been put into practical use, each property is not satisfactory in various applications. In particular, in case of the use of being mounted on a vehicle such as an electric vehicle, it is necessary to improve the manufacturing yield of the battery, in order to reduce the cost of the battery. In order to improve the yield, it is necessary to simplify the degassing process when the battery is manufactured. For this purpose, it is required to suppress the gas generation amount at the time of initial charge.

Until now, as a means of improving the properties of non-aqueous electrolyte solution batteries and reducing the gas generation amount, optimization of various battery components including positive and negative electrode active materials has been studied. Non-aqueous electrolyte solution-related technology is also no exception, and it has been proposed to suppress deterioration due to decomposition of the electrolyte solution on the surface of an active positive or negative electrode with various additives. For example, Patent Documents 1 and 2 propose to improve battery properties of a lithium ion battery by adding vinylene carbonate or unsaturated sultone to the electrolyte solution. In addition, for example, Patent Document 3 proposes to improve battery properties of a sodium ion battery by adding fluoroethylene carbonate to the electrolyte solution.

PRIOR ART DOCUMENTS

Patent Documents

Patent Document 1: Japanese Patent Un-examined Publication number (hereinafter referred to simply as JP-A number) JP-A-2000-123867

Patent Document 2: JP-A-2002-329528
Patent Document 3: JP-A-2013-048077

SUMMARY OF THE INVENTION

Subject to be Attained by the Invention

In non-aqueous electrolyte solution batteries using non-aqueous electrolyte solutions disclosed in the prior art documents, the effect of reducing the initial gas generation amount (the amount of gas generated due to charge and discharge (such as initial charge and discharge or aging) that are performed before degassing when the battery is manufactured) is not satisfactory, and there was room for improvement.

It is an object of the present invention to provide an additive for a non-aqueous electrolyte solution that can suppress the initial gas generation amount when used in a non-aqueous electrolyte solution battery, as well as a non-aqueous electrolyte solution containing the additive and a non-aqueous electrolyte solution battery using the electrolyte solution.

Means for Attaining the Subject

The present inventors have intensively studied in view of the above problems, and as a result, have found that in a non-aqueous electrolyte solution for a non-aqueous-electrolyte solution battery containing a non-aqueous solvent and a solute, when an imine compound having the specific structure is used as an additive for a non-aqueous electrolyte solution, the non-aqueous electrolyte solution battery can suppress the initial gas generation amount, and arrived at the present invention.

That is, the present invention provides an additive for a non-aqueous electrolyte solution (hereinafter, may be generally referred to simply as "imine compound") represented by any one of the following formulae [1] to [4]:

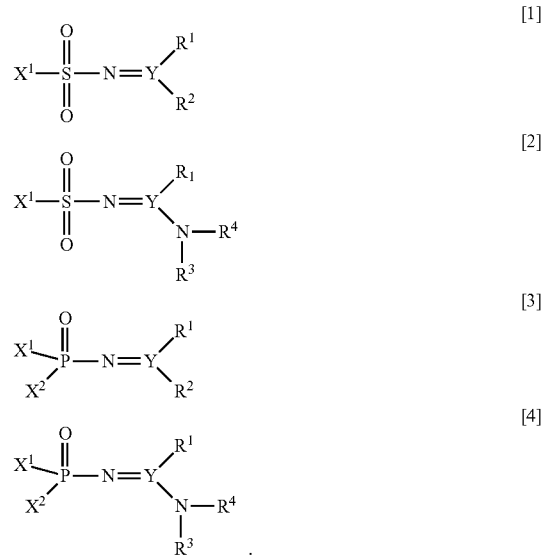

In formulae [1] to [4], the substituents have the following meanings.

$X^1$ and $X^2$ are each independently a fluorine atom or an organic group selected from the group consisting of linear or branched alkyl groups having 1 to 10 carbon atoms, linear or branched alkoxy groups having 1 to 10 carbon atoms, linear or branched alkenyl groups having 2 to carbon atoms, linear or branched alkenyloxy groups having 2 to 10 carbon atoms, linear or branched alkynyl groups having 2 to 10 carbon atoms, linear or branched alkynyloxy groups having 2 to 10 carbon atoms, cycloalkyl groups having 3 to 10 carbon atoms, cycloalkoxy groups having 3 to 10 carbon atoms, cycloalkenyl groups having 3 to 10 carbon atoms, cycloalkenyloxy groups having 3 to 10 carbon atoms, aryl groups having 6 to 10 carbon atoms, and aryloxy groups having 6 to 10 carbon atoms, where the organic group may contain a fluorine atom, an oxygen atom, or an unsaturated bond.

Y is a carbon atom or a sulfur atom.

Incidentally, the phrase "the organic group contains a fluorine atom" specifically means that a hydrogen atom in the group is substituted with a fluorine atom.

In addition, the phrase "the organic group contains an oxygen atom" specifically means, for example, that "—O—" (ether bond) is interposed between the carbon atoms in the group.

$R^1$ and $R^2$ are each independently an organic group selected from the group consisting of linear or branched alkyl groups having 1 to 10 carbon atoms, linear or branched alkoxy groups having 1 to 10 carbon atoms, linear or branched alkenyl groups having 2 to 10 carbon atoms, linear or branched alkenyloxy groups having 2 to 10 carbon atoms, linear or branched alkynyl groups having 2 to 10 carbon atoms, linear or branched alkynyloxy groups having 2 to 10 carbon atoms, cycloalkyl groups having 3 to 10 carbon atoms, cycloalkoxy groups having 3 to 10 carbon atoms, cycloalkenyl groups having 3 to 10 carbon atoms, cycloalkenyloxy groups having 3 to 10 carbon atoms, aryl groups having 6 to 10 carbon atoms, and aryloxy groups having 6 to 10 carbon atoms, where the organic group may contain a fluorine atom, an oxygen atom, or an unsaturated bond.

Incidentally, the phrase "the organic group contains a fluorine atom" specifically means that a hydrogen atom in the group is substituted with a fluorine atom.

In addition, the phrase "the organic group contains an oxygen atom" specifically means, for example, that "—O—" (ether bond) is interposed between the carbon atoms in the group.

$R^3$ and $R^4$ are each independently an organic group selected from the group consisting of linear or branched alkyl groups having 1 to 10 carbon atoms, linear or branched alkenyl groups having 2 to 10 carbon atoms, linear or branched alkynyl groups having 2 to 10 carbon atoms, cycloalkyl groups having 3 to 10 carbon atoms, cycloalkenyl groups having 3 to 10 carbon atoms, and aryl groups having 6 to 10 carbon atoms, where the organic group may contain a fluorine atom, an oxygen atom, or an unsaturated bond.

Incidentally, the phrase "the organic group contains a fluorine atom" specifically means that a hydrogen atom in the group is substituted with a fluorine atom.

In addition, the phrase "the organic group contains an oxygen atom" specifically means, for example, that "—O—" (ether bond) is interposed between the carbon atoms in the group.

In addition, $R^1$ and $R^2$ or $R^1$ and $R^4$ may form together a cyclic structure as shown in the following formula [5] or [6]:

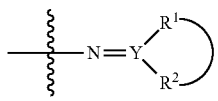

[5]

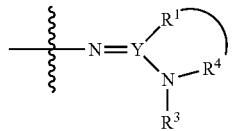

[6]

In addition, the imine compound represented by any one of the above formulae [1] to [4] is preferably a compound in which $X^1$ and $X^2$ are each independently a fluorine atom or a group selected from the group consisting of a methyl group, a trifluoromethyl group, and a phenyl group;

at least one of $R^1$ and $R^2$ is a group selected from the group consisting of a methyl group, a methoxy group, an ethyl group, an ethoxy group, a propyl group, a propoxyl group, a vinyl group, an allyl group, an allyloxy group, an ethynyl group, a 2-propynyl group, a 2-propynyloxy group, a phenyl group, and a phenyloxy group; and at least one $R^3$ and $R^4$ is a group selected from the group consisting of a methyl group, an ethyl group, a propyl group, a vinyl group, an allyl group, an ethynyl group, a 2-propynyl group, and a phenyl group.

In addition, the imine compound represented by any one of the above formulae [1] to [4] is also preferably a compound in which $X^1$ and $X^2$ are each independently a fluorine atom or a group selected from the group consisting of a methyl group, a trifluoromethyl group, and a phenyl group; and $R^1$ and $R^2$ or $R^1$ and $R^4$ form together a cyclic structure represented by any one of the following formulae [7] to [11]:

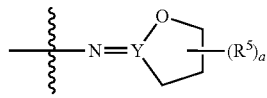

[7]

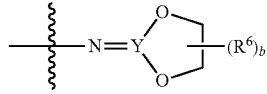

[8]

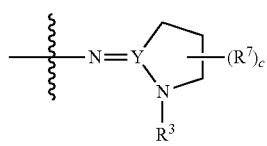

[9]

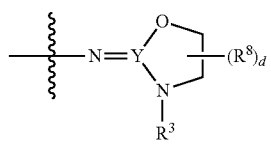

[10]

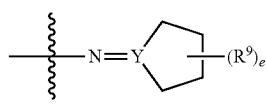

[11]

[$R^5$ to $R^9$ are each independently a fluorine atom or an organic group selected from the group consisting of linear or branched alkyl groups having 1 to 10 carbon atoms, linear or branched alkoxy groups having 1 to 10 carbon atoms, linear or branched alkenyl groups having 2 to 10 carbon atoms, linear or branched alkenyloxy groups having 2 to 10 carbon atoms, linear or branched alkynyl groups having 2 to 10 carbon atoms, linear or branched alkynyloxy groups having 2 to 10 carbon atoms, cycloalkyl groups having 3 to 10 carbon atoms, cycloalkoxy groups having 3 to 10 carbon atoms, cycloalkenyl groups having 3 to 10 carbon atoms, cycloalkenyloxy groups having 3 to 10 carbon atoms, aryl groups having 6 to 10 carbon atoms, and aryloxy groups having 6 to 10 carbon atoms, where the organic group may contain a fluorine atom, an oxygen atom, or an unsaturated bond.

Incidentally, the phrase "the organic group contains a fluorine atom" specifically means that a hydrogen atom in the group is substituted with a fluorine atom.

In addition, the phrase "the organic group contains an oxygen atom" specifically means, for example, that "—O—" (ether bond) is interposed between the carbon atoms in the group.

a and c are each an integer of 0 to 6; b and d are each an integer of 0 to 4; and e is an integer of 0 to 8.]

In addition, in the cyclic structure represented by any one of the above formulae [7] to [11], it is preferable that $R^3$ is a methyl group, an ethyl group, a propyl group, a vinyl group, an allyl group, an ethynyl group, a 2-propynyl group, or a phenyl group;

$R^5$ to $R^9$ are each independently a fluorine atom or a group selected from the group consisting of a methyl group, a vinyl group, an allyl group, an allyloxy group, an ethynyl group, a 2-propynyl group, and a phenyl group; and a to e are each an integer of 0 to 2.

In addition, the present invention relates to an electrolyte solution for a non-aqueous-electrolyte solution battery (hereinafter, may be sometimes referred to simply as a "non-aqueous electrolyte solution" or "electrolyte solution") containing a non-aqueous solvent, a solute, and the above-described additive for a non-aqueous electrolyte solution.

The content of the additive for a non-aqueous electrolyte solution is preferably within a range of 0.001 to 5.0 mass % based on the total amount of the non-aqueous solvent, the solute, and the additive for a non-aqueous electrolyte solution. If the content is higher than 5.0 mass %, the discharge capacity may be decreased due to excessive formation of a film. In contrast, if the content is less than 0.001 mass %, the formation of a film is insufficient, and the effect of improving the properties may become difficult to be realized.

The solute is preferably at least one selected from the group consisting of $LiPF_6$, $LiBF_4$, $LiPF_2(C_2O_4)_2$, $LiPF_4(C_2O_4)$, $LiP(C_2O_4)_3$, $LiBF_2(C_2O_4)$, $LiB(C_2O_4)_2$, $LiPO_2F_2$, $LiN(POF_2)_2$, $LiN(FSO_2)(POF_2)$, $LiN(FSO_2)(POF(OCH_2C\equiv CH))$, $LiN(FSO_2)_2$, $LiN(CF_3SO_2)_2$, $LiN(CF_3SO_2)(FSO_2)$, $LiSO_3F$, $NaPF_6$, $NaBF_4$, $NaPF_2(C_2O_4)_2$, $NaPF_4(O_2O_4)$, $NaP(C_2O_4)_3$, $NaBF_2(C_2O_4)$, $NaB(C_2O_4)_2$, $NaPO_2F_2$, $NaN(POF_2)_2$, $NaN(FSO_2)(POF_2)$, $NaN(FSO_2)(POF(OCH_2C\equiv CH))$, $NaN(FSO_2)_2$, $NaN(CF_3SO_2)_2$, $NaN(CF_3SO_2)(FSO_2)$, and $NaSO_3F$.

The non-aqueous electrolyte solution may further contain at least one selected from the group consisting of vinylene carbonate, fluoroethylene carbonate, ethynylethylene carbonate, trans-di fluoroethylene carbonate, (ethoxy) pentafluorocyclotriphosphazene, tetravinylsilane, and 1,3-propanesultone.

In addition, the non-aqueous solvent is preferably at least one selected from the group consisting of cyclic carbonates, chain carbonates, cyclic esters, chain esters, cyclic ethers, chain ethers, sulfone compounds, sulfoxide compounds, and ionic liquids.

In addition, the present invention relates to a non-aqueous-electrolyte solution battery (hereinafter, may be sometimes referred to simply as a "non-aqueous battery" or "battery") at least including a positive electrode, a negative electrode, and the above-described electrolyte solution for a non-aqueous-electrolyte solution battery.

Effect by the Invention

According to the present invention, it is possible to provide an additive for a non-aqueous electrolyte solution that can suppress the initial gas generation amount when used in a non-aqueous electrolyte solution battery, as well as a non-aqueous electrolyte solution containing the additive and a non-aqueous electrolyte solution battery using the electrolyte solution.

DETAILED DESCRIPTION OF THE INVENTION

The present invention will now be described in detail below. However, the descriptions of the components described below are examples of the embodiments of the present invention, and the scope of the invention is not limited to these embodiments and can be carried out with various modifications within the range of the gist of the present invention.

1. Additive for a Non-Aqueous Electrolyte Solution

Although the mechanism of the action of improving the battery properties by the present invention is not clear, it is conceived that the imine compound represented by any one of the above formulae [1] to [4] is partially decomposed at the interface between the positive electrode and the electrolyte solution and the interface between the negative electrode and the electrolyte solution to form a film. It is conceived that this film inhibits the direct contact between the non-aqueous solvent or the solute and the active material, so as to prevent the decomposition of the non-aqueous solvent and the solute to inhibit the deterioration of the battery performance (decomposition of the solvent and generation of gas at higher temperature (about 70° C. or less)).

In the above formulae [1] to [4], the groups represented by $X^1$, $X^2$, $R^1$, and $R^2$ are as follows. Examples of the alkyl group and the alkoxyl group include alkyl groups and fluorine-containing alkyl groups having 1 to 10 carbon atoms, such as a methyl group, an ethyl group, a propyl group, an isopropyl group, a butyl group, a sec-butyl group, a tert-butyl group, a pentyl group, a trifluoromethyl group, a 2,2-difluoroethyl group, a 2,2,2-trifluoroethyl group, a 2,2,3,3-tetrafluoropropyl group, and a 1,1,1,3,3,3-hexafluoroisopropyl group; and alkoxy groups derived therefrom.

Examples of the alkenyl group and the alkenyloxy group include alkenyl groups and fluorine-containing alkenyl groups having 2 to 10 carbon atoms, such as a vinyl group, an allyl group, a 1-propenyl group, an isopropenyl group, a 2-butenyl group, and a 1,3-butadienyl group; and alkenyloxy groups derived therefrom.

Examples of the alkynyl group and the alkynyloxy group include alkynyl groups and fluorine-containing alkynyl groups having 2 to 10 carbon atoms, such as an ethynyl group, a 2-propynyl group, and a 1,1-dimethyl-2-propynyl group; and alkynyloxy groups derived therefrom. Examples of the cycloalkyl group and the cycloalkoxy group include cycloalkyl groups and fluorine-containing cycloalkyl groups having 3 to 10 carbon atoms, such as a cyclopentyl group and a cyclohexyl group; and cycloalkoxy groups derived therefrom.

Examples of the cycloalkenyl group and the cycloalkenyloxy group include cycloalkenyl groups and fluorine-containing cycloalkenyl groups having 3 to 10 carbon atoms, such as a cyclopentenyl group and a cyclohexenyl group; and cycloalkenyloxy groups derived therefrom.

Examples of the aryl group and the aryloxy group include aryl groups and fluorine-containing aryl groups having 6 to 10 carbon atoms, such as a phenyl group, a tolyl group, and a xylyl group; and aryloxy groups derived therefrom.

In the above formulae [1] to [4], the groups represented by $R^3$ and $R^4$ are as follows. Examples of the alkyl group include alkyl groups and fluorine-containing alkyl groups having 1 to 10 carbon atoms, such as a methyl group, an ethyl group, a propyl group, an isopropyl group, a butyl group, a sec-butyl group, a tert-butyl group, a pentyl group, a trifluoromethyl group, a 2,2-difluoroethyl group, a 2,2,2-trifluoroethyl group, a 2,2,3,3-tetrafluoropropyl group, and a 1,1,1,3,3,3-hexafluoroisopropyl group. Examples of the alkenyl group include alkenyl groups and fluorine-containing alkenyl groups having 2 to 10 carbon atoms, such as a vinyl group, an allyl group, a 1-propenyl group, an isopropenyl group, a 2-butenyl group, and a 1,3-butadienyl group. Examples of the alkynyl group include alkynyl groups and fluorine-containing alkynyl groups having 2 to 10 carbon atoms, such as an ethynyl group, a 2-propynyl group, and a 1,1-dimethyl-2-propynyl group. Examples of the cycloalkyl group include cycloalkyl groups and fluorine-containing cycloalkyl groups having 3 to 10 carbon atoms, such as a cyclopentyl group and a cyclohexyl group. Examples of the cycloalkenyl group include cycloalkenyl groups and fluorine-containing cycloalkenyl groups having 3 to 10 carbon atoms, such as a cyclopentenyl group and a cyclohexenyl group. Examples of the aryl group include aryl groups and fluorine-containing aryl groups having 6 to 10 carbon atoms, such as a phenyl group, a tolyl group, and a xylyl group.

In addition, $R^1$ and $R^2$ or $R^1$ and $R^4$ may form together a cyclic structure as shown in the above formula [5] or [6], as described above, and examples of the structure include cyclic structures represented by the above formulae [7] to [11].

In the above formulae [7] to [11], the groups represented by $R^5$ to $R^9$ are as follows.

Example of the alkyl group and the alkoxyl group include alkyl groups and fluorine-containing alkyl groups having 1 to 10 carbon atoms, such as a methyl group, an ethyl group, a propyl group, an isopropyl group, a butyl group, a sec-butyl group, a tert-butyl group, a pentyl group, a trifluoromethyl group, a 2,2-difluoroethyl group, a 2,2,2-trifluoroethyl group, a 2,2,3,3-tetrafluoropropyl group, and a 1,1,1,3,3,3-hexafluoroisopropyl group; and alkoxy groups derived therefrom.

Examples of the alkenyl group and the alkenyloxy group include alkenyl groups and fluorine-containing alkenyl groups having 2 to 10 carbon atoms, such as a vinyl group, an allyl group, a 1-propenyl group, an isopropenyl group, a 2-butenyl group, and a 1,3-butadienyl group; and alkenyloxy groups derived therefrom.

Examples of the alkynyl group and the alkynyloxy group include alkynyl groups and fluorine-containing alkynyl groups having 2 to 10 carbon atoms, such as an ethynyl group, a 2-propynyl group, and a 1,1-dimethyl-2-propynyl group; and alkynyloxy groups derived therefrom.

Examples of the cycloalkyl group and the cycloalkoxy group include cycloalkyl groups and fluorine-containing cycloalkyl group having 3 to 10 carbon atoms, such as a cyclopentyl group and a cyclohexyl group; and cycloalkoxy groups derived therefrom.

Examples of the cycloalkenyl group and the cycloalkenyloxy group include cycloalkenyl groups and fluorine-containing cycloalkenyl groups having 3 to 10 carbon atoms, such as a cyclopentenyl group and a cyclohexenyl group; and cycloalkenyloxy groups derived therefrom.

Examples of the aryl group and the aryloxy group include aryl groups and fluorine-containing aryl groups having 6 to 10 carbon atoms, such as a phenyl group, a tolyl group, and a xylyl group; and aryloxy groups derived therefrom.

More specifically, examples of the imine compound represented by any one of the above formulae [1] to [4] include, but not limited to, the following compounds:

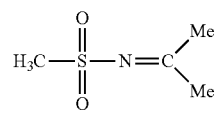
(1C-1)

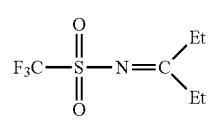
(1C-2)

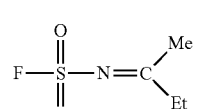
(1C-3)

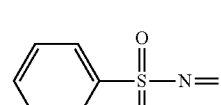
(1C-4)

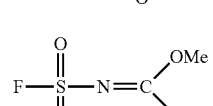
(1C-5)

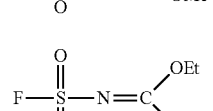
(1C-6)

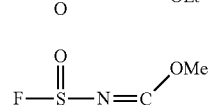
(1C-7)

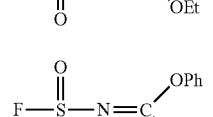
(1C-8)

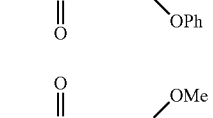
(1C-9)

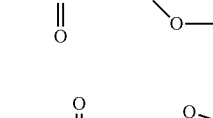
(1C-10)

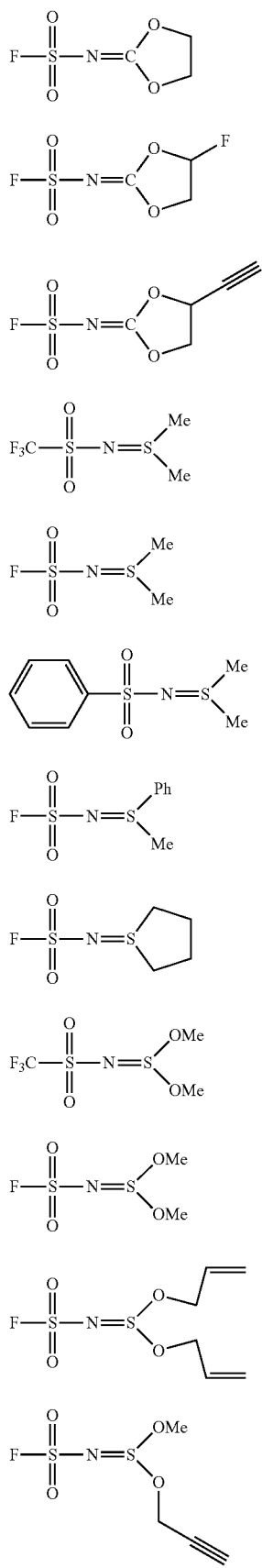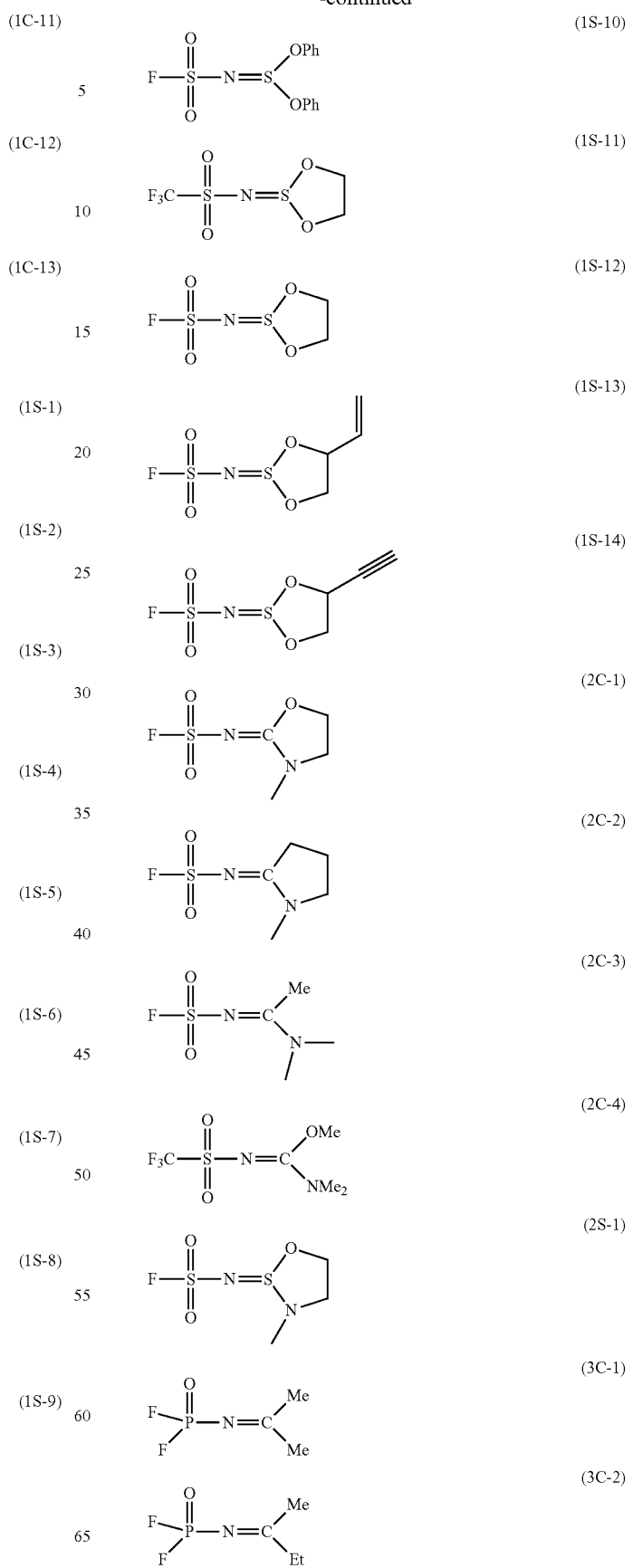

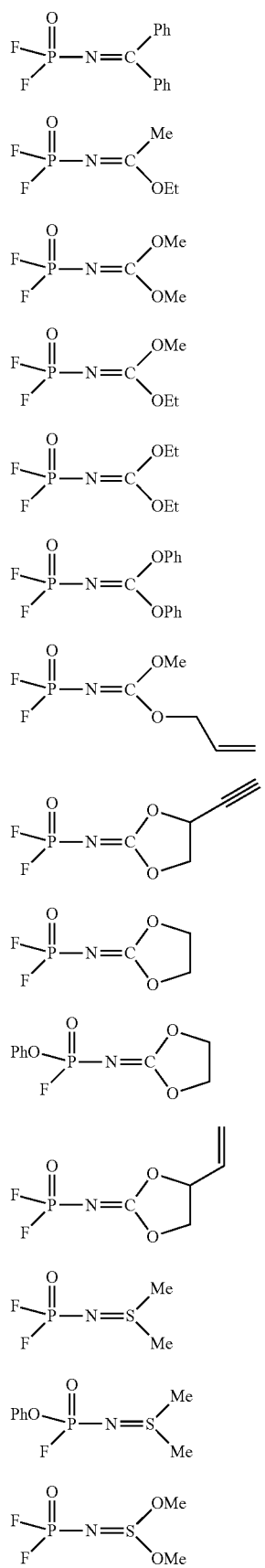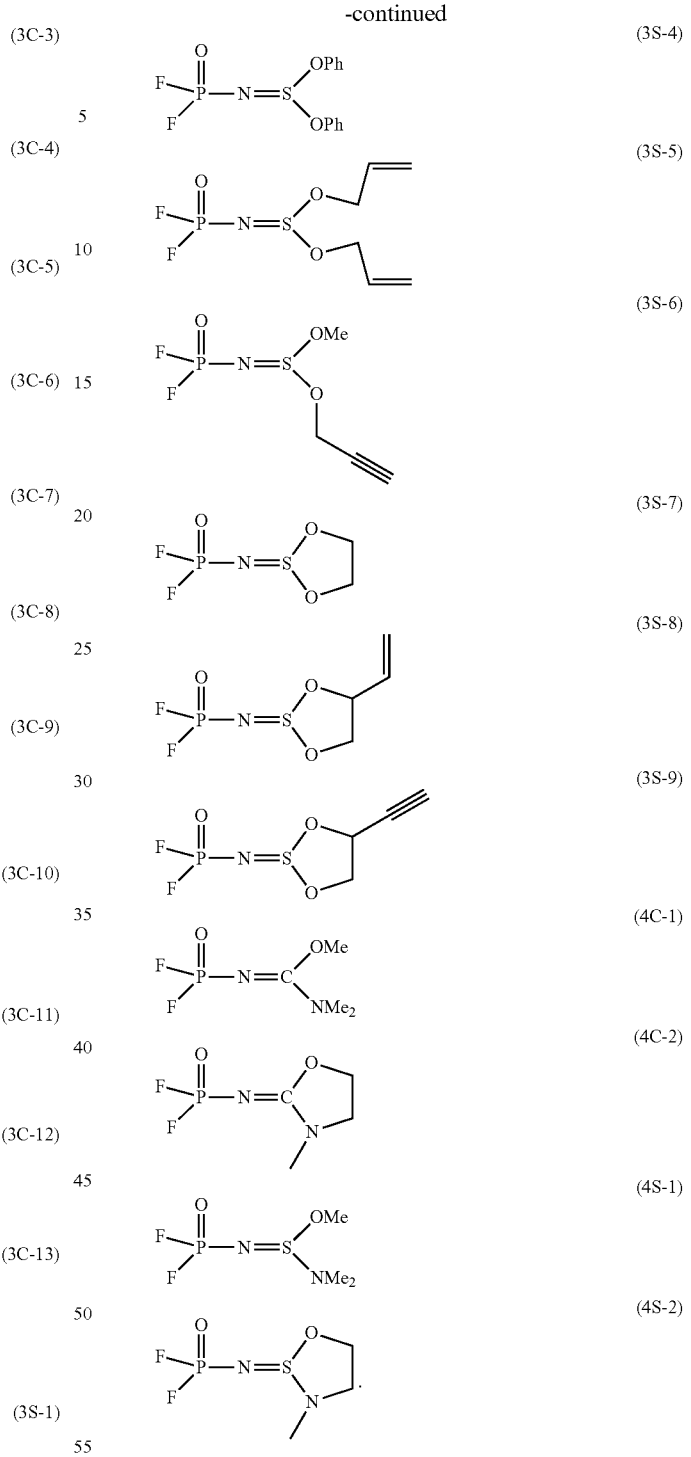

An imine compound including a substituent having a fewer number of carbon atoms or an imine compound containing a larger number of fluorine atoms or oxygen atoms shows a higher reductive decomposition potential on a negative electrode and tends to form a decomposition film before decomposition of the electrolyte solution (solvent) and is therefore conceived to more easily inhibit the gas generation by decomposition of the electrolyte solution (solvent).

Among the above-mentioned imine compounds, (1C-1), (1C-4), (1C-5), (1C-6), (1C-7), (1C-9), (1C-11), (1C-13), (1S-2), (1S-4), (1S-5), (2C-1), (2C-2), (2C-4), (3C-6), (3C-9), and (3S-1) are preferred from the viewpoint of the effect of suppressing the initial gas generation amount.

In addition, among the above-mentioned imine compounds, (1C-1), (1C-4), (1C-6), (1C-7), (1C-9), (1C-11), (1C-13), (1S-2), (1S-3), (1S-9), (2C-1), (2C-2), (2C-4), and (3C-6) are preferred from the viewpoint of easily exhibiting the effect of inhibiting gas generation and the effect of improving the durability at higher temperature (about 70° C. or less) in a well-balanced manner.

The imine compound represented by any one of formulae [1] to [4] preferably has a high purity. In particular, the content of chlorine (Cl) in the imine compound as a raw material before being dissolved in the electrolyte solution is preferably 5000 mass ppm or less, more preferably 1000 mass ppm or less, and further preferably 100 mass ppm or less. The use of the imine compound containing a higher concentration of remaining chlorine (Cl) tends to corrode the battery members and is therefore not preferred. Especially, the content of chloride (Cl) of higher than 5000 mass ppm may corrode the current collector of the non-aqueous-electrolyte solution battery and is not preferred.

In addition, the content of free acids contained in the imine compound represented by any one of formulae [1] to [4] as a raw material before being dissolved in the electrolyte solution is preferably 5000 mass ppm or less and further preferably 1000 mass ppm or less. The content of free acids of higher than 5000 mass ppm may corrode the current collector of the non-aqueous-electrolyte solution battery and is not preferred.

The imine compounds represented by formulae [1] to [4] can be manufactured by various methods, and the manufacturing method is not particularly limited.

In one example of the method, as described in, for example, Tetrahedron Letters, 43, 3957-3959, 2002 and Chem. Ber, 101, 162-173, 1968, a corresponding isocyanate ($X^1SO_2N=C=O$ or $X^1X^2P(=O)N=C=O$) and a corresponding compound having a carbonyl group ($O=CR^1R^2$ or $O=CR^1(NR^3R^4)$) or compound having a sulfoxide group ($O=SR^1R^2$ or $O=SR^1(NR^3R^4)$) are reacted in the absence of a solvent or in a solvent that does not react with them.

In addition, when $X^1$ and $X^2$ are fluorine atoms, the imine compound can also be obtained by reacting a chlorosulfonyl isocyanate or a dichlorophosphonyl isocyanate and a corresponding compound having a carbonyl group ($O=CR^1R^2$ or $O=CR^1(NR^3R^4)$) or compound having a sulfoxide group ($O=SR^1R^2$ or $O=SR^1(NR^3R^4)$) in the absence of a solvent or in a solvent that does not react with them and then replacing the chlorine atoms with fluorine atoms.

2. Non-Aqueous Electrolyte Solution

2-1. Additive for Non-Aqueous Electrolyte Solution

The non-aqueous electrolyte solution of the present invention contains a solute and a non-aqueous solvent both of which will be described below, and the additive for a non-aqueous electrolyte solution described above. The lower limit of the content of the additive for a non-aqueous electrolyte solution in the electrolyte solution is preferably 0.001 mass % or more, more preferably 0.005 mass % or more, and further preferably 0.01 mass % or more based on the total amount of the non-aqueous solvent, the solute, and the additive for a non-aqueous electrolyte solution, and the upper limit is preferably 5.0 mass % or less, more preferably 3.0 mass % or less, and further preferably 2.0 mass % or less.

If the content is lower than 0.001 mass %, since it is difficult to sufficiently obtain the effect of improving the battery properties, such a content is not preferred. In contrast, if the content is higher than 5.0 mass %, since a higher effect is not obtained, such a content is useless, and also since the resistance is increased due to excessive film formation to readily cause deterioration of the battery performance, such a content is not preferred. The above-described imine compounds as the additive for a non-aqueous electrolyte solution may be used alone or in any combination and at any ratio of two or more thereof, within a range not exceeding 5.0 mass % according to the application.

2-2. Solute

The type of the solute of the electrolyte solution for a non-aqueous-electrolyte solution battery of the present invention is not particularly limited, and any electrolyte salt can be used. In a non-aqueous electrolyte solution for a metal cation battery or a non-aqueous electrolyte solution for a capacitor, the solute may be a salt having a metal cation or an onium cation as the ion source. For example, in case of a lithium ion battery, the solute may be a lithium salt as the ion source. In case of a sodium ion battery, the solute may be a sodium salt as the ion source. As the counter anion thereof, in view of the degree of dissociation in the non-aqueous electrolyte solution, it is preferable to contain at least one selected from the group consisting of $PF_6^-$, $BF_4^-$, $PF_2(C_2O_4)_2^-$, $PF_4(C_2O_4)^-$, $P(C_2O_4)_3$, $BF_2(C_2O_4)^-$, $B(C_2O_4)_2^-$, $PO_2F_2^-$, $N(POF_2)_2^-$, $N(FSO_2)(POF_2)^-$, $N(FSO_2)(POF(OCH_2C\equiv CH))^-$, $N(FSO_2)_2^-$, $N(CF_3SO_2)_2^-$, $N(CF_3SO_2)^-$, $(FSO_2)^-$, $SO_3F^-$, and $N(FSO_2)(FCO)^-$. In particular, in view of the energy density, output properties, durability performance, etc. as a battery, use of a combination of two or more thereof is preferred.

Examples of the solute in a lithium battery and a lithium ion battery include electrolyte salts, such as $LiPF_6$, $LiBF_4$, $LiPF_2(C_2O_4)_2$, $LiPF_4(C_2O_4)$, $LiP(C_2O_4)_3$, $LiBF_2(C_2O_4)$, $LiB(C_2O_4)_2$, $LiPO_2F_2$, $LiN(POF_2)_2$, $LiN(FSO_2)(POF_2)$, $LiN(FSO_2)(POF(OCH_2C\equiv CH))$, $LiN(FSO_2)_2$, $LiN(CF_3SO_2)_2$, $LiN(C_2F_5SO_2)_2$, $LiN(CF_3SO_2)(FSO_2)$, $LiSO_3F$, $LiClO_4$, $LiAsF_6$, $LiSbF_6$, $LiCF_3SO_3$, $LiC(CF_3SO_2)_3$, $LiPF_3(C_3F_7)_3$, $LiB(CF_3)_4$, and $LiBF_3(C_2F_5)$.

In addition, examples of the solute in a sodium ion battery include electrolyte salts, such as $NaPF_6$, $NaBF_4$, $NaPF_2(C_2O_4)_2$, $NaPF_4(C_2O_4)$, $NaP(C_2O_4)_3$, $NaBF_2(C_2O_4)$, $NaB(C_2O_4)_2$, $NaPO_2F_2$, $NaN(POF_2)_2$, $NaN(FSO_2)(POF_2)$, $NaN(FSO_2)(POF(OCH_2C\equiv CH))$, $NaN(FSO_2)_2$, $NaN(CF_3SO_2)_2$, $NaN(C_2F_5SO_2)_2$, $NaN(CF_3SO_2)(FSO_2)$, $NaSO_3F$, $NaN(FSO_2)(FCO)$, $NaClO_4$, $NaAsF_6$, $NaSbF_6$, $NaCF_3SO_3$, $NaC(CF_3SO_2)_3$, $NaPF_3(C_3F_7)_3$, $NaB(CF_3)_4$, and $NaBF_3(C_2F_5)$.

These solutes may be used alone or in any combination and at any ratio of two or more thereof, according to the application. In particular, in view of the energy density, output properties, life duration, etc. as a battery, preferred are $LiPF_6$, $LiBF_4$, $LiPF_2(C_2O_4)_2$, $LiPF_4(C_2O_4)$, $LiP(C_2O_4)_3$, $LiBF_2(C_2O_4)$, $LiB(C_2O_4)_2$, $LiPO_2F_2$, $LiN(POF_2)_2$, $LiN(FSO_2)(POF_2)$, $LiN(FSO_2)(POF(OCH_2C\equiv CH))$, $LiN(FSO_2)_2$, $LiN(CF_3SO_2)_2$, $LiN(CF_3SO_2)(FSO_2)$, $LiSO_3F$, $NaPF_6$, $NaBF_4$, $NaPF_2(C_2O_4)_2$, $NaPF_4(C_2O_4)$, $NaP(C_2O_4)_3$, $NaBF_2(C_2O_4)$, $NaB(C_2O_4)_2$, $NaPO_2F_2$, $NaN(POF_2)_2$, $NaN(FSO_2)(POF_2)$, $NaN(FSO_2)(POF(OCH_2C\equiv CH))$, $NaN(FSO_2)_2$, $NaN(CF_3SO_2)_2$, $NaN(CF_3SO_2)(FSO_2)$, and $NaSO_3F$.

A suitable combination of the solutes in a lithium battery and a lithium ion battery is preferably, for example, a combination of (1) at least one selected from the group consisting of LiBF$_4$, LiPF$_2$ (C$_2$O$_4$)$_2$, LiPF$_4$ (C$_2$O$_4$), LiP (C$_2$O$_4$)$_3$, LiBF$_2$ (C$_2$O$_4$), LiB(C$_2$O$_4$)$_2$, LiPO$_2$F$_2$, LiN(POF$_2$)$_2$, LiN(FSO$_2$) (POF$_2$), LiN(FSO$_2$) (POF(OCH$_2$C≡CH)), LiN (FSO$_2$)$_2$, LiN(CF$_3$SO$_2$)$_2$, LiN(CF$_3$SO$_2$) (FSO$_2$) and LiSO$_3$F, with (2) LiPF$_6$. The ratio in the above combination (a molar ratio when LiPF$_6$ is used as one mole) is generally within a range of 1:0.001 to 1:0.5 and preferably 1:0.01 to 1:0.2. Use of a combination of the solutes at the above-mentioned ratio has an effect of further improving various battery properties. In contrast, when the ratio of LiPF$_6$ is lower than 1:0.5, the ionic conductance of the electrolyte solution decreases, and the resistance tends to increase.

The concentration of these solutes is not particularly limited, and the lower limit thereof is preferably 0.5 mol/L or more, more preferably 0.7 mol/L or more, and further preferably 0.9 mol/L or more, and the upper limit is preferably 2.5 mol/L or less, more preferably 2.0 mol/L or less, and further preferably 1.5 mol/L or less. When the concentration is less than 0.5 mol/L, the ionic conductance decreases, and thereby the cycle properties and output properties of the non-aqueous electrolyte solution battery tend to be reduced. In contrast, when the concentration is higher than 2.5 mol/L, the viscosity of the electrolyte solution for a non-aqueous electrolyte solution battery increases, and thereby the ionic conductance likewise tends to be reduced, and the cycle properties and output properties of the non-aqueous electrolyte solution battery may be reduced.

If a large amount of the above solute is dissolved at once in a non-aqueous solvent, the temperature of the non-aqueous electrolyte solution may be increased due to the heat of dissolution of the solute. When the solution temperature is significantly increased, the decomposition of the lithium salt containing a fluorine atom is accelerated, and hydrogen fluoride may be generated. Hydrogen fluoride becomes a cause of deterioration of the battery performance and is therefore not preferred. Accordingly, the solution temperature when the solute is dissolved in a non-aqueous solvent is not particularly limited but is preferably −20° C. to 80° C. and more preferably 0° C. to 60° C.

2-3. Non-Aqueous Solvent

The type of the non-aqueous solvent used in the electrolyte solution for a non-aqueous-electrolyte solution battery of the present invention is not particularly limited, and any non-aqueous solvents can be used. Examples of the non-aqueous solvents include cyclic carbonates, such as propylene carbonate, ethylene carbonate, and butylene carbonate; chain carbonates, such as diethyl carbonate, dimethyl carbonate, and ethyl methyl carbonate; cyclic esters, such as γ-butyrolactone and γ-valerolactone; chain esters, such as methyl acetate and methyl propionate; cyclic ethers, such as tetrahydrofuran, 2-methyltetrahydrofuran, and dioxane; chain ethers, such as dimethoxyethane and diethyl ether; and sulfone compounds and sulfoxide compounds, such as dimethyl sulfoxide and sulfolane. In addition, for example, ionic liquids whose category differs from that of the non-aqueous solvent can be also used. In addition, the non-aqueous solvents used in the present invention may be used alone or may be used in any combination and at any ratio of two or more thereof, according to the application. Among these non-aqueous solvents, from the viewpoint of the electrochemical stability against its redox and the chemical stability related to the heat and the reaction with the solute, propylene carbonate, ethylene carbonate, diethyl carbonate, dimethyl carbonate, and ethyl methyl carbonate are especially preferred.

For example, it is preferable to use one or more selected from cyclic carbonates having a high dielectric constant and one or more selected from chain carbonates or chain esters having a low liquid viscosity, together as the non-aqueous solvent, because such a co-use increases the ionic conductance of the electrolyte solution.

2-4. Other Additives

The above is the description about the basic composition of the electrolyte solution for a non-aqueous electrolyte solution battery of the present invention.

Any additives that have been usually used may be also added to the electrolyte solution for a non-aqueous-electrolyte solution battery of the present invention at any ratio within the range that does not impair the gist of the present invention. Examples of such additives include compounds that have overcharge prevention effect, negative electrode film-forming effect, and positive electrode protection effect, such as vinylene carbonate (hereinafter may be referred to as "VC"), fluoroethylene carbonate, ethynylethylene carbonate, trans-difluoroethylene carbonate, (ethoxy)pentafluorocyclotriphosphazene, tetravinylsilane, 1,3-propanesultone, methylene methanedisulfonate, 1,2-ethanedisulfonic acid anhydride, 1,6-diisocyanatohexane, succinonitrile, cyclohexylbenzene, biphenyl, t-butylbenzene, vinylethylene carbonate, difluoroanisole, dimethylvinylene carbonate, and compounds represented by the following formula [12]:

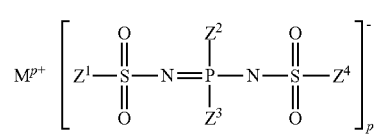

[12]

[in formula [12], $Z^1$ to $Z^4$ are each independently a fluorine atom or an organic group selected from the group consisting of linear or branched alkyl groups having 1 to 10 carbon atoms, linear or branched alkoxy groups having 1 to 10 carbon atoms, linear or branched alkenyl groups having 2 to 10 carbon atoms, linear or branched alkenyloxy groups having 2 to 10 carbon atoms, linear or branched alkynyl groups having 2 to 10 carbon atoms, linear or branched alkynyloxy groups having 2 to 10 carbon atoms, cycloalkyl groups having 3 to 10 carbon atoms, cycloalkoxy groups having 3 to 10 carbon atoms, cycloalkenyl groups having 3 to 10 carbon atoms, cycloalkenyloxy groups having 3 to 10 carbon atoms, aryl groups having 6 to 10 carbon atoms, and aryloxy groups having 6 to 10 carbon atoms, where the organic group may contain a fluorine atom, an oxygen atom, or an unsaturated bond.

Incidentally, the "case of the organic group containing a fluorine atom" specifically means, for example, that a hydrogen atom in the group is substituted with a fluorine atom.

In addition, the "case of the organic group containing an oxygen atom" specifically means, for example, that "—O—" (ether bond) is interposed between the carbon atoms in the group.

$M^{p+}$ is a proton, a metal cation, or an onium cation; and p is the valence of the cation.]

In addition, a metal salt other the above-mentioned solutes (lithium salts and sodium salts) may be used as an additive. Examples of the metal salt include carboxylic acid salts, such as lithium acrylate, sodium acrylate, lithium methacrylate, and sodium methacrylate; and sulfuric acid ester salts, such as lithium methyl sulfate, sodium methyl sulfate, lithium ethyl sulfate, and sodium ethyl sulfate.

In addition, the electrolyte solution for a non-aqueous-electrolyte solution battery can also be used in a state quasi-solidified with a gelling agent or a cross-linking polymer as in the case of a non-aqueous electrolyte solution battery called a lithium polymer battery.

3. Non-Aqueous-Electrolyte Solution Battery

The non-aqueous-electrolyte solution battery of the present invention at least includes (i) the above-described electrolyte solution for a non-aqueous-electrolyte solution battery, (ii) a positive electrode, and (iii) a negative electrode including at least one selected from the group consisting of negative electrode materials containing lithium metal and negative electrode materials capable of occluding and releasing lithium, sodium, potassium, or magnesium. The non-aqueous electrolyte solution battery preferably further includes, for example, (iv) a separator and an outer case.

Positive Electrode (ii)

The positive electrode (ii) preferably includes at least one oxide and/or a polyanion compound as the positive electrode active material.

Positive Electrode Active Material

In a lithium ion secondary battery in which the main cation in the non-aqueous electrolyte solution is lithium, the positive electrode active material constituting the positive electrode (ii) is not particularly limited so long as it can be charged and discharged. Examples thereof include those containing at least one selected from (A) a lithium-transition metal composite oxide containing at least one metal selected from nickel, manganese, and cobalt and having a layered structure, (B) a lithium-manganese composite oxide having a spinel structure, (C) a lithium-containing olivine type phosphate, and (D) a lithium-rich layered transition metal oxide having a layered rock salt type structure.

(A) Lithium-Transition Metal Composite Oxide

Examples of the positive electrode active material (A): the lithium-transition metal composite oxide containing at least one metal selected from nickel, manganese, and cobalt and having a layered structure, include a lithium-cobalt composite oxide, a lithium-nickel composite oxide, a lithium-nickel-cobalt composite oxide, a lithium-nickel-cobalt-aluminum composite oxide, a lithium-cobalt-manganese composite oxide, a lithium-nickel-manganese composite oxide, and a lithium-nickel-manganese-cobalt composite oxide. In addition, those obtained by substituting a part of the transition metal atoms that are the main components of these lithium-transition metal composite oxides with other elements, such as Al, Ti, V, Cr, Fe, Cu, Zn, Mg, Ga, Zr, Si, B, Ba, Y, and Sn, may be used.

As the lithium-cobalt composite oxide or the lithium-nickel composite oxide, specifically, for example, $LiCoO_2$, $LiNiO_2$, lithium cobaltate doped with different elements such as Mg, Zr, Al, or Ti (e.g., $LiC_{0.98}Mg_{0.01}Zr_{0.01}O_2$, $LiCo_{0.98}Mg_{0.01}Al_{0.01}O_2$, or $LiCo_{0.975}Mg_{0.01}Zr_{0.005}Al_{0.01}O_2$), or lithium cobaltate with a rare earth compound fixed on the surface as described in WO 2014/034043 may be used. As described in JP-A-2002-151077, $LiCoO_2$ particle powder having particle surfaces partially coated with aluminum oxide may be also used.

The lithium-nickel-cobalt composite oxide and the lithium-nickel-cobalt-aluminum composite oxide are represented by formula [1-1]:

$$Li_aNi_{1-b-c}Co_bM^1_cO_2 \qquad [1\text{-}1]$$

In formula [1-1], $M^1$ is at least one element selected from the group consisting of Al, Fe, Mg, Zr, Ti and B; a is $0.9 \leq a \leq 1.2$; and b and c satisfy $0.1 \leq b \leq 0.3$ and $0 \leq c \leq 0.1$.

These composite oxides can be prepared in accordance with, for example, the manufacturing method described in JP-A-2009-137834. Specifically, examples of the composite oxides include $LiNi_{0.8}Co_{0.2}O_2$, $LiNi_{0.8}Co_{0.10}Al_{0.05}O_2$, $LiNi_{0.87}Co_{0.10}Al_{0.03}O_2$, and $LiNi_{0.6}Co_{0.3}Al_{0.1}O_2$.

Examples of the lithium-cobalt-manganese composite oxide and the lithium-nickel-manganese composite oxide include $LiNi_{0.5}Mn_{0.5}O_2$ and $LiCo_{0.5}Mn_{0.5}O_2$.

Examples of the lithium-nickel-manganese-cobalt composite oxide include lithium-containing composite oxides represented by formula [1-2]:

$$Li_dNi_eMn_fCo_gM^2_hO_2 \qquad [1\text{-}2]$$

In formula [1-2], $M^2$ is at least one element selected from the group consisting of Al, Fe, Mg, Zr, Ti, B and Sn; d is $0.9 \leq d \leq 1.2$; and e, f, g, and h satisfy $e+f+g+h=1$, $0 \leq e \leq 0.8$, $0 \leq f \leq 0.5$, $0 \leq g \leq 0.5$, and $h \geq 0$.

The lithium-nickel-manganese-cobalt composite oxide preferably contains manganese within the range shown in formula [1-2] for increasing the structural stability and improving the safetyresultant of the lithium secondary battery at high temperature and more preferably further contains cobalt within the range shown in formula [1-2] for particularly increasing the high efficiency properties of the lithium ion secondary battery.

Specifically, examples of the lithium-nickel-manganese-cobalt composite oxide include $Li[Ni_{1/3}Mn_{1/3}Co_{1/3}]O_2$, $Li[Ni_{0.45}Mn_{0.35}Co_{0.2}]O_2$, $Li[Ni_{0.5}Mn_{0.3}Co_{0.2}]O_2$, $Li[Ni_{0.6}Mn_{0.2}Co_{0.2}]O_2$, $Li[Ni_{0.49}Mn_{0.3}Co_{0.2}Zr_{0.01}]O_2$, and $Li[Ni_{0.49}Mn_{0.3}Co_{0.2}Mg_{0.01}]O_2$ that have a charge-discharge region of 4.3 V or more.

(B) Lithium-Manganese Composite Oxide Having Spinel Structure

Examples of the positive electrode active material (B): the lithium-manganese composite oxide having a spinel structure, include spinel lithium-manganese composite oxides represented by formula [1-3]:

$$Li_j(Mn_{2-k}M^3_k)O_4 \qquad [1\text{-}3]$$

In formula [1-3], $M^3$ is at least one metal element selected from the group consisting of Ni, Co, Fe, Mg, Cr, Cu, Al, and Ti; j is $1.05 \leq j \leq 1.15$; and k is $0 \leq k \leq 0.20$.

Specifically, examples of the lithium-manganese composite oxide include $LiMn_2O_4$, $LiMn_{1.95}Al_{0.05}O_4$, $LiMn_{1.9}Al_{0.1}O_4$, $LiMn_{1.9}Ni_{0.1}O_4$, and $LiMn_{1.5}Ni_{0.5}O_4$.

(C) Lithium-Containing Olivine Type Phosphate

Examples of the positive electrode active material (C): the lithium-containing olivine type phosphate, include those represented by formula [1-4]:

$$LiFe_{1-n}M^4_nPO_4 \qquad [1\text{-}4]$$

In formula [1-4], $M^4$ is at least one selected from Co, Ni, Mn, Cu, Zn, Nb, Mg, Al, Ti, W, Zr, and Cd; and n is $0 \leq n \leq 1$.

Specifically, examples of the lithium-containing olivine type phosphate include $LiFePO_4$, $LiCoPO_4$, $LiNiPO_4$, and $LiMnPO_4$, and in particular, $LiFePO_4$ and/or $LiMnPO_4$ is preferred.

(D) Lithium-Rich Layered Transition Metal Oxide

Examples of the positive electrode active material (D): the lithium-rich layered transition metal oxide having a layered rock salt type structure, include those represented by formula [1-5]:

$$x\ LiM^5O_2 \cdot (1-x)Li_2M^6O_3 \quad [1\text{-}5]$$

In formula [1-5], x is a number satisfying $0<x<1$; $M^5$ is at least one metal element having an average oxidation number of +3; and $M^6$ is at least one metal element having an average oxidation number of +4. In formula [1-5], $M^5$ is preferably one trivalent metal element selected from Mn, Ni, Co, Fe, V, and Cr and may be composed of equal amounts of divalent and tetravalent metals and having an average oxidation number of +3.

In addition, in formula [1-5], $M^6$ is preferably at least one metal element selected from Mn, Zr, and Ti. Specifically, examples of the lithium-rich layered transition metal oxide include $$0.5[LiNi_{0.5}Mn_{0.5}O_2] \cdot 0.5[Li_2MnO_3],$$

$$0.5[LiN_{1/3}Co_{1/3}Mn_{1/3}O_2] \cdot 0.5[Li_2MnO_3],$$

$$0.5[LiNi_{0.375}Co_{0.25}Mn_{0.375}O_2] \cdot 0.5[Li_2MnO_3],$$

$$0.5[LiNi_{0.375}Co_{0.125}Fe_{0.125}Mn_{0.375}O_2] \cdot 0.5[Li_2MnO_3],\text{ and}$$

$$0.45[LiNi_{0.375}Co_{0.25}Mn_{0.375}O_2] \cdot 0.10[Li_2TiO_3] \cdot 0.45[Li_2MnO_3].$$

The positive electrode active material (D) represented by formula [1-5] is known to show a high capacity when charged at a high voltage of 4.4 V (based on Li) or more (for example, U.S. Pat. No. 7,135,252).

These positive electrode active materials can be prepared in accordance with the manufacturing method described in, for example, JP-A-2008-270201, WO 2013/118661, or JP-A-2013-030284.

The positive electrode active material may include at least one selected from the above compounds (A) to (D) as the main component, and examples of other components to be included include transition element chalcogenide, such as $FeS_2$, $TiS_2$, $TiO_2$, $V_2O_5$, $MoO_3$, and $MoS_2$; conductive polymers, such as polyacetylene, polyparaphenylene, polyaniline, and polypyrrole; activated carbon; polymers generating radicals; and carbon materials.

Positive Electrode Current Collector

The positive electrode (ii) includes a positive electrode current collector. As the positive electrode current collector, for example, aluminum, stainless steel, nickel, titanium, or an alloy thereof can be used.

Positive electrode active material layer In the positive electrode (ii), for example, a positive electrode active material layer is formed on at least one surface of the positive electrode current collector. The positive electrode active material layer is composed of, for example, the above-mentioned positive electrode active material, a binder, and, as needed, a conductive agent.

Examples of the binder include polytetrafluoroethylene, polyvinylidene fluoride, a tetrafluoroethylene-perfluoroalkyl vinyl ether copolymer, styrene-butadiene rubber (SBR), carboxymethyl cellulose, methyl cellulose, acetate phthalate cellulose, hydroxypropyl methyl cellulose, and polyvinyl alcohol.

As the conductive agent, for example, carbon materials, such as acetylene black, Ketjen black, furnace black, carbon fiber, graphite (granular graphite and flaky graphite), and fluorinated graphite, can be used. In the positive electrode, acetylene black and Ketjen black having low crystallinity are preferred.

Negative Electrode (iii)

The negative electrode material is not particularly limited, and in a lithium battery and a lithium ion battery, for example, lithium metal, an alloy or an intermetallic compound of lithium metal and another metal, a variety of carbon materials (artificial graphite, natural graphite, etc.), a metal oxide, a metal nitride, tin (simple substance), a tin compound, silicon (simple substance), a silicon compound, activated carbon, and a conductive polymer are used.

The carbon materials are, for example, easily graphitizable carbon, hardly graphitizable carbon (hard carbon) having an interplanar distance between the (002) planes of 0.37 nm or more, and graphite having an interplanar distance between the (002) planes of 0.34 nm or less. More specifically, the carbon materials are, for example, pyrolytic carbons, cokes, glassy carbon fibers, organic polymer compound fired products, activated carbon, and carbon blacks. Among these materials, the cokes include pitch coke, needle coke, and petroleum coke. The organic polymer compound fired product is a product obtained by firing and carbonizing, for example, a phenolic resin or a furan resin at an appropriate temperature. Since the carbon materials hardly change the crystal structure by occlusion and release of lithium, a higher energy density and also excellent cycle properties are preferably obtained. Incidentally, the shape of the carbon material may be any of fibrous, spherical, granular, and flaky shapes. In addition, amorphous carbon and a graphite material having a surface coated with amorphous carbon are more preferable because the reactivity between the material surface and the electrolyte solution is lowered.

The negative electrode (iii) preferably includes at least one negative electrode active material.

Negative Electrode Active Material

In a lithium ion secondary battery in which the main cation in the non-aqueous electrolyte solution is lithium, the negative electrode active material constituting the negative electrode (iii) is a material that can dope and dedope lithium ions, and examples thereof include those containing at least one selected from (E) carbon materials having a lattice plane ((002) plane) d value of 0.340 nm or less determined by X-ray diffraction; (F) carbon materials having a lattice plane ((002) plane) d value of higher than 0.340 nm determined by X-ray diffraction; (G) oxides of one or more metals selected from Si, Sn, and Al; (H) one or more metals selected from Si, Sn, and Al, alloys containing these metals, or alloys of these metals or alloys with lithium; and (I) lithium titanium oxides. These negative electrode active materials can be used alone or in combination of two or more thereof.

(E) Carbon Material Having a Lattice Plane ((002) Plane) d Value of 0.340 nm or Less Determined by X-Ray Diffraction Examples of the negative electrode active material (E): the carbon material having a lattice plane ((002) plane) d value of 0.340 nm or less determined by X-ray diffraction, include pyrolytic carbons, cokes (such as pitch coke, needle coke, and petroleum coke), graphites, organic polymer compound fired products (e.g., products obtained by firing and carbonizing, for example, a phenolic resin or a furan resin at an appropriate temperature), carbon fibers, and activated carbon; and those obtained by graphitization thereof. The carbon material is one having an interplanar distance between the (002) planes (d002) of 0.340 nm or less measured by an X-ray diffraction method, and especially the carbon material is preferably graphite having a true density of 1.70 g/cm³ or more or a highly crystalline carbon material having properties similar to those of the graphite.

(F) Carbon Material Having a Lattice Plane ((002) Plane) d Value of Higher than 0.340 Nm Determined by X-Ray Diffraction Examples of the negative electrode active material (F): the carbon material having a lattice plane ((002) plane) d value of higher than 0.340 nm determined by X-ray diffraction, include amorphous carbon, which is a carbon material hardly changing the stacking order even when heat-treated at a high temperature of 2000° C. or more. Examples thereof include hardly graphitizable carbon (hard carbon), meso-carbon microbeads (MCMB) fired at 1500° C. or less, and meso-phase pitch carbon fibers (MCF).

(G) Oxide of One or More Metals Selected from Si, Sn, and Al

Examples of the negative electrode active material (G): the oxide of one or more metals selected from Si, Sn, and Al, include oxides that can dope and dedope lithium ions, such as silicon oxide and tin oxide.

For example, $SiO_x$ having a structure in which ultrafine particles of Si are dispersed in $SiO_2$ is known. If this material is used as the negative electrode active material, Si reacting with Li is in an ultrafine particle form and accordingly, charge and discharge are smoothly performed. On the other hand, the surface area of the $SiO_x$ particle itself having the above structure is small. Therefore, when it is used as a composition (paste) for forming a negative electrode active material layer, the coating properties and the adhesive properties of the negative electrode mixture layer to the current collector are satisfactory.

Incidentally, since $SiO_x$ significantly changes the volume by charge and discharge, both an increase in the capacity and good charge and discharge cycle properties can be achieved by using SiO together with the above-described graphite as the negative electrode active material (E) at a specific ratio as the negative electrode active material.

(H) One or More Metals Selected from Si, Sn, and Al, Alloys Containing these Metals, or Alloys of these Metals or Alloys with Lithium Examples of the negative electrode active material (H): one or more metals selected from Si, Sn, and Al, alloys containing these metals, or alloys of these metals or alloys with lithium, include metals, such as silicon, tin, and aluminum, silicon alloys, tin alloys, and aluminum alloys, and materials obtained from these metals and alloys by alloying with lithium by charge and discharge can also be used.

Preferred examples include those described in, for example, WO 2004/100293 or JP-A-2008-016424, e.g., metal simple substances, such as silicon (Si) and tin (Sn), (for example, in powder form); the metal alloys; compounds containing the metals; and alloys containing the metals and tin (Sn) and cobalt (Co). The use of such a metal in the electrode can realize a high charge capacity and causes relatively small expansion and contraction of the volume associated with charge and discharge and is therefore preferred. In addition, it is known that when these metals are used in the negative electrode of a lithium ion secondary battery, the metals are alloyed with Li during charging to show a high charge capacity, and the use of such a metal is also preferred on this point.

Furthermore, for example, a negative electrode active material formed of submicron-diameter pillars of silicon or a negative electrode active material formed of fibers of silicon described in, for example, WO 2004/042851 or WO 2007/083155 may be used.

(I) Lithium Titanium Oxide

Examples of the negative electrode active material (I): the lithium titanium oxide, include lithium titanate having a spinel structure and lithium titanate having a ramsdellite structure.

Examples of the lithium titanate having a spinel structure include $Li_{4+\alpha}Ti_5O_{12}$ (α changes within a range of 0≤α≤3 according to the charge and discharge reaction). Examples of the lithium titanate having a ramsdellite structure include $Li_{2+\beta}Ti_3O_7$ (β changes within a range of 0≤β≤3 according to the charge and discharge reaction). These negative electrode active materials can be prepared in accordance with the manufacturing method described in, for example, JP-A-2007-018883 or 2009-176752.

For example, in case of a sodium ion secondary battery in which the main cation in the non-aqueous electrolyte solution is sodium, as the negative electrode active material, hard carbon or an oxide, such as $TiO_2$, $V_2O_5$, or $MoO_3$, is used. For example, in case of a sodium ion secondary battery in which the main cation in the non-aqueous electrolyte solution is sodium, as the positive electrode active material, a sodium-containing transition metal composite oxide, such as $NaFeO_2$, $NaCrO_2$, $NaNiO_2$, $NaMnO_2$, or $NaCoO_2$; those in which the transition metals, such as Fe, Cr, Ni, Mn, and Co, of the sodium-containing transition metal composite oxides are mixtures thereof; those in which the transition metals of the sodium-containing transition metal composite oxides are partially substituted by metals other than transition metals; a phosphate compound of a transition metal, such as $Na_2FeP_2O_7$ or $NaCo_3(PO_4)_2P_2O_7$; a sulfide such as $TiS_2$ or $FeS_2$; a conductive polymer such as polyacetylene, polyparaphenylene, polyaniline, or polypyrrole; activated carbon; a polymer generating radicals; or a carbon material is used.

Negative Electrode Current Collector

The negative electrode (iii) includes a negative electrode current collector. As the negative electrode current collector, for example, copper, stainless steel, nickel, or titanium, or an alloy thereof can be used.

Negative Electrode Active Material Layer

In the negative electrode (iii), for example, a negative electrode active material layer is formed on at least one surface of the negative electrode current collector. The negative electrode active material layer is composed of, for example, the above-mentioned negative electrode active material, a binder, and, as needed, a conductive agent.

Examples of the binder include polytetrafluoroethylene, polyvinylidene fluoride, a tetrafluoroethylene-perfluoroalkyl vinyl ether copolymer, styrene-butadiene rubber (SBR), carboxymethyl cellulose, methyl cellulose, acetate phthalate cellulose, hydroxypropyl methyl cellulose, and polyvinyl alcohol.

As the conductive agent, for example, carbon materials, such as acetylene black, Ketjen black, furnace black, carbon fiber, graphite (granular graphite and flaky graphite), and fluorinated graphite, can be used.

Method for Manufacturing Electrodes (Positive Electrode (ii) and Negative Electrode (iii))

An electrode can be obtained by, for example, dispersing and kneading an active material, a binder, and, as needed, a conductive agent at predetermined amounts in a solvent such as N-methyl-2-pyrrolidone (NMP) or water, applying the resultant paste to a current collector, and drying it to form an active material layer. The resultant electrode is preferably compressed by a method such as roll pressing to adjust the density of the electrode to an appropriate level.

Separator (iv)

The above non-aqueous-electrolyte solution battery can include a separator (iv). As a separator for preventing contact between the positive electrode (ii) and the negative electrode (iii), a polyolefin, such as polypropylene or polyethylene, cellulose, paper, a non-woven fabric made of, for example, glass fibers, or a porous sheet is used. These films are preferably microporous so that the electrolyte solution can permeate, and ions can easily pass therethrough.

An example of the polyolefin separator is a microporous polymer film, such as a porous polyolefin film, that electrically insulates the positive electrode and the negative electrode from each other and allows lithium ions to pass therethrough. Specifically, as the porous polyolefin film, for example, a porous polyethylene film may be used alone, or a multilayer film in which a porous polyethylene film and a porous polypropylene film are stacked may be used. In addition, a composite film of porous polyethylene film and polypropylene film is can be also exemplified.

Outer Case

In constructing a non-aqueous-electrolyte solution battery, as the outer case of the non-aqueous-electrolyte solution battery, for example, a metal can in, for example, a coin, cylinder, or square shape or a laminated outer case can be used. Examples of the material of the metal can include nickel-plated steel, stainless steel, nickel-plated stainless steel, aluminum or an alloy thereof, nickel, and titanium.

As the laminated outer case, for example, an aluminum laminate film, an SUS-made laminate film, or a laminate film of a silica-coated, for example, polypropylene or polyethylene can be used.

The structure of the non-aqueous-electrolyte solution battery according to the present embodiment is not particularly limited. For example, the structure can be such that an electrode element in which a positive electrode and a negative electrode are disposed opposite to each other and a non-aqueous electrolyte solution are contained in an outer case. The shape of the non-aqueous-electrolyte solution battery is not particularly limited. An electrochemical device having a coin, cylinder, or square shape or a shape such as an aluminum laminate sheet is assembled from the above-mentioned elements.

EXAMPLES

The present invention will now be specifically described below by way of examples, but the scope of the present invention is not limited by the examples.

Lithium Ion Battery

Example 1C-1

Preparation of Electrolyte Solution

Electrolyte solution No. (1C-1)-1-(0) for a non-aqueous electrolyte solution battery was prepared by using a mixed solvent of ethylene carbonate, dimethyl carbonate, and ethyl methyl carbonate at a volume ratio of 3:3:4 as a non-aqueous solvent and dissolving $LiPF_6$ as a solute and Compound (1C-1) as the above imine compound in the solvent, such that the concentration of $LiPF_6$ was 1.0 mol/L and that the concentration of Compound (1C-1) (the content of Cl and the content of free acids in the imine compound as a raw material before being dissolved in the electrolyte solution were 10 mass ppm and 60 mass ppm, respectively) was 1.0 mass % based on the total amount of the non-aqueous solvent, the solute, and the imine compound. The above preparation was performed while maintaining the solution temperature within a range of 20° C. to 30° C. The conditions for preparing the non-aqueous electrolyte solution are shown in Table 1.

Production of Battery

A battery was produced by using the above electrolyte solution, $LiNi_{0.6}Co_{0.2}Mn_{0.2}O_2$ as the positive electrode material, and graphite as the negative electrode material, and the initial gas generation amount and the high-temperature storage properties of the battery were actually evaluated. The battery for the test was produced as follows.

A $LiNi_{0.6}Co_{0.2}Mn_{0.2}O_2$ powder (90 mass %) was mixed with polyvinylidene fluoride (hereinafter referred to as "PVDF", 5 mass %) as a binder and acetylene black (5 mass %) as a conductive material, and N-methylpyrrolidone (hereinafter referred to as "NMP") was further added to the mixture to make a paste. This paste was applied onto aluminum foil and was dried to form a positive electrode body for a test.

In addition, a graphite powder (90 mass %) was mixed with PVDF (10 mass %) as a binder, and NMP was further added to the mixture to form a slurry. The slurry was applied onto copper foil and was dried at 120° C. for 12 hours to form a negative electrode body for a test.

A polyethylene separator was impregnated with an electrolyte solution to assemble a 50 mAh battery with an aluminum laminated outer case.

Evaluation of Initial Gas Generation Amount

A charge and discharge test at an environmental temperature of 25° C. was performed using the above battery, and the amount of gas generated at that time was evaluated as the initial gas generation amount. Charge and discharge are both performed at a current density of 0.35 $mA/cm^2$. The charge was performed by maintaining 4.3 V for 1 hour after reaching 4.3 V, and the discharge was performed until 3.0 V. Before and after the charge and discharge, the amount of increase in the battery volume was estimated by a buoyancy method using silicon oil to evaluate the gas generation amount.

Evaluation of High-Temperature Storage Properties (70° C. Durability Performance)

After the above charge and discharge, the battery was charged again until 4.3 V at a current density of 0.35 $mA/cm^2$ and was stored at an environmental temperature of 70° C. for 10 days. The battery was then discharged until 3.0 V at an environmental temperature of 25° C. at a current density of 0.35 $mA/cm^2$, and the discharge capacity was comparatively evaluated.

The results of evaluation of batteries are shown in Table 2. Incidentally, the values of the gas generation amount and 70° C. durability performance of the batteries in Table 2 are relative values when the gas generation amount after initial charge and discharge and the discharge capacity after a 70° C. storage test of a laminated battery produced using the electrolyte solution No. (0)-(0) described below were each defined as 100.

Examples 1C-2 to 4C-2 and Comparative Examples 1-1 to 1-3

Electrolyte solutions were each prepared in the same manner as that in Electrolyte solution No. (1C-1)-1-(0) except that the type of the imine compound was changed as shown in Table 1. Incidentally, in the imine compounds used in the subsequent examples, the contents of Cl were all 200 mass ppm or less, and the contents of free acids were all 150 mass ppm or less.

In addition, Electrolyte solution No. (0)-(0) was prepared in the same manner as that in Electrolyte solution No. (1C-1)-1-(0) except that the imine compound was not added thereto.

In addition, Electrolyte solution No. (0)-(VC)-1 was prepared in the same manner as that in Electrolyte solution No. (1C-1)-1-(0) except that the imine compound was not added thereto and vinylene carbonate (hereinafter, referred to as "VC") was added instead.

In addition, Electrolyte solution No. (0)-(13PRS)-1 was prepared in the same manner as that in Electrolyte solution No. (1C-1)-1-(0) except that the imine compound was not added thereto and 1,3-propenesultone (hereinafter, referred to as "13PRS") was added instead.

The resultant electrolyte solutions were evaluated as in Example 1C-1. The results of the evaluation are shown in Table 2.

TABLE 1

| Electrolyte solution No. | Imine compound | | Solute | | Other solute and additive | |
|---|---|---|---|---|---|---|
| | Type | Concentration [mass %] | Type | Concentration [mol/L] | Type | Concentration [mass %] |
| (1C-1)-1-(0) | (1C-1) | 1 | LiPF$_6$ | 1 | — | — |
| (1C-2)-1-(0) | (1C-2) | 1 | LiPF$_6$ | 1 | — | — |
| (1C-4)-1-(0) | (1C-4) | 1 | LiPF$_6$ | 1 | — | — |
| (1C-5)-1-(0) | (1C-5) | 1 | LiPF$_6$ | 1 | — | — |
| (1C-6)-1-(0) | (1C-6) | 1 | LiPF$_6$ | 1 | — | — |
| (1C-7)-1-(0) | (1C-7) | 1 | LiPF$_6$ | 1 | — | — |
| (1C-9)-1-(0) | (1C-9) | 1 | LiPF$_6$ | 1 | — | — |
| (1C-11)-1-(0) | (1C-11) | 1 | LiPF$_6$ | 1 | — | — |
| (1C-13)-1-(0) | (1C-13) | 1 | LiPF$_6$ | 1 | — | — |
| (1S-2)-1-(0) | (1S-2) | 1 | LiPF$_6$ | 1 | — | — |
| (1S-3)-1-(0) | (1S-3) | 1 | LiPF$_6$ | 1 | — | — |
| (1S-4)-1-(0) | (1S-4) | 1 | LiPF$_6$ | 1 | — | — |
| (1S-5)-1-(0) | (1S-5) | 1 | LiPF$_6$ | 1 | — | — |
| (1S-9)-1-(0) | (1S-9) | 1 | LiPF$_6$ | 1 | — | — |
| (2C-1)-1-(0) | (2C-1) | 1 | LiPF$_6$ | 1 | — | — |
| (2C-2)-1-(0) | (2C-2) | 1 | LiPF$_6$ | 1 | — | — |
| (2C-4)-1-(0) | (2C-4) | 1 | LiPF$_6$ | 1 | — | — |
| (3C-1)-1-(0) | (3C-1) | 1 | LiPF$_6$ | 1 | — | — |
| (3C-6)-1-(0) | (3C-6) | 1 | LiPF$_6$ | 1 | — | — |
| (3C-9)-1-(0) | (3C-9) | 1 | LiPF$_6$ | 1 | — | — |
| (3C-11)-1-(0) | (3C-11) | 1 | LiPF$_6$ | 1 | — | — |
| (3S-1)-1-(0) | (3S-1) | 1 | LiPF$_6$ | 1 | — | — |
| (3S-2)-1-(0) | (3S-2) | 1 | LiPF$_6$ | 1 | — | — |
| (4C-2)-1-(0) | (4C-2) | 1 | LiPF$_6$ | 1 | — | — |
| (0)-(0) | — | — | LiPF$_6$ | 1 | — | — |
| (0)-(VC)-1 | — | — | LiPF$_6$ | 1 | VC | 1 |
| (0)-(13PRS)-1 | — | — | LiPF$_6$ | 1 | 13PRS | 1 |

TABLE 2

| | Electrolyte solution No. | Positive electrode active material | Negative electrode active material | Initial gas amount* [%] | Capacity after storage* [%] |
|---|---|---|---|---|---|
| Example 1C-1 | (1C-1)-1-(0) | LiNi$_{0.6}$Co$_{0.2}$Mn$_{0.2}$O$_2$ | Graphite | 72 | 112 |
| Example 1C-2 | (1C-2)-1-(0) | | | 83 | 104 |
| Example 1C-4 | (1C-4)-1-(0) | | | 70 | 109 |
| Example 1C-5 | (1C-5)-1-(0) | | | 75 | 106 |
| Example 1C-6 | (1C-6)-1-(0) | | | 71 | 107 |
| Example 1C-7 | (1C-7)-1-(0) | | | 70 | 107 |
| Example 1C-9 | (1C-9)-1-(0) | | | 71 | 110 |
| Example 1C-11 | (1C-11)-1-(0) | | | 70 | 109 |
| Example 1C-13 | (1C-13)-1-(0) | | | 72 | 110 |
| Example 1S-2 | (1S-2)-1-(0) | | | 75 | 111 |
| Example 1S-3 | (1S-3)-1-(0) | | | 83 | 110 |
| Example 1S-4 | (1S-4)-1-(0) | | | 70 | 104 |
| Example 1S-5 | (1S-5)-1-(0) | | | 72 | 104 |
| Example 1S-9 | (1S-9)-1-(0) | | | 81 | 107 |
| Example 2C-1 | (2C-1)-1-(0) | | | 75 | 108 |
| Example 2C-2 | (2C-2)-1-(0) | | | 75 | 107 |
| Example 2C-4 | (2C-4)-1-(0) | | | 75 | 107 |
| Example 3C-1 | (3C-1)-1-(0) | | | 76 | 105 |
| Example 3C-6 | (3C-6)-1-(0) | | | 72 | 114 |
| Example 3C-9 | (3C-9)-1-(0) | | | 70 | 103 |
| Example 3C-11 | (3C-11)-1-(0) | | | 78 | 105 |
| Example 3S-1 | (3S-1)-1-(0) | | | 74 | 105 |
| Example 3S-2 | (3S-2)-1-(0) | | | 79 | 103 |

TABLE 2-continued

|  | Electrolyte solution No. | Positive electrode active material | Negative electrode active material | Initial gas amount* [%] | Capacity after storage* [%] |
|---|---|---|---|---|---|
| Example 4C-2 | (4C-2)-1-(0) | | | 80 | 105 |
| Comparative Example 1-1 | (0)-(0) | | | 100 | 100 |
| Comparative Example 1-2 | (0)-(VC)-1 | | | 87 | 105 |
| Comparative Example 1-3 | (0)-(13PRS)-1 | | | 90 | 104 |

*Relative values when the result of evaluation of electrolyte solution No. (0)-(0) was defined as 100.

It was confirmed that, when the electrolyte solution having the composition containing the imine compound having the specific structure of the present invention is used, the initial gas generation amount can be suppressed, as compared with Comparative Examples 1-2 and 1-3 using the conventional electrolyte solutions having the composition containing vinylene carbonate or unsaturated sultone. In particular, it was confirmed that, when (1C-1), (1C-4), (1C-5), (1C-6), (1C-7), (1C-9), (1C-11), (1C-13), (1S-2), (1S-4), (1S-5), (2C-1), (2C-2), (2C-4), (3C-6), (3C-9), or (3S-1) is used as the imine compound, the effect of suppressing the initial gas generation amount is high.

In addition, the results of evaluation of high-temperature storage properties (70° C. durability performance) are shown in the table for reference, and it was confirmed that in each Example, the initial gas generation amount can be suppressed without significantly impairing the 70° C. durability performance, that is, the suppression of the initial gas generation amount and the 70° C. durability performance can be exhibited in a well-balanced manner.

In particular, it was confirmed that when (1C-1), (1C-4), (1C-6), (1C-7), (1C-9), (1C-11), (1C-13), (1S-2), (1S-3), (1S-9), (2C-1), (2C-2), (2C-4), or (3C-6) is used as the imine compound, the 70° C. durability performance is excellent, in addition to the effect of suppressing the initial gas generation amount.

Examples 1-1 to 1-33 and Comparative Examples 1-1 to 1-17

Electrolyte solutions were each prepared in the same manner as that in Electrolyte solution No. (1C-1)-1-(0) except that the type and the concentration of the imine compound and the concentration of the solute were changed as shown in Tables 3 and 4. The resultant electrolyte solutions were evaluated as in Example 1C-1. The results of the evaluation are shown in Tables 5 and 6.

TABLE 3

| Electrolyte solution No. | Imine compound | | Solute | | Other solute and additive | |
|---|---|---|---|---|---|---|
| | Type | Concentration [mass %] | Type | Concentration [mol/L] | Type | Concentration [mass %] |
| (1C-1)-0.1-(0) | (1C-1) | 0.1 | LiPF$_6$ | 1 | — | — |
| (1C-1)-1-(0) | (1C-1) | 1 | LiPF$_6$ | 1 | — | — |
| (1C-2)-0.01-(0) | (1C-2) | 0.01 | LiPF$_6$ | 1 | — | — |
| (1C-2)-5-(0) | (1C-2) | 5 | LiPF$_6$ | 1 | — | — |
| (1C-2)-5.3-(0) | (1C-2) | 5.3 | LiPF$_6$ | 1 | — | — |
| (1C-4)-0.5-(0) | (1C-4) | 0.5 | LiPF$_6$ | 1 | — | — |
| (1C-4)-1-(0) | (1C-4) | 1 | LiPF$_6$ | 1 | — | — |
| (1C-5)-1-(0) | (1C-5) | 1 | LiPF$_6$ | 1 | — | — |
| (1C-6)-1-(0) | (1C-6) | 1 | LiPF$_6$ | 1 | — | — |
| (1C-7)-0.001-(0) | (1C-7) | 0.001 | LiPF$_6$ | 1 | — | — |
| (1C-7)-1-(0) | (1C-7) | 1 | LiPF$_6$ | 1 | — | — |
| (1C-9)-1-(0) | (1C-9) | 1 | LiPF$_6$ | 1 | — | — |
| (1C-11)-0.01-(0) | (1C-11) | 0.01 | LiPF$_6$ | 1 | — | — |
| (1C-11)-0.1-(0) | (1C-11) | 0.1 | LiPF$_6$ | 1 | — | — |
| (1C-13)-0.5-(0) | (1C-13) | 0.5 | LiPF$_6$ | 1 | — | — |
| (1C-1 3)-1-(0) | (1C-13) | 1 | LiPF$_6$ | 1 | — | — |
| (0)-(0) | — | — | LiPF$_6$ | 1 | — | — |
| (0)-(VC)-1 | — | — | LiPF$_6$ | 1 | VC | 1 |
| (0)-(13PRS)-1 | — | — | LiPF$_6$ | 1 | 13PRS | 1 |
| (0)-(VC)-0.001 | — | — | LiPF$_6$ | 1 | VC | 0.001 |
| (0)-(13PRS)-0.001 | — | — | LiPF$_6$ | 1 | 13PRS | 0.001 |
| (0)-(VC)-0.01 | — | — | LiPF$_6$ | 1 | VC | 0.01 |
| (0)-(13PRS)-0.01 | — | — | LiPF$_6$ | 1 | 13PRS | 0.01 |
| (0)-(VC)-0.1 | — | — | LiPF$_6$ | 1 | VC | 0.1 |
| (0)-(13PRS)-0.1 | — | — | LiPF$_6$ | 1 | 13PRS | 0.1 |
| (0)-(VC)-0.2 | — | — | LiPF$_6$ | 1 | VC | 0.2 |
| (0)-(13PRS)-0.2 | — | — | LiPF$_6$ | 1 | 13PRS | 0.2 |
| (0)-(VC)-0.5 | — | — | LiPF$_6$ | 1 | VC | 0.5 |
| (0)-(13PRS)-0.5 | — | — | LiPF$_6$ | 1 | 13PRS | 0.5 |
| (0)-(VC)-5 | — | — | LiPF$_6$ | 1 | VC | 5 |
| (0)-(13PRS)-5 | — | — | LiPF$_6$ | 1 | 13PRS | 5 |

TABLE 3-continued

| Electrolyte solution No. | Imine compound Type | Imine compound Concentration [mass %] | Solute Type | Solute Concentration [mol/L] | Other solute and additive Type | Other solute and additive Concentration [mass %] |
|---|---|---|---|---|---|---|
| (0)-(VC)-5.3 | — | — | LiPF$_6$ | 1 | VC | 5.3 |
| (0)-(13PRS)-5.3 | — | — | LiPF$_6$ | 1 | 13PRS | 5.3 |

TABLE 4

| Electrolyte solution No. | Imine compound Type | Imine compound Concentration [mass%] | Solute Type | Solute Concentration [mol/L] | Other solute and additive Type | Other solute and additive Concentration [mass %] |
|---|---|---|---|---|---|---|
| (1S-2)-0.5-(0) | (1S-2) | 0.5 | LiPF$_6$ | 1 | — | — |
| (1S-2)-1-(0) | (1S-2) | 1 | LiPF$_6$ | 1 | — | — |
| (1S-3)-1-(0)_0.5 | (1S-3) | 1 | LiPF$_6$ | 0.5 | — | — |
| (1S-3)-1-(0)_1.5 | (1S-3) | 1 | LiPF$_6$ | 1.5 | — | — |
| (1S-3)-1-(0)_2.5 | (1S-3) | 1 | LiPF$_6$ | 2.5 | — | — |
| (1S-4)-1-(0) | (1S-4) | 1 | LiPF$_6$ | 1 | — | — |
| (1S-5)-1-(0) | (1S-5) | 1 | LiPF$_6$ | 1 | — | — |
| (1S-9)-1-(0) | (1S-9) | 1 | LiPF$_6$ | 1 | — | — |
| (2C-2)-0.2-(0) | (2C-2) | 0.2 | LiPF$_6$ | 1 | — | — |
| (2C-2)-0.5-(0) | (2C-2) | 0.5 | LiPF$_6$ | 1 | — | — |
| (2C-4)-1-(0) | (2C-4) | 1 | LiPF$_6$ | 1 | — | — |
| (3C-1)-1-(0) | (3C-1) | 1 | LiPF$_6$ | 1 | — | — |
| (3C-6)-1-(0) | (3C-6) | 1 | LiPF$_6$ | 1 | — | — |
| (3C-9)-1-(0) | (3C-9) | 1 | LiPF$_6$ | 1 | — | — |
| (3C-11)-1-(0) | (3C-11) | 1 | LiPF$_6$ | 1 | — | — |
| (3S-1)-1-(0) | (3S-1) | 1 | LiPF$_6$ | 1 | — | — |
| (3S-2)-1-(0) | (3S-2) | 1 | LiPF$_6$ | 1 | — | — |
| (0)-(0) | — | — | LiPF$_6$ | 1 | — | — |
| (0)-(VC)-1 | — | — | LiPF$_6$ | 1 | VC | 1 |
| (0)-(13PRS)-1 | — | — | LiPF$_6$ | 1 | 13PRS | 1 |
| (0)-(VC)-0.001 | — | — | LiPF$_6$ | 1 | VC | 0.001 |
| (0)-(13PRS)-0.001 | — | — | LiPF$_6$ | 1 | 13PRS | 0.001 |
| (0)-(VC)-0.01 | — | — | LiPF$_6$ | 1 | VC | 0.01 |
| (0)-(13PRS)-0.01 | — | — | LiPF$_6$ | 1 | 13PRS | 0.01 |
| (0)-(VC)-0.1 | — | — | LiPF$_6$ | 1 | VC | 0.1 |
| (0)-(13PRS)-0.1 | — | — | LiPF$_6$ | 1 | 13PRS | 0.1 |
| (0)-(VC)-0.2 | — | — | LiPF$_6$ | 1 | VC | 0.2 |
| (0)-(13PRS)-0.2 | — | — | LiPF$_6$ | 1 | 13PRS | 0.2 |
| (0)-(VC)-0.5 | — | — | LiPF$_6$ | 1 | VC | 0.5 |
| (0)-(13PRS)-0.5 | — | — | LiPF$_6$ | 1 | 13PRS | 0.5 |
| (0)-(VC)-5 | — | — | LiPF$_6$ | 1 | VC | 5 |
| (0)-(13PRS)-5 | — | — | LiPF$_6$ | 1 | 13PRS | 5 |
| (0)-(VC)-5.3 | — | — | LiPF$_6$ | 1 | VC | 5.3 |
| (0)-(13PRS)-5.3 | — | — | LiPF$_6$ | 1 | 13PRS | 5.3 |

TABLE 5

| | Electrolyte solution No. | Positive electrode active material | Negative electrode active material | Initial gas amount* [%] | Capacity after storage* [%] |
|---|---|---|---|---|---|
| Example 1-1 | (1C-1)-0.1-(0) | LiNi$_{0.6}$Co$_{0.2}$Mn$_{0.2}$O$_2$ | Graphite | 77 | 106 |
| Example 1-2 | (1C-1)-1-(0) | | | 72 | 112 |
| Example 1-3 | (1C-2)-0.01-(0) | | | 81 | 103 |
| Example 1-4 | (1C-2)-5-(0) | | | 91 | 107 |
| Example 1-5 | (1C-2)-5.3-(0) | | | 94 | 107 |
| Example 1-6 | (1C-4)-0.5-(0) | | | 71 | 110 |
| Example 1-7 | (1C-4)-1-(0) | | | 70 | 109 |
| Example 1-8 | (1C-5)-1-(0) | | | 75 | 106 |
| Example 1-9 | (1C-6)-1-(0) | | | 71 | 107 |
| Example 1-10 | (1C-7)-0.001-(0) | | | 89 | 102 |
| Example 1-11 | (1C-7)-1-(0) | | | 70 | 107 |
| Example 1-12 | (1C-9)-1-(0) | | | 71 | 110 |
| Example 1-13 | (1C-11)-0.01-(0) | | | 81 | 103 |
| Example 1-14 | (1C-11)-0.1-(0) | | | 75 | 105 |

TABLE 5-continued

|  | Electrolyte solution No. | Positive electrode active material | Negative electrode active material | Initial gas amount* [%] | Capacity after storage* [%] |
| --- | --- | --- | --- | --- | --- |
| Example 1-15 | (1C-13)-0.5-(0) |  |  | 88 | 106 |
| Example 1-16 | (1C-13)-1-(0) |  |  | 72 | 110 |
| Comparative Example 1-1 | (0)-(0) |  |  | 100 | 100 |
| Comparative Example 1-2 | (0)-(VC)-1 |  |  | 87 | 105 |
| Comparative Example 1-3 | (0)-(13PRS)-1 |  |  | 90 | 104 |
| Comparative Example 1-4 | (0)-(VC)-0.001 |  |  | 100 | 100 |
| Comparative Example 1-5 | (0)-(13PRS)-0.001 |  |  | 100 | 100 |
| Comparative Example 1-6 | (0)-(VC)-0.01 |  |  | 100 | 100 |
| Comparative Example 1-7 | (0)-(13PRS)-0.01 |  |  | 100 | 100 |
| Comparative Example 1-8 | (0)-(VC)-0.1 |  |  | 99 | 101 |
| Comparative Example 1-9 | (0)-(13PRS)-0.1 |  |  | 99 | 101 |
| Comparative Example 1-10 | (0)-(VC)-0.2 |  |  | 98 | 101 |
| Comparative Example 1-11 | (0)-(13PRS)-0.2 |  |  | 97 | 100 |
| Comparative Example 1-12 | (0)-(VC)-0.5 |  |  | 95 | 103 |
| Comparative Example 1-13 | (0)-(13PRS)-0.5 |  |  | 93 | 101 |
| Comparative Example 1-14 | (0)-(VC)-5 |  |  | 101 | 110 |
| Comparative Example 1-15 | (0)-(13PRS)-5 |  |  | 103 | 105 |
| Comparative Example 1-16 | (0)-(VC)-5.3 |  |  | 103 | 110 |
| Comparative Example 1-17 | (0)-(13PRS)-5.3 |  |  | 104 | 105 |

*Relative values when the result of evaluation of electrolyte solution No. (0)-(0) was defined as 100.

TABLE 6

|  | Electrolyte solution No. | Positive electrode active material | Negative electrode active material | Initial gas amount* [%] | Capacity after storage* [%] |
| --- | --- | --- | --- | --- | --- |
| Example 1-17 | (1S-2)-0.5-(0) | $LiNi_{0.6}Co_{0.2}Mn_{0.2}O_2$ | Graphite | 82 | 106 |
| Example 1-18 | (1S-2)-1-(0) |  |  | 75 | 111 |
| Example 1-19 | (1S-3)-1-(0)-0.5 |  |  | 88 | 102 |
| Example 1-20 | (1S-3)-1-(0)-1.5 |  |  | 79 | 113 |
| Example 1-21 | (1S-3)-1-(0)-2.5 |  |  | 77 | 110 |
| Example 1-22 | (1S-4)-1-(0) |  |  | 70 | 104 |
| Example 1-23 | (1S-5)-1-(0) |  |  | 72 | 104 |
| Example 1-24 | (1S-9)-1-(0) |  |  | 81 | 107 |
| Example 1-25 | (2C-2)-0.2-(0) |  |  | 91 | 105 |
| Example 1-26 | (2C-2)-0.5-(0) |  |  | 80 | 109 |
| Example 1-27 | (2C-4)-1-(0) |  |  | 75 | 107 |
| Example 1-28 | (3C-1)-1-(0) |  |  | 76 | 105 |
| Example 1-29 | (3C-6)-1-(0) |  |  | 72 | 114 |
| Example 1-30 | (3C-9)-1-(0) |  |  | 70 | 103 |
| Example 1-31 | (3C-11)-1-(0) |  |  | 78 | 105 |
| Example 1-32 | (3S-1)-1-(0) |  |  | 74 | 105 |
| Example 1-33 | (3S-2)-1-(0) |  |  | 79 | 103 |
| Comparative Example 1-1 | (0)-(0) |  |  | 100 | 100 |
| Comparative Example 1-2 | (0)-(VC)-1 |  |  | 87 | 105 |
| Comparative Example 1-3 | (0)-(13PRS)-1 |  |  | 90 | 104 |
| Comparative Example 1-4 | (0)-(VC)-0.001 |  |  | 100 | 100 |
| Comparative Example 1-5 | (0)-(13PRS)-0.001 |  |  | 100 | 100 |

TABLE 6-continued

|  | Electrolyte solution No. | Positive electrode active material | Negative electrode active material | Initial gas amount* [%] | Capacity after storage* [%] |
| --- | --- | --- | --- | --- | --- |
| Comparative Example 1-6 | (0)-(VC)-0.01 |  |  | 100 | 100 |
| Comparative Example 1-7 | (0)-(13PRS)-0.01 |  |  | 100 | 100 |
| Comparative Example 1-8 | (0)-(VC)-0.1 |  |  | 99 | 101 |
| Comparative Example 1-9 | (0)-(13PRS)-0.1 |  |  | 99 | 101 |
| Comparative Example 1-10 | (0)-(VC)-0.2 |  |  | 98 | 101 |
| Comparative Example 1-11 | (0)-(13PRS)-0.2 |  |  | 97 | 100 |
| Comparative Example 1-12 | (0)-(VC)-0.5 |  |  | 95 | 103 |
| Comparative Example 1-13 | (0)-(13PRS)-0.5 |  |  | 93 | 101 |
| Comparative Example 1-14 | (0)-(VC)-5 |  |  | 101 | 110 |
| Comparative Example 1-15 | (0)-(13PRS)-5 |  |  | 103 | 105 |
| Comparative Example 1-16 | (0)-(VC)-5.3 |  |  | 103 | 110 |
| Comparative Example 1-17 | (0)-(13PRS)-5.3 |  |  | 104 | 105 |

*Relative values when the result of evaluation of electrolyte solution No. (0)-(0) was defined as 100.

It was confirmed that, even if the type of the imine compound was changed as shown in Tables 3 to 6 (for example, Examples 1-2, 1-7 to 1-9, 1-11, 1-12, 1-16, 1-18, 1-22 to 1-24, and 1-27 to 1-33), the initial gas generation amount can be suppressed, as compared with Comparative Examples (for example, Comparative Examples 1-2 and 1-3) using the conventional electrolyte solutions having the composition containing vinylene carbonate or unsaturated sultone.

In addition, it was confirmed that, even if the concentration of the imine compound and the concentration of the solute were changed, the initial gas generation amount can be suppressed, in the same manner as above.

Also, in all of the Examples shown in Tables 3 and 4, it was verified that the suppression of the initial gas generation amount and the 70° C. durability performance can be exhibited in a well-balanced manner.

Examples and Comparative Examples Using Electrolyte Solutions Having Variously Modified Compositions The electrolyte solutions according to Examples and Comparative Examples shown in Tables 11 to 15 and 17 were each prepared in the same manner as that in Electrolyte solution No. (1C-1)-1-(0), except that the types and the concentrations of the imine compounds and the types and the concentrations of other solutes and additives were variously changed as shown in Tables 7 to 10 and 16.

The resultant electrolyte solutions were evaluated as in the same manner as Example 1C-1, and it was confirmed that the initial gas generation amount can be suppressed also in each Example as shown in Tables 11 to 15 and 17, as compared with the corresponding comparative examples using the conventional electrolyte solutions having the compositions containing vinylene carbonate or unsaturated sultone.

Further, in all of the Examples shown in Tables 11 to 15 and 17, the suppression of the initial gas generation amount and the 70° C. durability performance can be exhibited in a well-balanced manner.

TABLE 7

|  | Imine compound | | Solute | | Other solute and additive | |
| --- | --- | --- | --- | --- | --- | --- |
| Electrolyte solution No. | Type | Conc. [mass %] | Type | Conc. [mol/L] | Type | Conc. [mass %] |
| (1C-1)-0.5-(0) | (1C-1) | 0.5 | $LiPF_6$ | 1 | — | — |
| (0)-(0) | — | — | $LiPF_6$ | 1 | — | — |
| (1C-1)-0.5-(LiPF2(Ox)2)-1 | (1C-1) | 0.5 | $LiPF_6$ | 1 | $LiPF_2(C_2O_4)_2$ | 1 |
| (0)-(VC)-0.5-(LiPF2(Ox)2)-1 | — | — | $LiPF_6$ | 1 | VC, $LiPF_2(C_2O_4)_2$ | 0.5, 1 |
| (0)-(13PRS)-0.5-(LiPF2(Ox)2)-1 | — | — | $LiPF_6$ | 1 | 13PRS, $LiPF_2(C_2O_4)_2$ | 0.5, 1 |
| (1C-1)-0.5-(LiPF4(Ox))-1 | (1C-1) | 0.5 | $LiPF_6$ | 1 | $LiPF_4(C_2O_4)$ | 1 |

TABLE 7-continued

| Electrolyte solution No. | Imine compound Type | Conc. [mass %] | Solute Type | Conc. [mol/L] | Other solute and additive Type | Conc. [mass %] |
|---|---|---|---|---|---|---|
| (0)-(VC)-0.5-(LiPF4(Ox))-1 | — | — | LiPF$_6$ | 1 | VC, LiPF$_4$(C$_2$O$_4$) | 0.5, 1 |
| (0)-(13PRS)-0.5-(LiPF4(Ox))-1 | — | — | LiPF$_6$ | 1 | 13PRS, LiPF$_4$(C$_2$O$_4$) | 0.5, 1 |
| (1C-4)-0.5-(0) | (1C-4) | 0.5 | LiPF$_6$ | 1 | — | — |
| (1C-4)-0.5-(LiPF2(Ox)2)-1 | (1C-4) | 0.5 | LiPF$_6$ | 1 | LiPF$_2$(C$_2$O$_4$)$_2$ | 1 |
| (1C-4)-0.5-(LiPF4(Ox))-1 | (1C-4) | 0.5 | LiPF$_6$ | 1 | LiPF$_4$(C$_2$O$_4$) | 1 |

TABLE 8

| Electrolyte solution No. | Imine compound Type | Conc. [mass %] | Solute Type | Conc. [mol/L] | Other solute and additive Type | Conc. [mass %] |
|---|---|---|---|---|---|---|
| (1C-7)-0.5-(0) | (1C-7) | 0.5 | LiPF$_6$ | 1 | — | — |
| (1C-7)-0.5-(LiPF2(Ox)2)-1 | (1C-7) | 0.5 | LiPF$_6$ | 1 | LiPF$_2$(C$_2$O$_4$)$_2$ | 1 |
| (1C-7)-0.5-(LiPF4(Ox))-1 | (1C-7) | 0.5 | LiPF$_6$ | 1 | LiPF$_4$(C$_2$O$_4$) | 1 |
| (1C-7)-0.5-(LiBF2(Ox))-1 | (1C-7) | 0.5 | LiPF$_6$ | 1 | LiBF$_2$(C$_2$O$_4$) | 1 |
| (0)-(VC)-0.5-(LiBF2(Ox))-1 | — | — | LiPF$_6$ | 1 | VC, LiBF$_2$(C$_2$O$_4$) | 0.5, 1 |
| (0)-(13PRS)-0.5-(LiBF(Ox))-1 | — | — | LiPF$_6$ | 1 | 13PRS, LiBF$_2$(C$_2$O$_4$) | 0.5, 1 |
| (1C-7)-0.5-(LiB(Ox)2)-1 | (1C-7) | 0.5 | LiPF$_6$ | 1 | LiB(C$_2$O$_4$)$_2$ | 1 |
| (0)-(VC)-0.5-(LiB(Ox)2)-1 | — | — | LiPF$_6$ | 1 | VC, LiB(C$_2$O$_4$)$_2$ | 0.5, 1 |
| (0)-(13PRS)-0.5-(LiB(Ox)2)-1 | — | — | LiPF$_6$ | 1 | 13PRS, LiB(C$_2$O$_4$)$_2$ | 0.5, 1 |
| (1C-7)-0.5-(LiPO2F2)-1 | (1C-7) | 0.5 | LiPF$_6$ | 1 | LiPO$_2$F$_2$ | 1 |
| (0)-(VC)-0.5-(LiPO2F2)-1 | — | — | LiPF$_6$ | 1 | VC, LiPO$_2$F$_2$ | 0.5, 1 |
| (0)-(13PRS)-0.5-(LiPO2F2)-1 | — | — | LiPF$_6$ | 1 | 13PRS, LiPO$_2$F$_2$ | 0.5, 1 |
| (1C-7)-0.5-(LiN(POF2)2)-1 | (1C-7) | 0.5 | LiPF$_6$ | 1 | LiN(POF$_2$)$_2$ | 1 |
| (0)-(VC)-0.5-(LiN(POF2)2)-1 | — | — | LiPF$_6$ | 1 | VC, LiN(POF$_2$)$_2$ | 0.5, 1 |
| (0)-(13PRS)-0.5-(LiN(POF2)2)-1 | — | — | LiPF$_6$ | 1 | 13PRS, LiN(POF$_2$)$_2$ | 0.5, 1 |
| (1C-7)-0.5-(LiN(SO2F)2)-1 | (1C-7) | 0.5 | LiPF$_6$ | 1 | LiN(SO$_2$F)$_2$ | 1 |
| (0)-(VC)-0.5-(LiN(SO2F)2)-1 | — | — | LiPF$_6$ | 1 | VC, LiN(SO$_2$F)$_2$ | 0.5, 1 |
| (0)-(13PRS)-0.5-(LiN(SO2F)2)-1 | — | — | LiPF$_6$ | 1 | 13PRS, LiN(SO$_2$F)$_2$ | 0.5, 1 |
| (1C-7)-0.5-(LiN(SO2F)(POF2))-1 | (1C-7) | 0.5 | LiPF$_6$ | 1 | LiN(SO$_2$F) (POF$_2$) | 1 |
| (0)-(VC)-0.5-(LiN(SO2F)(POF2))-1 | — | — | LiPF$_6$ | 1 | VC, LiN(SO$_2$F)(POF$_2$) | 0.5, 1 |
| (0)-(13PRS)-0.5-(LiN(SO2F)(POF2))-1 | — | — | LiPF$_6$ | 1 | 13PRS, LiN(SO$_2$F)(POF$_2$) | 0.5, 1 |
| (1C-7)-0.5-(LiN(FSO2)(POF propynyloxy))-1 | (1C-7) | 0.5 | LiPF$_6$ | 1 | LiN(FSO$_2$)(POF(OCH$_2$C≡CH)) | 1 |
| (0)-(VC)-0.5-(LiN(FSO2)(POF propynyloxy))-1 | — | — | LiPF$_6$ | 1 | VC, LiN(FSO$_2$)(POF(OCH$_2$C≡CH)) | 0.5, 1 |
| (0)-(13PRS)-0.5-(LiN(FSO2)(POF propynyloxy))-1 | — | — | LiPF$_6$ | 1 | 13PRS, LiN(FSO$_2$)(POF(OCH$_2$C≡CH)) | 0.5, 1 |
| (1C-7)-0.5-(LiSO3F)-1 | (1C-7) | 0.5 | LiPF$_6$ | 1 | LiSO$_3$F | 1 |
| (0)-(VC)-0.5-(LiSO3F)-1 | — | — | LiPF$_6$ | 1 | VC, LiSO$_3$F | 0.5, 1 |
| (0)-(13PRS)-0.5-(LiSO3F)-1 | — | — | LiPF$_6$ | 1 | 13PRS, LiSO$_3$F | 0.5, 1 |
| (1C-7)-0.5-(VC)-1 | (1C-7) | 0.5 | LiPF$_6$ | 1 | VC | 1 |
| (0)-(VC)-1.5 | — | — | LiPF$_6$ | 1 | VC | 1.5 |
| (0)-(13PRS)-0.5-(VC)-1 | — | — | LiPF$_6$ | 1 | 13PRS, VC | 0.5, 1 |
| (1C-7)-0.5-(FEC)-1 | (1C-7) | 0.5 | LiPF$_6$ | 1 | FEC | 1 |
| (0)-(VC)-0.5-(FEC)-1 | — | — | LiPF$_6$ | 1 | VC, FEC | 0.5, 1 |
| (0)-(13PRS)-0.5-(FEC)-1 | — | — | LiPF$_6$ | 1 | 13PRS, FEC | 0.5, 1 |
| (1C-7)-0.5-(13PS)-1 | (1C-7) | 0.5 | LiPF$_6$ | 1 | 13PS | 1 |
| (0)-(VC)-0.5-(13PS)-1 | — | — | LiPF$_6$ | 1 | VC, 13PS | 0.5, 1 |
| (0)-(13PRS)-0.5-(13PS)-1 | — | — | LiPF$_6$ | 1 | 13PRS, 13PS | 0.5, 1 |
| (1C-7)-0.5-(V4Si)-1 | (1C-7) | 0.5 | LiPF$_6$ | 1 | V4Si | 1 |
| (0)-(VC)-0.5-(V4Si)-1 | — | — | LiPF$_6$ | 1 | VC, V4Si | 0.5, 1 |
| (0)-(13PRS)-0.5-(V4Si)-1 | — | — | LiPF$_6$ | 1 | 13PRS, V4Si | 0.5, 1 |
| (1C-7)-0.5-(TDFEC)-1 | (1C-7) | 0.5 | LiPF$_6$ | 1 | TDFEC | 1 |
| (0)-(VC)-0.5-(TDFEC)-1 | — | — | LiPF$_6$ | 1 | VC, TDFEC | 0.5, 1 |
| (0)-(13PRS)-0.5-(TDFEC)-1 | — | — | LiPF$_6$ | 1 | 13PRS, TDFEC | 0.5, 1 |
| (1C-7)-0.5-(MMDS)-1 | (1C-7) | 0.5 | LiPF$_6$ | 1 | MMDS | 1 |
| (0)-(VC)-0.5-(MMDS)-1 | — | — | LiPF$_6$ | 1 | VC, MMDS | 0.5, 1 |
| (0)-(13PRS)-0.5-(MMDS)-1 | — | — | LiPF$_6$ | 1 | 13PRS, MMDS | 0.5, 1 |

TABLE 9

| Electrolyte solution No. | Imine compound Type | Conc. [mass %] | Solute Type | Conc. [mol/L] | Other solute and additive Type | Conc. [mass %] |
|---|---|---|---|---|---|---|
| (2C-4)-0.5-(0) | (2C-4) | 0.5 | $LiPF_6$ | 1 | — | — |
| (2C-4)-0.5-(LiPF2(Ox)2)-1 | (2C-4) | 0.5 | $LiPF_6$ | 1 | $LiPF_2(C_2O_4)_2$ | 1 |
| (2C-4)-0.5-(LiPF4(Ox))-1 | (2C-4) | 0.5 | $LiPF_6$ | 1 | $LiPF_4(C_2O_4)$ | 1 |
| (2C-4)-0.5-(LiBF2(Ox))-1 | (2C-4) | 0.5 | $LiPF_6$ | 1 | $LiBF_2(C_2O_4)$ | 1 |
| (2C-4)-0.5-(LiB(Ox)2)-1 | (2C-4) | 0.5 | $LiPF_6$ | 1 | $LiB(C_2O_4)_2$ | 1 |
| (2C-4)-0.5-(LiPO2F2)-1 | (2C-4) | 0.5 | $LiPF_6$ | 1 | $LiPO_2F_2$ | 1 |
| (2C-4)-0.5-(LiN(POF2)2)-1 | (2C-4) | 0.5 | $LiPF_6$ | 1 | $LiN(POF2)_2$ | 1 |
| (2C-4)-0.5-(LiN(SO2F)2)-1 | (2C-4) | 0.5 | $LiPF_6$ | 1 | $LiN(SO_2F)_2$ | 1 |
| (2C-4)-0.5-(LiN(SO2F)(POF2))-1 | (2C-4) | 0.5 | $LiPF_6$ | 1 | $LiN(SO_2F)(POF_2)$ | 1 |
| (2C-4)-0.5-(LiN(FSO2)(POF propynyloxy))-1 | (2C-4) | 0.5 | $LiPF_6$ | 1 | $LiN(FSO_2)(POF(OCH_2C≡CH))$ | 1 |
| (2C-4)-0.5-(LiSO3F)-1 | (2C-4) | 0.5 | $LiPF_6$ | 1 | $LiSO_3F$ | 1 |
| (2C-4)-0.5-(VC)-1 | (2C-4) | 0.5 | $LiPF_6$ | 1 | VC | 1 |
| (2C-4)-0.5-(FEC)-1 | (2C-4) | 0.5 | $LiPF_6$ | 1 | FEC | 1 |
| (2C-4)-0.5-(13PS)-1 | (2C-4) | 0.5 | $LiPF_6$ | 1 | 13PS | 1 |
| (2C-4)-0.5-(V4Si)-1 | (2C-4) | 0.5 | $LiPF_6$ | 1 | V4Si | 1 |
| (2C-4)-0.5-(12EDSAA)-1 | (2C-4) | 0.5 | $LiPF_6$ | 1 | 12EDSAA | 1 |
| (0)-(VC)-0.5-(12EDSAA)-1 | — | — | $LiPF_6$ | 1 | VC, 12EDSAA | 0.5, 1 |
| (0)-(13PRS)-0.5-(12EDSAA)-1 | — | — | $LiPF_6$ | 1 | 13PRS, 12EDSAA | 0.5, 1 |

TABLE 10

| Electrolyte solution No. | Imine compound Type | Conc. [mass %] | Solute Type | Conc. [mol/L] | Other solute and additive Type | Conc. [mass %] |
|---|---|---|---|---|---|---|
| (1C-11)-0.5-(0) | (1C-11) | 0.5 | $LiPF_6$ | 1 | — | — |
| (1C-11)-0.5-(LiPF2(Ox)2)-1 | (1C-11) | 0.5 | $LiPF_6$ | 1 | $LiPF_2(C_2O_4)_2$ | 1 |
| (1C-11)-0.5-(LiPF4(Ox))-1 | (1C-11) | 0.5 | $LiPF_6$ | 1 | $LiPF_4(C_2O_4)$ | 1 |
| (1C-11)-0.5-(LiBF2(Ox))-1 | (1C-11) | 0.5 | $LiPF_6$ | 1 | $LiBF_2(C_2O_4)$ | 1 |
| (1C-11)-0.5-(LiB(Ox)2)-1 | (1C-11) | 0.5 | $LiPF_6$ | 1 | $LiB(C_2O_4)_2$ | 1 |
| (1C-11)-0.5-(LiPO2F2)-1 | (1C-11) | 0.5 | $LiPF_6$ | 1 | $LiPO_2F_2$ | 1 |
| (1C-11)-0.5-(LiN(POF2)2)-1 | (1C-11) | 0.5 | $LiPF_6$ | 1 | $LiN(POF_2)_2$ | 1 |
| (1C-11)-0.5-(LiN(SO2F)2)-1 | (1C-11) | 0.5 | $LiPF_6$ | 1 | $LiN(SO_2F)_2$ | 1 |
| (1C-11)-0.5-(LiN(SO2F)(POF2))-1 | (1C-11) | 0.5 | $LiPF_6$ | 1 | $LiN(SO_2F)(POF_2)$ | 1 |
| (1C-11)-0.5-(LiN(FSO2)(POFpropynyloxy))-1 | (1C-11) | 0.5 | $LiPF_6$ | 1 | $LiN(FSO_2)(POF(OCH_2C≡CH))$ | 1 |
| (1C-11)-0.5-(LiSO3F)-1 | (1C-11) | 0.5 | $LiPF_6$ | 1 | $LiSO_3F$ | 1 |
| (1C-11)-0.5-(VC)-1 | (1C-11) | 0.5 | $LiPF_6$ | 1 | VC | 1 |
| (1C-11)-0.5-(FEC)-1 | (1C-11) | 0.5 | $LiPF_6$ | 1 | FEC | 1 |
| (1C-11)-0.5-(13PS)-1 | (1C-11) | 0.5 | $LiPF_6$ | 1 | 13PS | 1 |
| (1C-11)-0.5-(V4Si)-1 | (1C-11) | 0.5 | $LiPF_6$ | 1 | V4Si | 1 |
| (1C-11)-0.5-(EEC)-1 | (1C-11) | 0.5 | $LiPF_6$ | 1 | EEC | 1 |
| (0)-(VC)-0.5-(EEC)-1 | — | — | $LiPF_6$ | 1 | VC, EEC | 0.5, 1 |
| (0)-(13PRS)-0.5-(EEC)-1 | — | — | $LiPF_6$ | 1 | 13PRS, EEC | 0.5, 1 |
| (1S-4)-0.5-(0) | (1S-4) | 0.5 | $LiPF_6$ | 1 | — | — |
| (1S-4)-0.5-(LiPF2(Ox)2)-1 | (1S-4) | 0.5 | $LiPF_6$ | 1 | $LiPF_2(C_2O_4)_2$ | 1 |
| (1S-4)-0.5-(LiPF4(Ox))-1 | (1S-4) | 0.5 | $LiPF_6$ | 1 | $LiPF_4(C_2O_4)$ | 1 |
| (1S-5)-0.5-(0) | (1S-5) | 0.5 | $LiPF_6$ | 1 | — | — |
| (1S-5)-0.5-(LiPF2(Ox)2)-1 | (1S-5) | 0.5 | $LiPF_6$ | 1 | $LiPF_2(C_2O_4)_2$ | 1 |
| (1S-5)-0.5-(LiPF4(Ox))-1 | (1S-5) | 0.5 | $LiPF_6$ | 1 | $LiPF_4(C_2O_4)$ | 1 |
| (1S-5)-0.5-(LiBF2(Ox))-1 | (1S-5) | 0.5 | $LiPF_6$ | 1 | $LiBF_2(CO_2O_4)$ | 1 |
| (1S-5)-0.5-(LiB(Ox)2)-1 | (1S-5) | 0.5 | $LiPF_6$ | 1 | $LiB(C_2O_4)_2$ | 1 |
| (1S-5)-0.5-(LiPO2F2)-1 | (1S-5) | 0.5 | $LiPF_6$ | 1 | $LiPO_2F_2$ | 1 |
| (1S-5)-0.5-(LiN(POF2)2)-1 | (1S-5) | 0.5 | $LiPF_6$ | 1 | $LiN(POF_2)_2$ | 1 |
| (1S-5)-0.5-(LiN(SO2F)2)-1 | (1S-5) | 0.5 | $LiPF_6$ | 1 | $LiN(SO_2F)_2$ | 1 |
| (1S-5)-0.5-(LiN(SO2F)(POF2))-1 | (1S-5) | 0.5 | $LiPF_6$ | 1 | $LiN(SO_2F)(POF_2)$ | 1 |
| (1S-5)-0.5-(LiN(FSO2)(POFpropynyloxy))-1 | (1S-5) | 0.5 | $LiPF_6$ | 1 | $LiN(FSO_2)(POF(OCH_2C≡CH))$ | 1 |
| (1S-5)-0.5-(LiSO3F)-1 | (1S-5) | 0.5 | $LiPF_6$ | 1 | $LiSO_3F$ | 1 |
| (1S-5)-0.5-(VC)-1 | (1S-5) | 0.5 | $LiPF_6$ | 1 | VC | 1 |
| (1S-5)-0.5-(FEC)-1 | (1S-5) | 0.5 | $LiPF_6$ | 1 | FEC | 1 |
| (1S-5)-0.5-(13PS)-1 | (1S-5) | 0.5 | $LiPF_6$ | 1 | 13PS | 1 |
| (1S-5)-0.5-(V4Si)-1 | (1S-5) | 0.5 | $LiPF_6$ | 1 | V4Si | 1 |
| (1S-5)-0.5-(DICH)-1 | (1S-5) | 0.5 | $LiPF_6$ | 1 | DICH | 1 |
| (0)-(VC)-0.5-(DICH)-1 | — | — | $LiPF_6$ | 1 | VC, DICH | 0.5, 1 |
| (0)-(13PRS)-0.5-(DICH)-1 | — | — | $LiPF_6$ | 1 | 13PRS, DICH | 0.5, 1 |
| (1S-5)-0.5-(SN)-1 | (1S-5) | 0.5 | $LiPF_6$ | 1 | SN | 1 |
| (0)-(VC)-0.5-(SN)-1 | — | — | $LiPF_6$ | 1 | VC, SN | 0.5, 1 |
| (0)-(13PRS)-0.5-(SN)-1 | — | — | $LiPF_6$ | 1 | 13PRS, SN | 0.5, 1 |

TABLE 10-continued

|  | Imine compound | | Solute | | Other solute and additive | |
|---|---|---|---|---|---|---|
| Electrolyte solution No. | Type | Conc. [mass %] | Type | Conc. [mol/L] | Type | Conc. [mass %] |
| (1S-5)-0.5-(EPFCTP)-1 | (1S-5) | 0.5 | $LiPF_6$ | 1 | EPFCTP | 1 |
| (0)-(VC)-0.5-(EPFCTP)-1 | — | — | $LiPF_6$ | 1 | VC, EPFCTP | 0.5, 1 |
| (0)-(13PRS)-0.5-(EPFCTP)-1 | — | — | $LiPF_6$ | 1 | 13PRS, EPFCTP | 0.5, 1 |

TABLE 11

|  | Electrolyte solution No. | Positive electrode active material | Negative electrode active material | Initial gas amount* [%] | Capacity after storage* [%] |
|---|---|---|---|---|---|
| Example 2-1 | (1C-1)-0.5-(0) | $LiNi_{0.6}Co_{0.2}Mn_{0.2}O_2$ | Graphite | 75 | 107 |
| Comparative Example 2-1a | (0)-(VC)-0.5 |  |  | 95 | 103 |
| Comparative Example 2-1b | (0)-(13PRS)-0.5 |  |  | 93 | 101 |
| Example 2-2 | (1C-1)-0.5-(LiPF2(Ox)2)-1 |  |  | 115 | 119 |
| Comparative Example 2-2a | (0)-(VC)-0.5-(LiPF2(Ox)2)-1 |  |  | 141 | 112 |
| Comparative Example 2-2b | (0)-(13PRS)-0.5-(LiPF2(Ox)2)-1 |  |  | 139 | 114 |
| Example 2-3 | (1C-1)-0.5-(LiPF4(Ox))-1 |  |  | 71 | 126 |
| Comparative Example 2-3a | (0)-(VC)-0.5-(LiPF4(Ox))-1 |  |  | 93 | 118 |
| Comparative Example 2-3b | (0)-(13PRS)-0.5-(LiPF4(Ox))-1 |  |  | 90 | 117 |
| Example 3-1 | (1C-4)-0.5-(0) |  |  | 71 | 110 |
| Comparative Example 3-1a | (0)-(VC)-0.5 |  |  | 95 | 103 |
| Comparative Example 3-1b | (0)-(13PRS)-0.5 |  |  | 93 | 101 |
| Example 3-2 | (1C-4)-0.5-(LiPF2(Ox)2)-1 |  |  | 117 | 119 |
| Comparative Example 3-2a | (0)-(VC)-0.5-(LiPF2(Ox)2)-1 |  |  | 141 | 112 |
| Comparative Example 3-2b | (0)-(13PRS)-0.5-(LiPF2(Ox)2)-1 |  |  | 139 | 114 |
| Example 3-3 | (1C-4)-0.5-(LiPF4(Ox))-1 |  |  | 70 | 128 |
| Comparative Example 3-3a | (0)-(VC)-0.5-(LiPF4(Ox))-1 |  |  | 93 | 118 |
| Comparative Example 3-3b | (0)-(13PRS)-0.5-(LiPF4(Ox))-1 |  |  | 90 | 117 |
| Comparative Example 1-1 | (0)-(0) |  |  | 100 | 100 |

*Relative values when the result of evaluation of Comparative Example 1-1 was defined as 100.

TABLE 12

|  | Electrolyte solution No. | Positive electrode active material | Negative electrode active material | Initial gas amount* [%] | Capacity after storage* [%] |
|---|---|---|---|---|---|
| Example 4-1 | (1C-7)-0.5-(0) | $LiNi_{0.6}Co_{0.2}Mn_{0.2}O_2$ | Graphite | 71 | 108 |
| Comparative Example 4-1a | (0)-(VC)-0.5 |  |  | 95 | 103 |
| Comparative Example 4-1b | (0)-(13PRS)-0.5 |  |  | 93 | 101 |
| Example 4-2 | (1C-7)-0.5-(LiPF2(Ox)2)-1 |  |  | 111 | 121 |
| Comparative Example 4-2a | (0)-(VC)-0.5-(LiPF2(Ox)2)-1 |  |  | 141 | 112 |
| Comparative Example 4-2b | (0)-(13PRS)-0.5-(LiPF2(Ox)2)-1 |  |  | 139 | 114 |
| Example 4-3 | (1C-7)-0.5-(LiPF4(Ox))-1 |  |  | 70 | 126 |

TABLE 12-continued

| | Electrolyte solution No. | Positive electrode active material | Negative electrode active material | Initial gas amount* [%] | Capacity after storage* [%] |
|---|---|---|---|---|---|
| Comparative Example 4-3a | (0)-(VC)-0.5-(LiPF4(Ox))-1 | | | 93 | 118 |
| Comparative Example 4-3b | (0)-(13PRS)-0.5-(LiPF4(Ox))-1 | | | 90 | 117 |
| Example 4-4 | (1C-7)-0.5-(LiBF2(Ox))-1 | | | 69 | 119 |
| Comparative Example 4-4a | (0)-(VC)-0.5-(LiBF2(Ox))-1 | | | 93 | 115 |
| Comparative Example 4-4b | (0)-(13PRS)-0.5-(LiBF2(Ox))-1 | | | 92 | 114 |
| Example 4-5 | (1C-7)-0.5-(LiB(Ox)2)-1 | | | 67 | 119 |
| Comparative Example 4-5a | (0)-(VC)-0.5-(LiB(Ox)2)-1 | | | 88 | 114 |
| Comparative Example 4-5b | (0)-(13PRS)-0.5-(LiB(Ox)2)-1 | | | 89 | 114 |
| Example 4-6 | (1C-7)-0.5-(LiPO2F2)-1 | | | 68 | 120 |
| Comparative Example 4-6a | (0)-(VC)-0.5-(LiPO2F2)-1 | | | 88 | 115 |
| Comparative Example 4-6b | (0)-(13PRS)-0.5-(LiPO2F2)-1 | | | 90 | 112 |
| Example 4-7 | (1C-7)-0.5-(LiN(POF2)2)-1 | | | 70 | 121 |
| Comparative Example 4-7a | (0)-(VC)-0.5-(LiN(POF2)2)-1 | | | 90 | 114 |
| Comparative Example 4-7b | (0)-(13PRS)-0.5-(LiN(POF2)2)-1 | | | 91 | 113 |
| Example 4-8 | (1C-7)-0.5-(LiN(SO2F)2)-1 | | | 70 | 111 |
| Comparative Example 4-8a | (0)-(VC)-0.5-(LiN(SO2F)2)-1 | | | 92 | 107 |
| Comparative Example 4-8b | (0)-(13PRS)-0.5-(LiN(SO2F)2)-1 | | | 93 | 105 |
| Example 4-9 | (1C-7)-0.5-(LiN(SO2F)(POF2))-1 | | | 67 | 127 |
| Comparative Example 4-9a | (0)-(VC)-0.5-(LiN(SO2F)(POF2))-1 | | | 87 | 118 |
| Comparative Example 4-9b | (0)-(13PRS)-0.5-(LiN(SO2F)(POF2))-1 | | | 88 | 117 |
| Example 4-10 | (1C-7)-0.5-(LiN(FSO2)(POFpropynyloxy))-1 | | | 68 | 130 |
| Comparative Example 4-10a | (0)-(VC)-0.5-(LiN(FSO2)(POFpropynyloxy))-1 | | | 88 | 119 |
| Comparative Example 4-10b | (0)-(13PRS)-0.5-(LiN(FSO2)(PO))-1 | | | 89 | 115 |
| Example 4-11 | (1C-7)-0.5-(LiSO3F)-1 | | | 70 | 112 |
| Comparative Example 4-11a | (0)-(VC)-0.5-(LiSO3F)-1 | | | 94 | 107 |
| Comparative Example 4-11b | (0)-(13PRS)-0.5-(LiSO3F)-1 | | | 92 | 105 |
| Example 4-12 | (1C-7)-0.5-(VC)-1 | | | 70 | 111 |
| Comparative Example 4-12a | (0)-(VC)-1.5 | | | 88 | 107 |
| Comparative Example 4-12b | (0)-(13PRS)-0.5-(VC)-1 | | | 92 | 106 |
| Example 4-13 | (1C-7)-0.5-(FEC)-1 | | | 64 | 112 |
| Comparative Example 4-13a | (0)-(VC)-0.5-(FEC)-1 | | | 85 | 105 |
| Comparative Example 4-13b | (0)-(13PRS)-0.5-(FEC)-1 | | | 87 | 105 |
| Example 4-14 | (1C-7)-0.5-(13PS)-1 | | | 69 | 113 |
| Comparative Example 4-14a | (0)-(VC)-0.5-(13PS)-1 | | | 90 | 107 |
| Comparative Example 4-14b | (0)-(13PRS)-0.5-(13PS)-1 | | | 92 | 106 |
| Example 4-15 | (1C-7)-0.5-(V4Si)-1 | | | 72 | 117 |
| Comparative Example 4-15a | (0)-(VC)-0.5-(V4Si)-1 | | | 93 | 107 |
| Comparative Example 4-15b | (0)-(13PRS)-0.5-(V4Si)-1 | | | 93 | 103 |
| Example 4-16 | (1C-7)-0.5-(TDFEC)-1 | | | 68 | 109 |
| Comparative Example 4-16a | (0)-(VC)-0.5-(TDFEC)-1 | | | 91 | 105 |
| Comparative Example 4-16b | (0)-(13PRS)-0.5-(TDFEC)-1 | | | 91 | 103 |
| Example 4-17 | (1C-7)-0.5-(MMDS)-1 | | | 69 | 119 |
| Comparative Example 4-17a | (0)-(VC)-0.5-(MMDS)-1 | | | 89 | 109 |

TABLE 12-continued

|  | Electrolyte solution No. | Positive electrode active material | Negative electrode active material | Initial gas amount* [%] | Capacity after storage* [%] |
|---|---|---|---|---|---|
| Comparative Example 4-17b | (0)-(13PRS)-0.5-(MMDS)-1 |  |  | 92 | 105 |
| Comparative Example 1-1 | (0)-(0) |  |  | 100 | 100 |

*Relative values when the result of evaluation of Comparative Example 1-1 was defined as 100.

TABLE 13

|  | Electrolyte solution No. | Positive electrode active material | Negative electrode active material | Initial gas amount* [%] | Capacity after storage* [%] |
|---|---|---|---|---|---|
| Example 5-1 | (2C-4)-0.5-(0) | $LiNi_{0.6}Co_{0.2}Mn_{0.2}O_2$ | Graphite | 78 | 106 |
| Comparative Example 5-1a | (0)-(VC)-0.5 |  |  | 95 | 103 |
| Comparative Example 5-1b | (0)-(13PRS)-0.5 |  |  | 93 | 101 |
| Example 5-2 | (2C-4)-0.5-(LiPF2(Ox)2)-1 |  |  | 118 | 113 |
| Comparative Example 5-2a | (0)-(VC)-0.5-(LiPF2(Ox)2)-1 |  |  | 141 | 112 |
| Comparative Example 5-2b | (0)-(13PRS)-0.5-(LiPF2(Ox)2)-1 |  |  | 139 | 114 |
| Example 5-3 | (2C-4)-0.5-(LiPF4(Ox))-1 |  |  | 75 | 120 |
| Comparative Example 5-3a | (0)-(VC)-0.5-(LiPF4(Ox))-1 |  |  | 93 | 118 |
| Comparative Example 5-3b | (0)-(13PRS)-0.5-(LiPF4(Ox))-1 |  |  | 90 | 117 |
| Example 5-4 | (2C-4)-0.5-(LiBF2(Ox))-1 |  |  | 77 | 115 |
| Comparative Example 5-4a | (0)-(VC)-0.5-(LiBF2(Ox))-1 |  |  | 93 | 115 |
| Comparative Example 5-4b | (0)-(13PRS)-0.5-(LiBF2(Ox))-1 |  |  | 92 | 114 |
| Example 5-5 | (2C-4)-0.5-(LiB(Ox)2)-1 |  |  | 75 | 116 |
| Comparative Example 5-5a | (0)-(VC)-0.5-(LiB(Ox)2)-1 |  |  | 88 | 114 |
| Comparative Example 5-5b | (0)-(13PRS)-0.5-(LiB(Ox)2)-1 |  |  | 89 | 114 |
| Example 5-6 | (2C-4)-0.5-(LiPO2F2)-1 |  |  | 72 | 115 |
| Comparative Example 5-6a | (0)-(VC)-0.5-(LiPO2F2)-1 |  |  | 88 | 115 |
| Comparative Example 5-6b | (0)-(13PRS)-0.5-(LiPO2F2)-1 |  |  | 90 | 112 |
| Example 5-7 | (2C-4)-0.5-(LiN(POF2)2)-1 |  |  | 75 | 114 |
| Comparative Example 5-7a | (0)-(VC)-0.5-(LiN(POF2)2)-1 |  |  | 90 | 114 |
| Comparative Example 5-7b | (0)-(13PRS)-0.5-(LiN(POF2)2)-1 |  |  | 91 | 113 |
| Example 5-8 | (2C-4)-0.5-(LiN(SO2F)2)-1 |  |  | 77 | 105 |
| Comparative Example 5-8a | (0)-(VC)-0.5-(LiN(SO2F)2)-1 |  |  | 92 | 107 |
| Comparative Example 5-8b | (0)-(13PRS)-0.5-(LiN(SO2F)2)-1 |  |  | 93 | 105 |
| Example 5-9 | (2C-4)-0.5-(LiN(SO2F)(POF2))-1 |  |  | 74 | 120 |
| Comparative Example 5-9a | (0)-(VC)-0.5-(LiN(SO2F)(POF2))-1 |  |  | 87 | 118 |
| Comparative Example 5-9b | (0)-(13PRS)-0.5-(LiN(SO2F)(POF2))-1 |  |  | 88 | 117 |
| Example 5-10 | (2C-4)-0.5-(LiN(FSO2)(POFpropynyloxy))-1 |  |  | 73 | 119 |
| Comparative Example 5-10a | (0)-(VC)-0.5-(LiN(FSO2)(POFpropynyloxy))-1 |  |  | 88 | 119 |
| Comparative Example 5-10b | (0)-(13PRS)-0.5-(LiN(FSO2)(POFpropynyloxy))-1 |  |  | 89 | 115 |
| Example 5-11 | (2C-4)-0.5-(LiSO3F)-1 |  |  | 76 | 106 |
| Comparative Example 5-11a | (0)-(VC)-0.5-(LiSO3F)-1 |  |  | 94 | 107 |
| Comparative Example 5-11b | (0)-(13PRS)-0.5-(LiSO3F)-1 |  |  | 92 | 105 |
| Example 5-12 | (2C-4)-0.5-(VC)-1 |  |  | 76 | 111 |
| Comparative Example 5-12a | (0)-(VC)-1.5 |  |  | 88 | 107 |

TABLE 13-continued

| | Electrolyte solution No. | Positive electrode active material | Negative electrode active material | Initial gas amount* [%] | Capacity after storage* [%] |
|---|---|---|---|---|---|
| Comparative Example 5-12b | (0)-(13PRS)-0.5-(VC)-1 | | | 92 | 106 |
| Example 5-13 | (2C-4)-0.5-(FEC)-1 | | | 74 | 106 |
| Comparative Example 5-13a | (0)-(VC)-0.5-(FEC)-1 | | | 85 | 105 |
| Comparative Example 5-13b | (0)-(13PRS)-0.5-(FEC)-1 | | | 87 | 105 |
| Example 5-14 | (2C-4)-0.5-(13PS)-1 | | | 76 | 107 |
| Comparative Example 5-14a | (0)-(VC)-0.5-(13PS)-1 | | | 90 | 107 |
| Comparative Example 5-14b | (0)-(13PRS)-0.5-(13PS)-1 | | | 92 | 106 |
| Example 5-15 | (2C-4)-0.5-(V4Si)-1 | | | 73 | 110 |
| Comparative Example 5-15a | (0)-(VC)-0.5-(V4Si)-1 | | | 93 | 107 |
| Comparative Example 5-15b | (0)-(13PRS)-0.5-(V4Si)-1 | | | 93 | 103 |
| Example 5-16 | (2C-4)-0.5-(12EDSAA)-1 | | | 79 | 105 |
| Comparative Example 5-16a | (0)-(VC)-0.5-(12EDSAA)-1 | | | 91 | 105 |
| Comparative Example 5-16b | (0)-(13PRS)-0.5-(12EDSAA)-1 | | | 90 | 106 |
| Comparative Example 1-1 | (0)-(0) | | | 100 | 100 |

*Relative values when the result of evaluation of Comparative Example 1-1 was defined as 100.

TABLE 14

| | Electrolyte solution No. | Positive electrode active material | Negative electrode active material | Initial gas amount* [%] | Capacity after storage* [%] |
|---|---|---|---|---|---|
| Example 6-1 | (1C-11)-0.5-(0) | $LiNi_{0.6}Co_{0.2}Mn_{0.2}O_2$ | Graphite | 72 | 109 |
| Comparative Example 6-1a | (0)-(VC)-0.5 | | | 95 | 103 |
| Comparative Example 6-1b | (0)-(13PRS)-0.5 | | | 93 | 101 |
| Example 6-2 | (1C-11)-0.5-(LiPF2(Ox)2)-1 | | | 111 | 118 |
| Comparative Example 6-2a | (0)-(VC)-0.5-(LiPF2(Ox)2)-1 | | | 141 | 112 |
| Comparative Example 6-2b | (0)-(13PRS)-0.5-(LiPF2(Ox)2)-1 | | | 139 | 114 |
| Example 6-3 | (1C-11)-0.5-(LiPF4(Ox))-1 | | | 70 | 127 |
| Comparative Example 6-3a | (0)-(VC)-0.5-(LiPF4(Ox))-1 | | | 93 | 118 |
| Comparative Example 6-3b | (0)-(13PRS)-0.5-(LiPF4(Ox))-1 | | | 90 | 117 |
| Example 6-4 | (1C-11)-0.5-(LiBF2(Ox))-1 | | | 72 | 121 |
| Comparative Example 6-4a | (0)-(VC)-0.5-(LiBF2(Ox))-1 | | | 93 | 115 |
| Comparative Example 6-4b | (0)-(13PRS)-0.5-(LiBF2(Ox))-1 | | | 92 | 114 |
| Example 6-5 | (1C-11)-0.5-(LiB(Ox)2)-1 | | | 73 | 122 |
| Comparative Example 6-5a | (0)-(VC)-0.5-(LiB(Ox)2)-1 | | | 88 | 114 |
| Comparative Example 6-5b | (0)-(13PRS)-0.5-(LiB(Ox)2)-1 | | | 89 | 114 |
| Example 6-6 | (1C-11)-0.5-(LiPO2F2)-1 | | | 68 | 122 |
| Comparative Example 6-6a | (0)-(VC)-0.5-(LiPO2F2)-1 | | | 88 | 115 |
| Comparative Example 6-6b | (0)-(13PRS)-0.5-(LiPO2F2)-1 | | | 90 | 112 |
| Example 6-7 | (1C-11)-0.5-(LiN(POF2)2)-1 | | | 67 | 122 |
| Comparative Example 6-7a | (0)-(VC)-0.5-(LiN(POF2)2)-1 | | | 90 | 114 |
| Comparative Example 6-7b | (0)-(13PRS)-0.5-(LiN(POF2)2)-1 | | | 91 | 113 |
| Example 6-8 | (1C-11)-0.5-(LiN(SO2F)2)-1 | | | 71 | 109 |
| Comparative Example 6-8a | (0)-(VC)-0.5-(LiN(SO2F)2)-1 | | | 92 | 107 |

TABLE 14-continued

|  | Electrolyte solution No. | Positive electrode active material | Negative electrode active material | Initial gas amount* [%] | Capacity after storage* [%] |
|---|---|---|---|---|---|
| Comparative Example 6-8b | (0)-(13PRS)-0.5-(LiN(SO2F)2)-1 |  |  | 93 | 105 |
| Example 6-9 | (1C-11)-0.5-(LiN(SO2F)(POF2))-1 |  |  | 67 | 129 |
| Comparative Example 6-9a | (0)-(VC)-0.5-(LiN(SO2F)(POF2))-1 |  |  | 87 | 118 |
| Comparative Example 6-9b | (0)-(13PRS)-0.5-(LiN(SO2F)(POF2))-1 |  |  | 88 | 117 |
| Example 6-10 | (1C-11)-0.5-(LiN(FSO2)(POFpropynyloxy))-1 |  |  | 66 | 132 |
| Comparative Example 6-10a | (0)-(VC)-0.5-(LiN(FSO2)(POFpropynyloxy))-1 |  |  | 88 | 119 |
| Comparative Example 6-10b | (0)-(13PRS)-0.5-(LiN(FSO2)(POFpropynyloxy))-1 |  |  | 89 | 115 |
| Example 6-11 | (1C-11)-0.5-(LiSO3F)-1 |  |  | 72 | 109 |
| Comparative Example 6-11a | (0)-(VC)-0.5-(LiSO3F)-1 |  |  | 94 | 107 |
| Comparative Example 6-11b | (0)-(13PRS)-0.5-(LiSO3F)-1 |  |  | 92 | 105 |
| Example 6-12 | (1C-11)-0.5-(VC)-1 |  |  | 69 | 119 |
| Comparative Example 6-12a | (0)-(VC)-1.5 |  |  | 88 | 107 |
| Comparative Example 6-12b | (0)-(13PRS)-0.5-(VC)-1 |  |  | 92 | 106 |
| Example 6-13 | (1C-11)-0.5-(FEC)-1 |  |  | 68 | 110 |
| Comparative Example 6-13a | (0)-(VC)-0.5-(FEC)-1 |  |  | 85 | 105 |
| Comparative Example 6-13b | (0)-(13PRS)-0.5-(FEC)-1 |  |  | 87 | 105 |
| Example 6-14 | (1C-11)-0.5-(13PS)-1 |  |  | 71 | 112 |
| Comparative Example 6-14a | (0)-(VC)-0.5-(13PS)-1 |  |  | 90 | 107 |
| Comparative Example 6-14b | (0)-(13PRS)-0.5-(13PS)-1 |  |  | 92 | 106 |
| Example 6-15 | (1C-11)-0.5-(V4Si)-1 |  |  | 68 | 117 |
| Comparative Example 6-15a | (0)-(VC)-0.5-(V4Si)-1 |  |  | 93 | 107 |
| Comparative Example 6-15b | (0)-(13PRS)-0.5-(V4Si)-1 |  |  | 93 | 103 |
| Example 6-16 | (1C-11)-0.5-(EEC)-1 |  |  | 71 | 113 |
| Comparative Example 6-16a | (0)-(VC)-0.5-(EEC)-1 |  |  | 91 | 107 |
| Comparative Example 6-16b | (0)-(13PRS)-0.5-(EEC)-1 |  |  | 92 | 107 |
| Example 7-1 | (1S-4)-0.5-(0) |  |  | 73 | 104 |
| Comparative Example 7-1a | (0)-(VC)-0.5 |  |  | 95 | 103 |
| Comparative Example 7-1b | (0)-(13PRS)-0.5 |  |  | 93 | 101 |
| Example 7-2 | (1S-4)-0.5-(LiPF2(Ox)2)-1 |  |  | 119 | 114 |
| Comparative Example 7-2a | (0)-(VC)-0.5-(LiPF2(Ox)2)-1 |  |  | 141 | 112 |
| Comparative Example 7-2b | (0)-(13PRS)-0.5-(LiPF2(Ox)2)-1 |  |  | 139 | 114 |
| Example 7-3 | (1S-4)-0.5-(LiPF4(Ox))-1 |  |  | 72 | 118 |
| Comparative Example 7-3a | (0)-(VC)-0.5-(LiPF4(Ox))-1 |  |  | 93 | 118 |
| Comparative Example 7-4b | (0)-(13PRS)-0.5-(LiPF4(Ox))-1 |  |  | 90 | 117 |
| Comparative Example 1-1 | (0)-(0) |  |  | 100 | 100 |

*Relative values when the result of evaluation of Comparative Example 1-1 was defined as 100.

TABLE 15

|  | Electrolyte solution No. | Positive electrode active material | Negative electrode active material | Initial gas amount* [%] | Capacity after storage* [%] |
|---|---|---|---|---|---|
| Example 8-1 | (1S-5)-0.5-(0) | $LiNi_{0.6}Co_{0.2}Mn_{0.2}O_2$ | Graphite | 77 | 104 |
| Comparative Example 8-1a | (0)-(VC)-0.5 |  |  | 95 | 103 |

TABLE 15-continued

|  | Electrolyte solution No. | Positive electrode active material | Negative electrode active material | Initial gas amount* [%] | Capacity after storage* [%] |
|---|---|---|---|---|---|
| Comparative Example 8-1b | (0)-(13PRS)-0.5 |  |  | 93 | 101 |
| Example 8-2 | (1S-5)-0.5-(LiPF2(Ox)2)-1 |  |  | 118 | 117 |
| Comparative Example 8-2a | (0)-(VC)-0.5-(LiPF2(Ox)2)-1 |  |  | 141 | 112 |
| Comparative Example 8-2b | (0)-(13PRS)-0.5-(LiPF2(Ox)2)-1 |  |  | 139 | 114 |
| Example 8-3 | (1S-5)-0.5-(LiPF4(Ox))-1 |  |  | 73 | 123 |
| Comparative Example 8-3a | (0)-(VC)-0.5-(LiPF4(Ox))-1 |  |  | 93 | 118 |
| Comparative Example 8-3b | (0)-(13PRS)-0.5-(LiPF4(Ox))-1 |  |  | 90 | 117 |
| Example 8-4 | (1S-5)-0.5-(LiBF2(Ox))-1 |  |  | 73 | 120 |
| Comparative Example 8-4a | (0)-(VC)-0.5-(LiBF2(Ox))-1 |  |  | 93 | 115 |
| Comparative Example 8-4b | (0)-(13PRS)-0.5-(LiBF2(Ox))-1 |  |  | 92 | 114 |
| Example 8-5 | (1S-5)-0.5-(LiB(Ox)2)-1 |  |  | 74 | 120 |
| Comparative Example 8-5a | (0)-(VC)-0.5-(LiB(Ox)2)-1 |  |  | 88 | 114 |
| Comparative Example 8-5b | (0)-(13PRS)-0.5-(LiB(Ox)2)-1 |  |  | 89 | 114 |
| Example 8-6 | (1S-5)-0.5-(LiPO2F2)-1 |  |  | 72 | 123 |
| Comparative Example 8-6a | (0)-(VC)-0.5-(LiPO2F2)-1 |  |  | 88 | 115 |
| Comparative Example 8-6b | (0)-(13PRS)-0.5-(LiPO2F2)-1 |  |  | 90 | 112 |
| Example 8-7 | (1S-5)-0.5-(LiN(POF2)2)-1 |  |  | 72 | 121 |
| Comparative Example 8-7a | (0)-(VC)-0.5-(LiN(POF2)2)-1 |  |  | 90 | 114 |
| Comparative Example 8-7b | (0)-(13PRS)-0.5-(LiN(POF2)2)-1 |  |  | 91 | 113 |
| Example 8-8 | (1S-5)-0.5-(LiN(SO2F)2)-1 |  |  | 75 | 110 |
| Comparative Example 8-8a | (0)-(VC)-0.5-(LiN(SO2F)2)-1 |  |  | 92 | 107 |
| Comparative Example 8-8b | (0)-(13PRS)-0.5-(LiN(SO2F)2)-1 |  |  | 93 | 105 |
| Example 8-9 | (1S-5)-0.5-(LiN(SO2F)(POF2))-1 |  |  | 70 | 125 |
| Comparative Example 8-9a | (0)-(VC)-0.5-(LiN(SO2F)(POF2))-1 |  |  | 87 | 118 |
| Comparative Example 8-9b | (0)-(13PRS)-0.5-(LiN(SO2F)(POF2))-1 |  |  | 88 | 117 |
| Example 8-10 | (1S-5)-0.5-(LiN(FSO2)(POFpropynyloxy))-1 |  |  | 71 | 130 |
| Comparative Example 8-10a | (0)-(VC)-0.5-(LiN(FSO2)(POFpropynyloxy))-1 |  |  | 88 | 119 |
| Comparative Example 8-10b | (0)-(13PRS)-0.5-(LiN(FSO2)(POFpropynyloxy))-1 |  |  | 89 | 115 |
| Example 8-11 | (1S-5)-0.5-(LiSO3F)-1 |  |  | 76 | 111 |
| Comparative Example 8-11a | (0)-(VC)-0.5-(LiSO3F)-1 |  |  | 94 | 107 |
| Comparative Example 8-11b | (0)-(13PRS)-0.5-(LiSO3F)-1 |  |  | 92 | 105 |
| Example 8-12 | (1S-5)-0.5-(VC)-1 |  |  | 72 | 114 |
| Comparative Example 8-12a | (0)-(VC)-1.5 |  |  | 88 | 107 |
| Comparative Example 8-12b | (0)-(13PRS)-0.5-(VC)-1 |  |  | 92 | 106 |
| Example 8-13 | (1S-5)-0.5-(FEC)-1 |  |  | 71 | 110 |
| Comparative Example 8-13a | (0)-(VC)-0.5-(FEC)-1 |  |  | 85 | 105 |
| Comparative Example 8-13b | (0)-(13PRS)-0.5-(FEC)-1 |  |  | 87 | 105 |
| Example 8-14 | (1S-5)-0.5-(13PS)-1 |  |  | 74 | 111 |
| Comparative Example 8-14a | (0)-(VC)-0.5-(13PS)-1 |  |  | 90 | 107 |
| Comparative Example 8-14b | (0)-(13PRS)-0.5-(13PS)-1 |  |  | 92 | 106 |
| Example 8-15 | (1S-5)-0.5-(V4Si)-1 |  |  | 70 | 115 |
| Comparative Example 8-15a | (0)-(VC)-0.5-(V4Si)-1 |  |  | 93 | 107 |
| Comparative Example 8-15b | (0)-(13PRS)-0.5-(V4Si)-1 |  |  | 93 | 103 |
| Example 8-16 | (1S-5)-0.5-(DICH)-1 |  |  | 77 | 109 |

TABLE 15-continued

|  | Electrolyte solution No. | Positive electrode active material | Negative electrode active material | Initial gas amount* [%] | Capacity after storage* [%] |
|---|---|---|---|---|---|
| Comparative Example 8-16a | (0)-(VC)-0.5-(DICH)-1 | | | 96 | 105 |
| Comparative Example 8-16b | (0)-(13PRS)-0.5-(DICH)-1 | | | 96 | 106 |
| Example 8-17 | (1S-5)-0.5-(SN)-1 | | | 78 | 107 |
| Comparative Example 8-17a | (0)-(VC)-0.5-(SN)-1 | | | 93 | 104 |
| Comparative Example 8-17b | (0)-(13PRS)-0.5-(SN)-1 | | | 95 | 104 |
| Example 8-18 | (1S-5)-0.5-(EPFCTP)-1 | | | 76 | 113 |
| Comparative Example 8-18a | (0)-(VC)-0.5-(EPFCTP)-1 | | | 95 | 105 |
| Comparative Example 8-18b | (0)-(13PRS)-0.5-(EPFCTP)-1 | | | 93 | 106 |
| Comparative Example 1-1 | (0)-(0) | | | 100 | 100 |

*Relative values when the result of evaluation of Comparative Example 1-1 was defined as 100.

TABLE 16

| | Imine compound | | Solute | | Other solute and additive | |
|---|---|---|---|---|---|---|
| Electrolyte solution No. | Type | Conc. [mass %] | Type | Conc. [mol/L] | Compound | Conc. [mass %] |
| (1C-1)-0.01-(0) | (1C-1) | 0.01 | LiPF$_6$ | 1 | — | — |
| (0)-(VC)-0.01 | — | — | LiPF$_6$ | 1 | VC | 0.01 |
| (0)-(13PRS)-0.01 | — | — | LiPF$_6$ | 1 | 13PRS | 0.01 |
| (1C-1)-0.01-(LiPF2(Ox)2)-0.5-(VC)-1 | (1C-1) | 0.01 | LiPF$_6$ | 1 | LiPF$_2$(C$_2$O$_4$)$_2$, VC | 0.5, 1 |
| (0)-(LiPF2(Ox)2)-0.5-(VC)-1.001 | — | — | LiPF$_6$ | 1 | LiPF$_2$(C$_2$O$_4$)$_2$, VC | 0.5, 1.001 |
| (0)-(13PRS)-0.01-(LiPF2(Ox)2)-0.5-(VC)-1 | — | — | LiPF$_6$ | 1 | 13PRS, LiPF$_2$(C$_2$O$_4$)$_2$, VC | 0.001, 0.5, 1 |
| (1C-4)-0.05-(0) | (1C-4) | 0.05 | LiPF$_6$ | 1 | — | — |
| (0)-(VC)-0.05 | — | — | LiPF$_6$ | 1 | VC | 0.05 |
| (0)-(13PRS)-0.05 | — | — | LiPF$_6$ | 1 | 13PRS | 0.05 |
| (1C-4)-0.05-(LiPF4(Ox))-1-(LiPO2F2)-0.5 | (1C-4) | 0.05 | LiPF$_6$ | 1 | LiPF$_4$(C$_2$O$_4$), LiPO$_2$F$_2$ | 1, 0.5 |
| (0)-(VC)-0.05-(LiPF4(Ox))-1-(LiPO2F2)-0.5 | — | — | LiPF$_6$ | 1 | VC, LiPF$_4$(C$_2$O$_4$), LiPO$_2$F$_2$ | 0.05, 1, 0.5 |
| (0)-(13PRS)-0.05-(LiPF4(Ox))-1-(LiPO2F2)-0.5 | — | — | LiPF$_6$ | 1 | 13PRS, LiPF$_4$(C$_2$O$_4$), LiPO$_2$F$_2$ | 0.05, 1, 0.5 |
| (1C-7)-0.005-(0) | (1C-7) | 0.005 | LiPF$_6$ | 1 | — | — |
| (0)-(VC)-0.005 | — | — | LiPF$_6$ | 1 | VC | 0.005 |
| (0)-(13PRS)-0.005 | — | — | LiPF$_6$ | 1 | 13PRS | 0.005 |
| (1C-7)-0.005-(LiBF2(Ox))-1-(LiN(SO2F)2)-1 | (1C-7) | 0.005 | LiPF$_6$ | 1 | LiBF$_2$(C$_2$O$_4$), LiN(SO$_2$F)$_2$ | 1, 1 |
| (0)-(VC)-0.005-(LiBF2(Ox))-1-(LiN(SO2F)2)-1 | — | — | LiPF$_6$ | 1 | VC, LiBF$_2$(C$_2$O$_4$), LiN(SO$_2$F)$_2$ | 0.005, 1, 1 |
| (0)-(13PRS)-0.005-(LiBF2(Ox))-1-(LiN(SO2F)2)-1 | — | — | LiPF$_6$ | 1 | 13PRS, LiBF$_2$(C$_2$O$_4$), LiN(SO$_2$F)$_2$ | 0.005, 1, 1 |
| (1C-7)-0.005-(Li[FSO2—N=PF2—N—SO2F])-0.05-(LiN(SO2F)(POF2))-1 | (1C-7) | 0.005 | LiPF$_6$ | 1 | Li[FSO2—N=PF2—N—SO2F], LiN(SO$_2$F)(POF$_2$) | 0.05, 1 |
| (0)-(VC)-0.005-(Li[FSO2—N=PF2—N—SO2F])-0.05-(LiN(SO2F)(POF2))-1 | — | — | LiPF$_6$ | 1 | VC, Li[FSO2—N=PF2—N—SO2F], LiN(SO$_2$F)(POF$_2$) | 0.005 0.05, 1 |
| (0)-(13PRS)-0.005-(Li[FSO2—N=PF2—N—SO2F])-0.05-(LiN(SO2F)(POF2))-1 | — | — | LiPF$_6$ | 1 | 13PRS, Li[FSO2—N=PF2—N—SO2F], LiN(SO$_2$F)(POF$_2$) | 0.005, 0.05, 1 |
| (2C-4)-0.5-(LiBF2(Ox))-0.5-(LiPO2F2)-0.5-(VC)-1 | (2C-4) | 0.5 | LiPF$_6$ | 1 | LiBF$_2$(C$_2$O$_4$), LiPO$_2$F$_2$, VC | 0.5, 0.5, 1 |
| (0)-(LiBF2(Ox))-0.5-(LiPO2F2)-0.5-(VC)-1.5 | — | — | LiPF$_6$ | 1 | LiBF$_2$(C$_2$O$_4$), LiPO$_2$F$_2$, VC | 0.5, 0.5, 1.5 |
| (0)-(13PRS)-0.5-(LiBF2(Ox))-0.5-(LiPO2F2)-0.5-(VC)-1 | — | — | LiPF$_6$ | 1 | 13PRS, LiBF$_2$(C$_2$O$_4$), LiPO$_2$F$_2$, VC | 0.5, 0.5, 0.5 1 |
| (1C-11)-0.005-(0) | (1C-11) | 0.005 | LiPF$_6$ | 1 | — | — |
| (1C-11)-0.005-(LiB(Ox)2)-1-(LiN(SO2F)(POF2))-1-(VC)-1-TBB-1.5 | (1C-11) | 0.005 | LiPF$_6$ | 1 | LiB(C$_2$O$_4$)$_2$, LiN(SO$_2$F)(POF$_2$), VC, TBB | 1, 1, 1, 1.5 |
| (0)-(LiB(Ox)2)-1-(LiN(SO2F)(POF2))-1-(VC)-1.005-TBB-1.5 | — | — | LiPF$_6$ | 1 | LiB(C$_2$O$_4$)$_2$, LiN(SO$_2$F)(POF$_2$), VC, TBB | 1, 1, 1.005, 1.5 |
| (0)-(13PRS)-0.005-(LiB(Ox)2)-1-(LiN(SO2F)(POF2))-1-(VC)-1-TBB-1.5 | — | — | LiPF$_6$ | 1 | 13PRS, LiB(C$_2$O$_4$)$_2$, LiN(SO$_2$F)(POF$_2$), VC, TBB | 0.005, 1, 1, 1, 1.5 |
| (1C-11)-0.005-(Li[FSO2—N=PF2—N—SO2F])-0.03-(LiN(SO2F)(POF2))-1-TBB-1.5 | (1C-11) | 0.005 | LiPF$_6$ | 1 | Li[FSO2—N=PF2—N—SO2F], LiN(SO$_2$F)(POF$_2$), TBB | 0.03, 1, 1.5 |
| (0)-(VC)-0.005-(Li[FSO2—N=PF2—N—SO2F])-0.03-(LiN(SO2F)(POF2))-1-TBB-1.5 | — | — | LiPF$_6$ | 1 | VC, Li[FSO2—N=PF2—N—SO2F], LiN(SO$_2$F)(POF$_2$), TBB | 0.005, 0.03, 1, 1.5 |
| (0)-(13PRS)-0.005-(Li[FSO2—N=PF2—N—SO2F])-0.03-(LiN(SO2F)(POF2))-1-TBB-1.5 | — | — | LiPF$_6$ | 1 | 13PRS, Li[FSO2—N=PF2—N—SO2F], LiN(SO$_2$F)(POF$_2$), TBB | 0.005, 0.03, 1, 1.5 |
| (1C-11)-0.01-(0) | (1C-11) | 0.01 | LiPF$_6$ | 1 | | |
| (1C-11)-0.01-(LiPF4(Ox))-1-(LiN(SO2F)(POF2))-1-(LiPO2F2)-0.5-BP-2 | (1C-11) | 0.01 | LiPF$_6$ | 1 | LiPF$_4$(C$_2$O$_4$), LiN(SO$_2$F)(POF$_2$), LiPO$_2$F$_2$, BP | 1, 1, 0.5, 2 |
| (0)-(VC)-0.01-(LiPF4(Ox))-1-(LiN(SO2F)(POF2))-1-(LiPO2F2)-0.5-BP-2 | — | — | LiPF$_6$ | 1 | VC, LiPF$_4$(C$_2$O$_4$), LiN(SO$_2$F)(POF$_2$), LiPO$_2$F$_2$, BP | 0.01, 1, 1, 0.5, 2 |

TABLE 16-continued

| Electrolyte solution No. | Imine compound Type | Imine compound Conc. [mass %] | Solute Type | Solute Conc. [mol/L] | Other solute and additive Compound | Other solute and additive Conc. [mass %] |
|---|---|---|---|---|---|---|
| (0)-(13PRS)-0.01-(LiPF4(Ox))-1-(LiN(SO2F)(POF2)-1-(LiPO2F2)-0.5-BP-2 | — | — | LiPF$_6$ | 1 | 12PRS, LiPF$_4$(C$_2$O$_4$), LiN(SO$_2$F)(POF$_2$), LiPO$_2$F$_2$, BP | 0.01, 1, 1, 0.5, 2 |
| (1S-5)-0.2-(0) | (1S-5) | 0.2 | LiPF$_6$ | 1 | — | — |
| (0)-(VC)-0.2 | — | — | LiPF$_6$ | 1 | VC | 0.2 |
| (0)-(13PRS)-0.2 | — | — | LiPF$_6$ | 1 | 13PRS | 0.2 |
| (1S-5)-0.2-(LiBF4)-1-(LiSO3F)-1-(FEC)-1-CHB-1.5 | (1S-5) | 0.2 | LiPF$_6$ | 1 | LiBF$_4$, LiSO$_3$F, FEC, CHB | 1, 1, 1, 1.5 |
| (0)-(VC)-0.2-(LiBF4)-1-(LiSO3F)-1-(FEC)-1-CHB-1.5 | (1S-5) | 0.2 | LiPF$_6$ | 1 | VC, LiBF$_4$, LiSO$_3$F, FEC, CHB | 0.2, 1, 1, 1, 1.5 |
| (0)-(13PRS)-0.2-(LiBF4)-1-(LiSO3F)-1-(FEC)-1-CHB-1.5 | (1S-5) | 0.2 | LiPF$_6$ | 1 | 13PRS, LiBF$_4$, LiSO$_3$F, FEC, CHB | 0.2, 1, 1, 1, 1.5 |

TABLE 17

| | Electrolyte solution No. | Positive electrode active material | Negative electrode active material | Initial gas amount * [%] | Capacity after storage* [%] |
|---|---|---|---|---|---|
| Example 9-1 | (1C-1)-0.01-(0) | LiNi$_{0.6}$Co$_{0.2}$Mn$_{0.2}$O$_2$ | Graphite | 88 | 101 |
| Comparative Example 9-1a | (0)-(VC)-0.01 | | | 100 | 100 |
| Comparative Example 9-1b | (0)-(13PRS)-0.01 | | | 100 | 100 |
| Example 9-2 | (1C-1)-0.01-(LiPF2(Ox)2)-0.5-(VC)-1 | | | 113 | 111 |
| Comparative Example 9-2a | (0)-(LiPF2(Ox)2)-0.5-(VC)-1.001 | | | 122 | 111 |
| Comparative Example 9-2b | (0)-(13PRS)-0.01-(LiPF2(Ox)2)-0.5-(VC)-1 | | | 125 | 111 |
| Example 10-1 | (1C-4)-0.05-(0) | | | 90 | 100 |
| Comparative Example 10-1a | (0)-(VC)-0.05 | | | 99 | 100 |
| Comparative Example 10-1b | (0)-(13PRS)-0.05 | | | 99 | 100 |
| Example 10-2 | (1C-4)-0.05-(LiPF4(Ox))-1-(LiPO2F2)-0.5 | | | 83 | 116 |
| Comparative Example 10-2a | (0)-(VC)-0.05-(LiPF4(Ox))-1-(LiPO2F2)-0.5 | | | 87 | 116 |
| Comparative Example 10-2b | (0)-(13PRS)-0.05-(LiPF4(Ox))-1-(LiPO2F2)-0.5 | | | 89 | 116 |
| Example 11-1 | (1C-7)-0.005-(0) | | | 87 | 102 |
| Comparative Example 11-1a | (0)-(VC)-0.005 | | | 100 | 100 |
| Comparative Example 11-1b | (0)-(13PRS)-0.005 | | | 100 | 100 |
| Example 11-2 | (1C-7)-0.005-(LiBF2(Ox))-1-(LiN(SO2F)2)-1 | | | 85 | 113 |
| Comparative Example 11-2a | (0)-(VC)-0.005-(LiBF2(Ox))-1-(Li N(SO2F)2)-1 | | | 95 | 113 |
| Comparative Example 11-2b | (0)-(13PRS)-0.005-(LiBF2(Ox))-1-(LiN(SO2F)2)-1 | | | 95 | 113 |
| Example 11-3 | (1C-7)-0.005-(Li[FSO2—N=PF2—N—SO2F])-0.05-(LiN(SO2F)(POF2))-1 | | | 84 | 114 |
| Comparative Example 11-3a | (0)-(VC)-0.005-(Li[FSO2—N=PF2—N—SO2F])-0.05-(LiN(SO2F)(POF2))-1 | | | 96 | 112 |
| Comparative Example 11-3b | (0)-(13PRS)-0.005-(Li[FSO2—N=PF2—N—SO2F])-0.05-(LiN(SO2F)(POF2))-1 | | | 95 | 112 |
| Example 12-1 | (2C-4)-0.5-(0) | | | 78 | 106 |
| Comparative Example 12-1a | (0)-(VC)-0.5 | | | 95 | 103 |
| Comparative Example 12-1b | (0)-(13PRS)-0.5 | | | 93 | 101 |
| Example 12-2 | (2C-4)-0.5-(LiBF2(Ox))-0.5-(LiPO2F2)-0.5-(VC)-1 | | | 74 | 125 |
| Comparative Example 12-2a | (0)-(LiBF2(Ox))-0.5-(LiPO2F2)-0.5-(VC)-1.5 | | | 87 | 118 |
| Comparative Example 12-2b | (0)-(13PRS)-0.5-(LiBF2(Ox))-0.5-(LiPO2F2)-0.5-(VC)-1 | | | 89 | 117 |
| Example 13-1 | (1C-11)-0.005-(0) | | | 87 | 101 |
| Comparative Example 13-1a | (0)-(VC)-0.005 | | | 100 | 100 |
| Comparative Example 13-1b | (0)-(13PRS)-0.005 | | | 100 | 100 |
| Example 13-2 | (1C-11)-0.005-(LiB(Ox)2)-1-(LiN(SO2F)(POF2)-1-(VC)-1-TBB-1.5 | | | 79 | 129 |
| Comparative Example 13-2a | (0)-(LiB(Ox)2)-1-(LiN(SO2F)(POF2)-1-(VC)-1.005-TBB-1.5 | | | 82 | 125 |
| Comparative Example 13-2b | (0)-(I3PRS)-0.005-(LiB(Ox)2)-1-(LiN(SO2F)(POF2)-1-(VC)-1-TBB-1.5 | | | 82 | 125 |
| Example 13-3 | (1C-11)-0.005-(Li[FSO2—N=PF2—N—SO2F])-0.03-(LiN(SO2F)(POF2))-1-TBB-1.5 | | | 80 | 123 |
| Comparative Example 13-3a | (0)-(VC)-0.005-(Li[FSO2—N=PF2—N—SO2F])-0.03-(LiN(SO2F)(POF2))-1-TBB-1.5 | | | 87 | 116 |
| Comparative Example 13-3b | (0)-(13PRS)-0.005-(Li[FSO2—N=PF2—N—SO2F])-0.03-(LiN(SO2F)(POF2))-1-TBB-1.5 | | | 88 | 115 |
| Example 14-1 | (1C-11)-0.01-(0) | | | 81 | 103 |
| Comparative Example 14-1a | (0)-(VC)-0.01 | | | 100 | 100 |
| Comparative Example 14-1b | (0)-(13PRS)-0.01 | | | 100 | 100 |
| Example 14-2 | (1C-11)-0.01-(LiPF4(Ox))-1-(LiN(SO2F)(POF2)-1-(LiPO2F2)-0.5-BP-2 | | | 74 | 129 |
| Comparative Example 14-2a | (0)-(VC)-0.01-(LiPF4(Ox))-1-(LiN(SO2F)(POF2)-1-(LiPO2F2)-0.5-BP-2 | | | 82 | 124 |
| Comparative Example 14-2b | (0)-(13PRS)-0.01-(LiPF4(Ox))-1-(LiN(SO2F)(POF2)-1-(LiPO2F2)-0.5-Bp-2 | | | 82 | 123 |

TABLE 17-continued

|  | Electrolyte solution No. | Positive electrode active material | Negative electrode active material | Initial gas amount * [%] | Capacity after storage* [%] |
|---|---|---|---|---|---|
| Example 15-1 | (1S-5)-0.2-(0) |  |  | 90 | 104 |
| Comparative Example 15-1a | (0)-(VC)-0.2 |  |  | 98 | 101 |
| Comparative Example 15-1b | (0)-(13PRS)-0.2 |  |  | 97 | 100 |
| Example 15-2 | (1S-5)-0.2-(LiBF4)-1-(LiSO3F)-1-(FEC)-1-CHB-1.5 |  |  | 80 | 113 |
| Comparative Example 15-2a | (0)-(VC)-0.2-(LiBF4)-1-(LiSO3F)-1-(FEC)-1-CHB-1.5 |  |  | 85 | 108 |
| Comparative Example 15-2b | (0)-(13PRS)-0.2-(LiBF4)-1-(LiSO3F)-1-(FEC)-1-CHB-1.5 |  |  | 85 | 106 |
| Comparative Example 1-1 | (0)-(0) |  |  | 100 | 100 |

*Relative values when the result of evaluation of Comparative Example 1-1 was defined as 100.

Incidentally, in the tables, "LiPF2(Ox)2" means $LiPF_2(C_2O_4)_2$, "LiPF4 (Ox)" means $LiPF_4(C_2O_4)$, "LiBF2 (Ox)" means $LiBF_2(C_2O_4)$, "LiB(Ox) 2" means $LiB(C_2O_4)_2$, "LiN(FSO$_2$) (POFpropynyloxy)" means $LiN(FSO_2)$ (POF(OCH$_2$C≡CH)), "FEC" means fluoroethylene carbonate, "13PS" means 1,3-propanesultone, "V4Si" means tetravinylsilane, "TDFEC" means trans-difluoroethylene carbonate, "MMDS" means methylene methanedisulfonate, "12EDSAA" means 1,2-ethanedisulfonic acid anhydride, "EEC" means ethynylethylene carbonate, "DICH" means 1,6-diisocyanatohexane, "SN" means succinonitrile, "EPFCTP" means (ethoxy) pentafluorocyclotriphosphazene, "TBB" means t-butylbenzen, "BP" means biphenyl, and "CHB" means cyclohexylbenzene.

Examples and Comparative Examples Having Variously Modified Negative Electrode Bodies Batteries having compositions in which the electrolyte solution and the negative electrode body were variously modified as shown in Tables 18 to 20 were produced and were evaluated as described above.

TABLE 18

|  | Electrolyte solution No. | Positive electrode active material | Negative electrode active material | Initial gas amount* [%] | Capacity after storage* [%] |
|---|---|---|---|---|---|
| Example 16-1 | (1C-1)-0.5-(0) | $LiNi_{0.6}Co_{0.2}Mn_{0.2}O_2$ | $Li_4Ti_5O_{12}$ | 76 | 106 |
| Comparative Example 16-1a | (0)-(VC)-0.5 |  |  | 90 | 101 |
| Comparative Example 16-1b | (0)-(13PRS)-0.5 |  |  | 92 | 103 |
| Example 16-2 | (1C-1)-0.5-(LiPF2(Ox)2)-1 |  |  | 95 | 102 |
| Comparative Example 16-2a | (0)-(VC)-0.5-(LiPF2(Ox)2)-1 |  |  | 100 | 100 |
| Comparative Example 16-2b | (0)-(13PRS)-0.5-(LiPF2(Ox)2)-1 |  |  | 100 | 100 |
| Example 16-3 | (1C-1)-0.5-(LiPF4(Ox))-1 |  |  | 79 | 108 |
| Comparative Example 16-3a | (0)-(VC)-0.5-(LiPF4(Ox))-1 |  |  | 93 | 103 |
| Comparative Example 16-3b | (0)-(13PRS)-0.5-(LiPF4(Ox))-1 |  |  | 93 | 105 |
| Comparative Example 16-0 | (0)-(0) |  |  | 100 | 101 |

*Relative values when the result of evaluation of Comparative Example 16-0 was defined as 100.

TABLE 19

|  | Electrolyte solution No. | Positive electrode active material | Negative electrode active material | Initial gas amount * [%] | Capacity after storage* [%] |
|---|---|---|---|---|---|
| Example 17-1 | (1C-7)-0.001-(0) | $LiNi_{0.6}Co_{0.2}Mn_{0.2}O_2$ | Graphite (containing silicon) | 90 | 101 |
| Comparative Example 17-1a | (0)-(VC)-0.001 |  |  | 100 | 100 |
| Comparative Example 17-1b | (0)-(13PRS)-0.001 |  |  | 100 | 100 |
| Example 17-2 | (2C-4)-1-(0) |  |  | 72 | 109 |
| Comparative Example 17-2a | (0)-(VC)-1 |  |  | 87 | 105 |
| Comparative Example 17-2b | (0)-(13PRS)-1 |  |  | 90 | 104 |
| Example 17-3 | (1C-11)-0.5-(LiPF2(Ox)2)-1 |  |  | 126 | 129 |
| Comparative Example 17-3a | (0)-(VC)-0.5-(LiPF2(Ox)2)-1 |  |  | 145 | 121 |
| Comparative Example 17-3b | (0)-(13PRS)-0.5-(LiPF2(Ox)2)-1 |  |  | 149 | 120 |
| Example 17-4 | (1S-5)-0.5-(LiPF2(Ox)2)-1 |  |  | 118 | 127 |
| Comparative Example 17-4a | (0)-(VC)-0.5-(LiPF2(Ox)2)-1 |  |  | 145 | 121 |
| Comparative Example 17-4b | (0)-(13PRS)-0.5-(LiPF2(Ox)2)-1 |  |  | 149 | 120 |
| Example 17-5 | (1S-5)-0.5-(LiPF4(Ox))-1 |  |  | 77 | 127 |

TABLE 19-continued

| | Electrolyte solution No. | Positive electrode active material | Negative electrode active material | Initial gas amount * [%] | Capacity after storage* [%] |
|---|---|---|---|---|---|
| Comparative Example 17-5a | (0)-(VC)-0.5-(LiPF4(Ox))-1 | | | 90 | 120 |
| Comparative Example 17-5b | (0)-(13PRS)-0.5-(LiPF4(Ox))-1 | | | 89 | 116 |
| Example 17-6 | (1C-7)-0.5-(LiPO2F2)-1 | | | 75 | 120 |
| Comparative Example 17-6a | (0)-(VC)-0.5-(LiPO2F2)-1 | | | 89 | 113 |
| Comparative Example 17-6b | (0)-(13PRS)-0.5-(LiPO2F2)-1 | | | 91 | 111 |
| Example 17-7 | (1C-7)-0.5-(LiN(SO2F)(POF2))-1 | | | 70 | 130 |
| Comparative Example 17-7a | (0)-(VC)-0.5-(LiN(SO2F)(POF2))-1 | | | 84 | 123 |
| Comparative Example 17-7b | (0)-(13PRS)-0.5-(LiN(SO2F)(POF2))-1 | | | 86 | 125 |
| Example 17-8 | (1C-11)-0.005-(LiB(Ox)2)-1-(LiN(SO2F)(POF2)-1-(VC)-1-TBB-1.5 | | | 79 | 128 |
| Comparative Example 17-8a | (0)-(LiB(Ox)2)-1-(LiN(SO2F)(POF2)-1-(VC)-1.005-TBB-1.5 | | | 84 | 126 |
| Comparative Example 17-8b | (0)-(13PRS)-0.005-(LiB(Ox)2)-1-(LiN(SO2F)(POF2)-1-(VC)-1-TBB-1.5 | | | 84 | 127 |
| Comparative Example 17-0 | (0)-(0) | | | 100 | 100 |

*Relative values when the result of evaluation of Comparative Example 17-0 was defined as 100.

TABLE 20

| | Electrolyte solution No. | Positive electrode active material | Negative electrode active material | Initial gas amount * [%] | Capacity after storage* [%] |
|---|---|---|---|---|---|
| Example 18-1 | (1S-5)-1-(0) | $LiNi_{0.6}Co_{0.2}Mn_{0.2}O_2$ | Hard carbon | 82 | 108 |
| Comparative Example 18-1a | (0)-(VC)-1 | | | 89 | 104 |
| Comparative Example 18-1b | (0)-(13PRS)-1 | | | 91 | 103 |
| Example 18-2 | (1C-7)-0.5-(LiPF2(Ox)2)-1 | | | 120 | 121 |
| Comparative Example 18-2a | (0)-(VC)-0.5-(LiPF2(Ox)2)-1 | | | 148 | 116 |
| Comparative Example 18-2b | (0)-(13PRS)-0.5-(LiPF2(Ox)2)-1 | | | 145 | 112 |
| Example 18-3 | (1C-1)-0.01-(LiPF2(Ox)2)-0.5-(VC)-1.01 | | | 119 | 113 |
| Comparative Example 18-3a | (0)-(LiPF2(Ox)2)-0.5-(VC)-1.01 | | | 125 | 113 |
| Comparative Example 18-3b | (0)-(13PRS)-0.01-(LiPF2(Ox)2)-0.5-(VC)-1.01 | | | 126 | 113 |
| Example 18-4 | (1C-11)-0.005-(LiB(Ox)2)-1-(LiN(SO2F)(POF2)-1-(VC)-1-TBB-1.5 | | | 80 | 132 |
| Comparative Example 18-4a | (0)-(LiB(Ox)2)-1-(LiN(SO2F)(POF2)-1-(VC)-1.005-TBB-1.5 | | | 89 | 127 |
| Comparative Example 18-4b | (0)-(13PRS)-0.005-(LiB(Ox)2)-1-(LiN(SO2F)(POF2)-1-(VC)-1-TBB-1.5 | | | 89 | 126 |
| Comparative Example 18-0 | (0)-(0) | | | 100 | 100 |

*Relative values when the result of evaluation of Comparative Example 18-0 was defined as 100.

Incidentally, a negative electrode body whose negative electrode active material is $Li_4Ti_5O_{12}$ was produced by mixing a $Li_4Ti_5O_{12}$ powder (90 mass %) with PVDF (5 mass %) as a binder and acetylene black (5 mass %) as a conductive agent, further adding NMP to the mixture, applying the resultant paste onto copper foil, and drying it. In the evaluation of the battery, the charge termination voltage was 2.7 V, and the discharge termination voltage was 1.5 V.

A negative electrode body whose negative electrode active material is graphite (containing silicon) was produced by mixing a graphite powder (80 mass %) with a silicon powder (10 mass %) and PVDF (10 mass %) as a binder, further adding NMP to the mixture, applying the resultant paste onto copper foil, and drying it. In the evaluation of the battery, the charge termination voltage and the discharge termination voltage were the same as those in Example 1-1.

A negative electrode body whose negative electrode active material is hard carbon was produced by mixing hard carbon (90 mass %) with PVDF (5 mass %) as a binder and acetylene black (5 mass %) as a conductive agent, further adding NMP to the mixture, applying the resultant paste onto copper foil, and drying it. In the evaluation of the battery, the charge termination voltage was 4.2 V, and the discharge termination voltage was 2.2 V.

Also, for every electrode composition using $Li_4Ti_5O_{12}$, graphite (containing silicon), or hard carbon as the negative electrode active material as described above, it was confirmed that the initial gas generation amount can be suppressed by using the electrolyte solution having the composition containing the imine compound having the specific structure of the present invention, as compared with the comparative examples using the conventional electrolyte solutions having the compositions containing vinylene carbonate or unsaturated sultone. Accordingly, the non-aqueous-electrolyte solution battery that can suppress the initial gas generation amount was obtained by using the electrolyte solution having the composition containing the imine compound having the specific structure of the present invention, regardless of the type of the negative electrode active material In addition, for all the Examples shown in Tables 18 to 20, it was confirmed that the suppression of the initial gas generation amount and the 70° C. durability performance can be exhibited in a well-balanced manner.

Examples and Comparative Examples Having Variously Modified Positive Electrode Bodies Batteries having the compositions in which the electrolyte solution and the positive electrode body were variously modified as shown in Tables 21 to 24 were produced and were evaluated as described above.

TABLE 21

| | Electrolyte solution No. | Positive electrode active material | Negative electrode active material | Initial gas amount* [%] | Capacity after storage* [%] |
|---|---|---|---|---|---|
| Example 19-1 | (1C-4)-0.5-(0) | LiCoO$_2$ | Graphite | 79 | 105 |
| Comparative Example 19-1a | (0)-(VC)-0.5 | | | 92 | 105 |
| Comparative Example 19-1b | (0)-(13PRS)-0.5 | | | 91 | 102 |
| Example 19-2 | (1C-7)-0.001-(0) | | | 94 | 102 |
| Comparative Example 19-2a | (0)-(VC)-0.001 | | | 100 | 100 |
| Comparative Example 19-2b | (0)-(13PRS)-0.001 | | | 100 | 100 |
| Example 19-3 | (1S-5)-1-(0) | | | 81 | 109 |
| Comparative Example 19-3a | (0)-(VC)-1 | | | 88 | 105 |
| Comparative Example 19-3b | (0)-(13PRS)-1 | | | 89 | 106 |
| Example 19-4 | (1C-7)-0.5-(LiN(SO2F)(POF2))-1 | | | 77 | 123 |
| Comparative Example 19-4a | (0)-(VC)-0.5-(LiN(SO2F)(POF2))-1 | | | 86 | 116 |
| Comparative Example 19-4b | (0)-(13PRS)-0.5-(LiN(SO2F)(POF2))-1 | | | 86 | 113 |
| Example 19-5 | (1C-11)-0.5-(LiN(SO2F)(POF2))-1 | | | 76 | 126 |
| Comparative Example 19-5a | (0)-(VC)-0.5-(LiN(SO2F)(POF2))-1 | | | 86 | 116 |
| Comparative Example 19-5b | (0)-(13PRS)-0.5-(LiN(SO2F)(POF2))-1 | | | 86 | 113 |
| Comparative Example 19-0 | (0)-(0) | | | 100 | 100 |

*Relative values when the result of evaluation of Comparative Example 19-0 was defined as 100.

TABLE 22

| | Electrolyte solution No. | Positive electrode active material | Negative electrode active material | Initial gas amount* [%] | Capacity after storage* [%] |
|---|---|---|---|---|---|
| Example 20-1 | (1C-7)-0.001-(0) | LiN$_{0.8}$Co$_{0.15}$Mn$_{0.05}$O$_2$ | Graphite | 92 | 101 |
| Comparative Example 20-1a | (0)-(VC)-0.001 | | | 100 | 100 |
| Comparative Example 20-1b | (0)-(13PRS)-0.001 | | | 100 | 100 |
| Example 20-2 | (2C-4)-1-(0) | | | 70 | 109 |
| Comparative Example 20-2a | (0)-(VC)-1 | | | 88 | 105 |
| Comparative Example 20-2b | (0)-(13PRS)-1 | | | 92 | 103 |
| Example 20-3 | (1C-11)-0.5-(LiPF2(Ox)2)-1 | | | 118 | 127 |
| Comparative Example 20-3a | (0)-(VC)-0.5-(LiPF2(Ox)2)-1 | | | 139 | 119 |
| Comparative Example 20-3b | (0)-(13PRS)-0.5-(LiPF2(Ox)2)-1 | | | 137 | 117 |
| Example 20-4 | (1S-5)-0.5-(LiPF2(Ox)2)-1 | | | 119 | 129 |
| Comparative Example 20-4a | (0)-(VC)-0.5-(LiPF2(Ox)2)-1 | | | 139 | 119 |
| Comparative Example 20-4b | (0)-(13PRS)-0.5-(LiPF2(Ox)2)-1 | | | 137 | 117 |
| Example 20-5 | (1S-5)-0.5-(LiPF4(Ox))-1 | | | 73 | 126 |
| Comparative Example 20-5a | (0)-(VC)-0.5-(LiPF4(Ox))-1 | | | 88 | 118 |
| Comparative Example 20-5b | (0)-(13PRS)-0.5-(LiPF4(Ox))-1 | | | 87 | 117 |
| Example 20-6 | (1C-7)-0.5-(LiPO2F2)-1 | | | 71 | 119 |
| Comparative Example 20-6a | (0)-(VC)-0.5-(LiPO2F2)-1 | | | 85 | 111 |

TABLE 22-continued

| | Electrolyte solution No. | Positive electrode active material | Negative electrode active material | Initial gas amount* [%] | Capacity after storage* [%] |
|---|---|---|---|---|---|
| Comparative Example 20-6b | (0)-(13PRS)-0.5-(LiPO2F2)-1 | | | 87 | 106 |
| Example 20-7 | (1C-7)-0.5-(LiN(SO2F)(POF2))-1 | | | 70 | 131 |
| Comparative Example 20-7a | (0)-(VC)-0.5-(LiN(SO2F)(POF2))-1 | | | 85 | 125 |
| Comparative Example 20-7b | (0)-(13PRS)-0.5-(LiN(SO2F)(POF2))-1 | | | 87 | 122 |
| Example 20-8 | (1C-1)-0.005-(LiB(Ox)2-1-(LiN(SO2F)(POF2)-1-(VC)-1-TBB-1.5 | | | 76 | 128 |
| Comparative Example 20-8a | (0)-(LiB(Ox)2-1-(LiN(SO2F)(POF2)-1-(VC)-1.005-TBB-1.5 | | | 82 | 126 |
| Comparative Example 20-8b | (0)-(13PRS)-0.005-(LiB(Ox)2-1-(LiN(SO2F)(POF2)-1-(VC)-1-TBB-1.5 | | | 82 | 126 |
| Comparative Example 20-0 | (0)-(0) | | | 100 | 100 |

*Relative values when the result of evaluation of Comparative Example 20-0 was defined as 100.

TABLE 23

| | Electrolyte solution No. | Positive electrode active material | Negative electrode active material | Initial gas amount* [%] | Capacity after storage* [%] |
|---|---|---|---|---|---|
| Example 21-1 | (1C-1)-0.01-(LiPF2(Ox)2)-0.5-(VC)-1 | LiMn₂O₄ | Graphite | 117 | 117 |
| Comparative Example 21-1a | (0)-(LiPF2(Ox)2)-0.5-(VC)-1.01 | | | 124 | 117 |
| Comparative Example 21-1b | (0)-(13PRS)-0.01-(LiPF2(Ox)2)-0.5-(VC)-1 | | | 124 | 117 |
| Example 21-2 | (1C-11)-0.005-(LiB(Ox)2)-1-(LiN(SO2F)(POF2)-1-(VC)-1-TBB-1.5 | | | 84 | 128 |
| Comparative Example 21-2a | (0)-(LiB(Ox)2)-1-(LiN(SO2F)(POF2)-1-(VC)-1.005-TBB-1.5 | | | 92 | 128 |
| Comparative Example 21-2b | (0)-(13PRS)-0.005-(LiB(Ox)2)-1-(LiN(SO2F)(POF2)-1-(VC)-1-TBB-1.5 | | | 92 | 128 |
| Comparative Example 21-0 | (0)-(0) | | | 100 | 100 |

*Relative values when the result of evaluation of Comparative Example 21-0 was defined as 100.

TABLE 24

| | Electrolyte solution No. | Positive electrode active material | Negative electrode active material | Initial gas amount* [%] | Capacity after storage* [%] |
|---|---|---|---|---|---|
| Example 22-1 | (1C-1)-0.01-(LiPF2(Ox)2)-0.5-(VC)-1 | LiFePO₄ | Graphite | 113 | 122 |
| Comparative Example 22-1a | (0)-(LiPF2(Ox)2)-0.5-(VC)-1.01 | | | 119 | 122 |
| Comparative Example 22-1b | (0)-(13PRS)-0.01-(LiPF2(Ox)2)-0.5-(VC)-1 | | | 119 | 122 |
| Example 22-2 | (1C-11)-0.005-(LiB(Ox)2)-1-(LiN(SO2F)(POF2)-1-(VC)-1-TBB-1.5 | | | 79 | 132 |
| Comparative Example 22-2a | (0)-(LiB(Ox)2)-1-(LiN(SO2F)(POF2)-1-(VC)-1.005-TBB-1.5 | | | 87 | 130 |
| Comparative Example 22-2b | (0)-(13PRS)-0.005-(LiB(Ox)2)-1-(LiN(SO2F)(POF2)-1-(VC)-1-TBB-1.5 | | | 87 | 130 |
| Comparative Example 22-0 | (0)-(0) | | | 100 | 100 |

*Relative values when the result of evaluation of Comparative Example 22-0 was defined as 100.

Incidentally, a positive electrode body whose positive electrode active material is LiCoO₂ was produced by mixing a LiCoO₂ powder (90 mass %) with PVDF (5 mass %) as a binder and acetylene black (5 mass %) as a conductive material, further adding NMP to the mixture, applying the resultant paste onto aluminum foil, and drying it. In the evaluation of the battery, the charge termination voltage was 4.2 V, and the discharge termination voltage was 3.0 V.

A positive electrode body whose positive electrode active material is $LiNi_{0.8}Co_{0.15}Al_{0.05}O_2$ was produced by mixing a $LiNi_{0.8}Co_{0.15}Al_{0.05}O_2$ powder (90 mass %) with PVDF (5 mass %) as a binder and acetylene black (5 mass %) as a conductive material, further adding NMP to the mixture, applying the resultant paste onto aluminum foil, and drying it. In the evaluation of the battery, the charge termination voltage was 4.2 V, and the discharge termination voltage was 3.0 V.

A positive electrode body whose positive electrode active material is $LiMn_2O_4$ was produced by mixing a $LiMn_2O_4$ powder (90 mass %) with PVDF (5 mass %) as a binder and acetylene black (5 mass %) as a conductive material, further adding NMP to the mixture, applying the resultant paste onto aluminum foil, and drying it. In the evaluation of the battery, the charge termination voltage was 4.2 V, and the discharge termination voltage was 3.0 V.

A positive electrode body whose positive electrode active material is $LiFePO_4$ was produced by mixing a $LiFePO_4$ powder coated with amorphous carbon (90 mass %) with PVDF (5 mass %) as a binder and acetylene black (5 mass %) as a conductive material, further adding NMP to the mixture, applying the resultant paste onto aluminum foil, and drying it. In the evaluation of the battery, the charge termination voltage was 4.1 V, and the discharge termination voltage was 2.5 V.

Also, for every electrode composition using $LiCoO_2$, $LiNi_{0.8}Co_{0.15}Al_{0.05}O_2$, $LiMn_2O_4$, or $LiFePO_4$ as the positive electrode active material as described above, it was confirmed that the initial gas generation amount can be suppressed by using the electrolyte solution having the composition containing the imine compound having the specific structure of the present invention, as compared with the comparative examples using the conventional electrolyte solutions having the compositions containing vinylene carbonate or unsaturated sultone. Accordingly, the non-aqueous-electrolyte solution battery that can suppress the initial gas generation amount was obtained by using the electrolyte solution having the composition containing the imine compound having the specific structure of the present invention, regardless of the type of the positive electrode active material.

In addition, for all the examples shown in Tables 21 to 24, it was confirmed that the suppression of the initial gas generation amount and the 70° C. durability performance can be exhibited in a well-balanced manner.

Sodium Ion Battery

Example 23-1

Preparation of Electrolyte Solution

Electrolyte solution No. Na(1C-7)-1-(0) for a non-aqueous electrolyte solution battery was prepared by using a mixed solvent of propylene carbonate, ethylene carbonate, and diethyl carbonate at a volume ratio of 2:2:6 as a non-aqueous solvent and dissolving $NaPF_6$ as a solute and Compound (1C-7) as the imine compound in the solvent such that the concentration of $NaPF_6$ was 1.0 mol/L and that the concentration of Compound (1C-7) (the content of Cl in the imine compound as a raw material before being dissolved in the electrolyte solution was 10 mass ppm) was 1.0 mass % based on the total amount of the non-aqueous solvent, the solute, and the imine compound. The above preparation was performed while maintaining the solution temperature at 25° C. The conditions for preparing the non-aqueous electrolyte solution are shown in Table 25.

Production of Battery

A battery was produced as in Example 1C-1 except that the above electrolyte solution was used, the positive electrode material was $NaFe_{0.5}Co_{0.5}O_2$, and the negative electrode material was hard carbon, and the battery was evaluated as in Example 1C-1. Incidentally, a positive electrode body whose positive electrode active material is $NaFe_{0.5}Co_{0.5}O_2$ was produced by mixing a $NaFe_{0.5}Co_{0.5}O_2$ powder (90 mass %) with PVDF (5 mass %) as a binder and acetylene black (5 mass %) as a conductive material, further adding NMP to the mixture, applying the resultant paste onto aluminum foil, and drying it. In the evaluation of the battery, the charge termination voltage was 3.8 V, and the discharge termination voltage was 1.5 V.

The results of evaluation of the batteries are shown in Table 26. Incidentally, the values of the gas generation amount and 70° C. durability performance of the batteries in Table 26 are relative values when the gas generation amount after initial charge and discharge and the discharge capacity after a 70° C. storage test of a laminated battery produced using the electrolyte solution No. Na(0)-(0) described below were each defined as 100.

TABLE 25

| Electrolyte solution No. | Imine compound | | Solute | | Other solute and additive | |
|---|---|---|---|---|---|---|
| | Type | Conc. [mass %] | Type | Conc. [mol/L] | Compound | Conc. [mass %] |
| Na(1C-7)-1-(0) | (1C-7) | 1 | $NaPF_6$ | 1 | — | — |
| Na(0)-(FEC)-1 | — | — | $NaPF_6$ | 1 | FEC | 1 |
| Na(1C-11)-1-(0) | (1C-11) | 1 | $NaPF_6$ | 1 | — | — |
| Na(2C-1)-1-(0) | (2C-1) | 1 | $NaPF_6$ | 1 | — | — |
| Na(1S-4)-1-(0) | (1S-4) | 1 | $NaPF_6$ | 1 | — | — |
| Na(1S-5)-1-(0) | (1S-5)— | 1 | $NaPF_6$ | 1 | — | — |
| Na(3C-9)-1-(0) | (3C-9) | 1 | $NaPF_6$ | 1 | — | — |
| Na(3S-1)-1-(0) | (3S-1) | 1 | $NaPF_6$ | 1 | — | — |
| Na(1C-7)-1-(NaPF4(Ox))-1 | (1C-7) | 1 | $NaPF_6$ | 1 | $NaPF_4(C_2O_4)$ | 1 |
| Na(0)-(FEC)-1-(NaPF4(Ox))-1 | — | — | $NaPF_6$ | 1 | FEC, $NaPF_4(C_2O_4)$ | 1, 1 |
| Na(1C-11)-1-(NaPF4(Ox))-1 | (1C-11) | 1 | $NaPF_6$ | 1 | $NaPF_4(C_2O_4)$ | 1 |
| Na(2C-1)-1-(NaPF4(Ox))-1 | (2C-1) | 1 | $NaPF_6$ | 1 | $NaPF_4(C_2O_4)$ | 1 |
| Na(1S-5)-1-(NaPF4(Ox))-1 | (1S-5) | 1 | $NaPF_6$ | 1 | $NaPF_4(C_2O_4)$ | 1 |
| Na(1C-7)-1-(NaN(SO2F)(POF2))-1 | (1C-7) | 1 | $NaPF_6$ | 1 | $NaN(SO_2F)(POF_2)$ | 1 |
| Na(0)-(FEC)-1-(NaN(SO2F)(POF2))-1 | — | — | $NaPF_6$ | 1 | FEC, $NaN(SO_2F)(POF_2)$ | 1, 1 |
| Na(1C-11)-1-(NaN(SO2F)(POF2))-1 | (1C-11) | 1 | $NaPF_6$ | 1 | $NaN(SO_2F)(POF_2)$ | 1 |
| Na(2C-1)-1-(NaN(SO2F)(POF2))-1 | (2C-1) | 1 | $NaPF_6$ | 1 | $NaN(SO_2F)(POF_2)$ | 1 |

TABLE 25-continued

| Electrolyte solution No. | Imine compound Type | Conc. [mass %] | Solute Type | Conc. [mol/L] | Other solute and additive Compound | Conc. [mass %] |
|---|---|---|---|---|---|---|
| Na(1S-5)-1-(NaN(SO2F)(POF2))-1 | (1S-5) | 1 | NaPF$_6$ | 1 | NaN(SO$_2$F)(POF$_2$) | 1 |
| Na(1C-7)-1-(NaN(FSO2)2)-1 | (1C-7) | 1 | NaPF$_6$ | 1 | NaN(FSO$_2$)$_2$ | 1 |
| Na(0)-(FEC)-1-(NaN(FSO2)2)-1 | — | — | NaPF$_6$ | 1 | FEC, NaN(FSO$_2$)$_2$ | 1, 1 |
| Na(1C-11)-1-(NaN(FSO2)2)-1 | (1C-11) | 1 | NaPF$_6$ | 1 | NaN(FSO$_2$)$_2$ | 1 |
| Na(2C-1)-1-(NaN(FSO2)2)-1 | (2C-1) | 1 | NaPF$_6$ | 1 | NaN(FSO$_2$)$_2$ | 1 |
| Na(1S-5)-1-(NaN(FSO2)2)-1 | (1S-5) | 1 | NaPF$_6$ | 1 | NaN(FSO$_2$)$_2$ | 1 |
| Na(1C-7)-1-(FEC)-2 | (1C-7) | 1 | NaPF$_6$ | 1 | FEC | 2 |
| Na(0)-(FEC)-3 | — | — | NaPF$_6$ | 1 | FEC | 3 |
| Na(1C-11)-1-(FEC)-2 | (1C-11) | 1 | NaPF$_6$ | 1 | FEC | 2 |
| Na(2C-1)-1-(FEC)-2 | (2C-1) | 1 | NaPF$_6$ | 1 | FEC | 2 |
| Na(1S-5)-1-(FEC)-2 | (1S-5) | 1 | NaPF$_6$ | 1 | FEC | 2 |
| Na(0)-(0) | — | — | NaPF$_6$ | 1 | — | — |

TABLE 26

| | Electrolyte solution No. | Positive electrode active material | Negative electrode active material | Initial gas amount* [%] | Capacity after storage* [%] |
|---|---|---|---|---|---|
| Example 23-1 | Na(1C-7)-1-(0) | NaF$_{0.5}$Co$_{0.5}$O$_2$ | Hard carbon | 90 | 113 |
| Comparative Example 23-1 | Na(0)-(FEC)-1 | | | 97 | 108 |
| Example 23-2 | Na(1C-11)-1-(0) | | | 81 | 115 |
| Comparative Example 23-2 | Na(0)-(FEC)-1 | | | 97 | 108 |
| Example 23-3 | Na(2C-1)-1-(0) | | | 89 | 110 |
| Comparative Example 23-3 | Na(0)-(FEC)-1 | | | 97 | 108 |
| Example 23-4 | Na(1S-4)-1-(0) | | | 83 | 109 |
| Comparative Example 23-4 | Na(0)-(FEC)-1 | | | 97 | 108 |
| Example 23-5 | Na(1S-5)-1-(0) | | | 88 | 114 |
| Comparative Example 23-5 | Na(0)-(FEC)-1 | | | 97 | 108 |
| Example 23-6 | Na(3C-9)-1-(0) | | | 80 | 110 |
| Comparative Example 23-6 | Na(0)-(FEC)-1 | | | 97 | 108 |
| Example 23-7 | Na(3S-1)-1-(0) | | | 85 | 110 |
| Comparative Example 23-7 | Na(0)-(FEC)-1 | | | 97 | 108 |
| Comparative Example 23-0 | Na(0)-(0) | | | 100 | 100 |

*Relative values when the result of evaluation of Comparative Example 23-0 was defined as 100.

[Examples 23-2 to 23-7, 24-1 to 24-8, and 25-1 to 25-8 and Comparative Examples 23-1 to 23-7, 24-1 to 24-8, and 25-1 to 25-8]

The electrolyte solutions according to the examples and comparative examples shown in Tables 26 to 28 were each prepared in the same manner as that in Electrolyte solution No. Na(1C-7)-1-(0), except that the type and the concentration of the imine compounds and the types and the concentrations of other solutes and additives were changed as shown in Table 25.

Batteries having the electrode compositions shown in Tables 26 to 28 were produced using the resultant electrolyte solutions in the same manner as that in Example 23-1, and were evaluated as described above.

Incidentally, a positive electrode body whose positive electrode active material is NaFe$_{0.4}$Ni$_{0.3}$Mn$_{0.3}$O$_2$ was produced by mixing a NaFe$_{0.4}$Ni$_{0.3}$Mn$_{0.3}$O$_2$ powder (90 mass %) with PVDF (5 mass %) as a binder and acetylene black (5 mass %) as a conductive material, further adding NMP to the mixture, applying the resultant paste onto aluminum foil, and drying it. In the evaluation of the battery, the charge termination voltage was 4.1 V, and the discharge termination voltage was 2.0 V.

A positive electrode body whose positive electrode active material is NaNi$_{1/3}$Ti$_{1/6}$Mn$_{1/2}$O$_2$ was also produced by mixing a NaNi$_{1/3}$Ti$_{1/6}$Mn$_{1/2}$O$_2$ powder (90 mass %) with PVDF (5 mass %) as a binder and acetylene black (5 mass %) as a conductive material, further adding NMP to the mixture, applying the resultant paste onto aluminum foil, and drying it. In the evaluation of the battery, the charge termination voltage was 4.5 V, and the discharge termination voltage was 1.5 V.

TABLE 27

| | Electrolyte solution No. | Positive electrode active material | Negative electrode active material | Initial gas amount* [%] | Capacity after storage* [%] |
|---|---|---|---|---|---|
| Example 24-1 | Na(1C-7)-1-(NaPF4(Ox))-1 | NaF$_{0.4}$Ni$_{0.3}$Mn$_{0.3}$O$_2$ | Hard carbon | 82 | 120 |
| Comparative Example 24-1 | Na(0)-(FEC)-1-(NaPF4(Ox))-1 | | | 90 | 116 |
| Example 24-2 | Na(1C-11)-1-(NaPF4(Ox))-1 | | | 83 | 121 |
| Comparative Example 24-2 | Na(0)-(FEC)-1-(NaPF4(Ox))-1 | | | 90 | 116 |

TABLE 27-continued

| Electrolyte solution No. | Positive electrode active material | Negative electrode active material | Initial gas amount* [%] | Capacity after storage* [%] |
|---|---|---|---|---|
| Example 24-3 Na(2C-1)-1-(NaPF4(Ox))-1 | | | 82 | 119 |
| Comparative Example 24-3 Na(0)-(FEC)-1-(NaPF4(Ox))-1 | | | 90 | 116 |
| Example 24-4 Na(1S-5)-1-(NaPF4(Ox))-1 | | | 80 | 122 |
| Comparative Example 24-4 Na(0)-(FEC)-1-(NaPF4(Ox))-1 | | | 90 | 116 |
| Example 24-5 Na(1C-7)-1-(NaN(SO2F)(POF2))-1 | | | 82 | 125 |
| Comparative Example 24-5 Na(0)-(FEC)-1-(NaN(SO2F)(POF2))-1 | | | 92 | 117 |
| Example 24-6 Na(1C-11)-1-(NaN(SO2F)(POF2))-1 | | | 80 | 126 |
| Comparative Example 24-6 Na(0)-(FEC)-1-(NaN(SO2F)(POF2))-1 | | | 92 | 117 |
| Example 24-7 Na(2C-1)-1-(NaN(SO2F)(POF2))-1 | | | 80 | 124 |
| Comparative Example 24-7 Na(0)-(FEC)-1-(NaN(SO2F)(POF2))-1 | | | 92 | 117 |
| Example 24-8 Na(1S-5)-1-(NaN(SO2F)(POF2))-1 | | | 79 | 125 |
| Comparative Example 24-8 Na(0)-(FEC)-1-(NaN(SO2F)(POF2))-1 | | | 92 | 117 |
| Comparative Example 24-0 Na(0)-(0) | | | 100 | 100 |

*Relative values when the result of evaluation of Comparative Example 24-0 was defined as 100.

TABLE 28

| Electrolyte solution No. | Positive electrode active material | Negative electrode active material | Initial gas amount* [%] | Capacity after storage* [%] |
|---|---|---|---|---|
| Example 25-1 Na(1C-7)-1-(NaN(FSO2)2)-1 | NaNi$_{1/3}$Ti$_{1/6}$Mn$_{1/2}$O$_2$ | Hard carbon | 88 | 115 |
| Comparative Example 25-1 Na(0)-(FEC)-1-(NaN(FSO2)2)-1 | | | 95 | 111 |
| Example 25-2 Na(1C-11)-1-(NaN(FSO2)2)-1 | | | 79 | 116 |
| Comparative Example 25-2 Na(0)-(FEC)-1-(NaN(FSO2)2)-1 | | | 95 | 111 |
| Example 25-3 Na(2C-1)-1-(NaN(FSO2)2)-1 | | | 87 | 113 |
| Comparative Example 25-3 Na(0)-(FEC)-1-(NaN(FSO2)2)-1 | | | 95 | 111 |
| Example 25-4 Na(1S-5)-1-(NaN(FSO2)2)-1 | | | 85 | 115 |
| Comparative Example 25-4 Na(0)-(FEC)-1-(NaN(FSO2)2)-1 | | | 95 | 111 |
| Example 25-5 Na(1C-7)-1-(FEC)-2 | | | 82 | 119 |
| Comparative Example 25-5 Na(0)-(FEC)-3 | | | 93 | 112 |
| Example 25-6 Na(1C-11)-1-(FEC)-2 | | | 79 | 120 |
| Comparative Example 25-6 Na(0)-(FEC)-3 | | | 93 | 112 |
| Example 25-7 Na(2C-1)-1-(FEC)-2 | | | 83 | 117 |
| Comparative Example 25-7 Na(0)-(FEC)-3 | | | 93 | 112 |
| Example 25-8 Na(1S-5)-1-(FEC)-2 | | | 87 | 120 |
| Comparative Example 25-8 Na(0)-(FEC)-3 | | | 93 | 112 |
| Comparative Example 25-0 Na(0)-(0) | | | 100 | 100 |

*Relative values when the result of evaluation of Comparative Example 25-0 was defined as 100.

It was confirmed from the results shown in Tables 26 to 28 that also for sodium ion batteries, the initial gas generation amount can be suppressed by using the electrolyte solution having the composition containing the imine compound having the specific structure of the present invention, as compared with the comparative examples using the conventional electrolyte solutions having the compositions containing fluoroethylene carbonate. Accordingly, even for the sodium ion batteries, the non-aqueous-electrolyte solution battery that can suppress the initial gas generation amount was obtained by using the electrolyte solution having the composition containing the imine compound having the specific structure of the present invention.

In addition, for all of the examples shown in Tables 26 to 28, it was confirmed that the suppression of the initial gas generation amount and the 70° C. durability performance can be exhibited in a well-balanced manner.

What is claimed is:

1. An electrolyte solution for a non-aqueous electrolyte solution battery, comprising a non-aqueous solvent, a solute, and an additive for a non-aqueous electrolyte solution, wherein the additive is represented by any one of formula [1], formula [2], formula [3], and formula [4]:

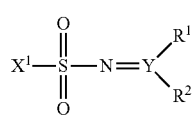
[1]

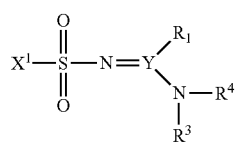
[2]

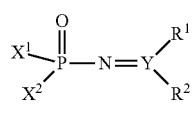
[3]

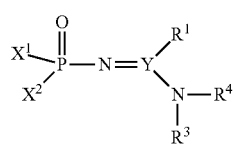
[4]

wherein, in the formula [1], formula [2], formula [3], and formula [4], $X^1$ and $X^2$ are each independently a fluorine atom or an organic group selected from the group consisting of a linear or branched alkyl group having 1 to 10 carbon atoms, a linear or branched alkoxy group having 1 to 10 carbon atoms, a linear or branched alkenyl group having 2 to 10 carbon atoms, a linear or branched alkenyloxy group having 2 to 10 carbon atoms, a linear or branched alkynyl group having 2 to 10 carbon atoms, a linear or branched alkynyloxy group having 2 to 10 carbon atoms, a cycloalkyl group having 3 to 10 carbon atoms, a cycloalkoxy group having 3 to 10 carbon atoms, a cycloalkenyl group having 3 to 10 carbon atoms, a cycloalkenyloxy group having 3 to 10 carbon atoms, an aryl group having 6 to 10 carbon atoms, and an aryloxy group having 6 to 10 carbon atoms, wherein the organic group optionally contains a fluorine atom, an oxygen atom, or an unsaturated bond;

Y is a carbon atom or a sulfur atom;

$R^1$ and $R^2$ are each independently an organic group selected from the group consisting of a linear or branched alkyl group having 1 to 10 carbon atoms, a linear or branched alkoxy group having 1 to 10 carbon atoms, a linear or branched alkenyl group having 2 to 10 carbon atoms, a linear or branched alkenyloxy group having 2 to 10 carbon atoms, a linear or branched alkynyl group having 2 to 10 carbon atoms, a linear or branched alkynyloxy group having 2 to 10 carbon atoms, a cycloalkyl group having 3 to 10 carbon atoms, a cycloalkoxy group having 3 to 10 carbon atoms, a cycloalkenyl group having 3 to 10 carbon atoms, a cycloalkenyloxy group having 3 to 10 carbon atoms, an aryl group having 6 to 10 carbon atoms, and an aryloxy group having 6 to 10 carbon atoms, wherein the organic group optionally contains a fluorine atom, an oxygen atom, or an unsaturated bond;

$R^3$ and $R^4$ are each independently an organic group selected from the group consisting of a linear or branched alkyl group having 1 to 10 carbon atoms, a linear or branched alkenyl group having 2 to 10 carbon atoms, a linear or branched alkynyl group having 2 to 10 carbon atoms, a cycloalkyl group having 3 to 10 carbon atoms, a cycloalkenyl group having 3 to 10 carbon atoms, and an aryl group having 6 to 10 carbon atoms, wherein the organic group optionally contains a fluorine atom, an oxygen atom, or an unsaturated bond; and $R^1$ and $R^2$ or $R^1$ and $R^4$ optionally form together a cyclic structure as shown in formula [5] or formula [6]:

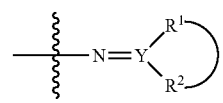
[5]

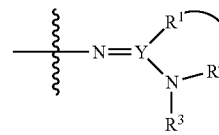
[6]

2. The non-aqueous electrolyte solution according to claim 1, wherein, in the formula [1], formula [2], formula [3], and formula [4], $X^1$ and $X^2$ are each independently a fluorine atom or a group selected from the group consisting of a methyl group, a trifluoromethyl group, and a phenyl group;

at least one of $R^1$ and $R^2$ is a group selected from the group consisting of a methyl group, a methoxy group, an ethyl group, an ethoxy group, a propyl group, a propoxyl group, a vinyl group, an allyl group, an allyloxy group, an ethynyl group, a 2-propynyl group, a 2-propynyloxy group, a phenyl group, and a phenyloxy group; and at least one of $R^3$ and $R^4$ is a group selected from the group consisting of a methyl group, an ethyl group, a propyl group, a vinyl group, an allyl group, an ethynyl group, a 2-propynyl group, and a phenyl group.

3. The non-aqueous electrolyte solution according to claim 1, wherein, in the formula [1], formula [2], formula [3], and formula [4], $X^1$ and $X^2$ are each independently a fluorine atom or a group selected from the group consisting of a methyl group, a trifluoromethyl group, and a phenyl group; and $R^1$ and $R^2$ or $R^1$ and $R^4$ form together a cyclic structure represented by any one of formula [7], formula [8], formula [9], formula [10], and formula [11]:

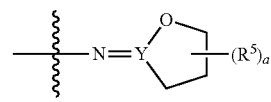
[7]

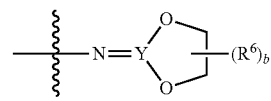
[8]

-continued

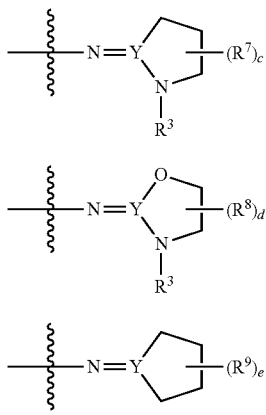

wherein, in the formula [7], formula [8], formula [9], formula [10], and formula [11], $R^5$, $R^6$, $R^7$, $R^8$ and $R^9$ are each independently a fluorine atom or an organic group selected from the group consisting of a linear or branched alkyl group having 1 to 10 carbon atoms, a linear or branched alkoxy group having 1 to 10 carbon atoms, a linear or branched alkenyl group having 2 to 10 carbon atoms, a linear or branched alkenyloxy group having 2 to 10 carbon atoms, a linear or branched alkynyl group having 2 to 10 carbon atoms, a linear or branched alkynyloxy group having 2 to 10 carbon atoms, a cycloalkyl group having 3 to 10 carbon atoms, a cycloalkoxy group having 3 to 10 carbon atoms, a cycloalkenyl group having 3 to 10 carbon atoms, a cycloalkenyloxy group having 3 to 10 carbon atoms, an aryl group having 6 to 10 carbon atoms, and an aryloxy group having 6 to 10 carbon atoms, wherein the organic group optionally contains a fluorine atom, an oxygen atom, or an unsaturated bond; and a and c are each an integer of 0 to 6; b and d are each an integer of 0 to 4; and e is an integer of 0 to 8.

4. The non-aqueous electrolyte solution according to claim 3, wherein, in the formula [1], formula [2], formula [3], and formula [4], $R^3$ is a methyl group, an ethyl group, a propyl group, a vinyl group, an allyl group, an ethynyl group, a 2-propynyl group, or a phenyl group;

$R^5$, $R^6$, $R^7$, $R^8$, and $R^9$ are each independently a fluorine atom or a group selected from the group consisting of a methyl group, a vinyl group, an allyl group, an allyloxy group, an ethynyl group, a 2-propynyl group, and a phenyl group; and a, b, c, d, and e are each an integer of 0 to 2.

5. The electrolyte solution for a non-aqueous electrolyte solution battery according to claim 1, wherein a content of the additive for a non-aqueous electrolyte solution is within a range of 0.001 to 5.0 mass % based on the total amount of the non-aqueous solvent, the solute, and the additive for a non-aqueous electrolyte solution.

6. The electrolyte solution for a non-aqueous electrolyte solution battery according to claim 5, wherein the solute is at least one selected from the group consisting of $LiPF_6$, $LiBF_4$, $LiPF_2(C_2O_4)_2$, $LiPF_4(C_2O_4)$, $LiP(C_2O_4)_3$, $LiBF_2(C_2O_4)$, $LiB(C_2O_4)_2$, $LiPO_2F_2$, $LiN(POF_2)_2$, $LiN(FSO_2)(POF_2)$, $LiN(FSO_2)(POF(OCH_2C\equiv CH))$, $LiN(FSO_2)_2$, $LiN(CF_3SO_2)_2$, $LiN(CF_3SO_2)(FSO_2)$, $LiSO_3F$, $NaPF_6$, $NaBF_4$, $NaPF_2(C_2O_4)_2$, $NaPF_4(C_2O_4)$, $NaP(C_2O_4)_3$, $NaBF_2(C_2O_4)$, $NaB(C_2O_4)_2$, $NaPO_2F_2$, $NaN(POF_2)_2$, $NaN(FSO_2)(POF_2)$, $NaN(FSO_2)(POF(OCH_2C\equiv CH))$, $NaN(FSO_2)_2$, $NaN(CF_3SO_2)2$, $NaN(CF_3SO_2)(FSO_2)$, and $NaSO_3F$.

7. The electrolyte solution for a non-aqueous electrolyte solution battery according to claim 1, the electrolyte solution further comprising at least one selected from the group consisting of vinylene carbonate, fluoroethylene carbonate, ethynylethylene carbonate, trans-difluoroethylene carbonate, (ethoxy)pentafluorocyclotriphosphazene, tetravinylsilane, and 1,3-propanesultone.

8. The electrolyte solution for a non-aqueous electrolyte solution battery according to claim 1, wherein the non-aqueous solvent is at least one selected from the group consisting of a cyclic carbonate, a chain carbonate, a cyclic ester, a chain ester, a cyclic ether, a chain ether, a sulfone compound, a sulfoxide compound, and an ionic liquid.

9. A non-aqueous electrolyte solution battery comprising a positive electrode, a negative electrode, and the electrolyte solution for a non-aqueous electrolyte solution battery according to claim 1.

\* \* \* \* \*